(12) United States Patent
Roberts et al.

(10) Patent No.: US 8,178,317 B2
(45) Date of Patent: May 15, 2012

(54) COMPOSITIONS AND METHODS FOR IDENTIFYING TRANSFORMING AND TUMOR SUPPRESSOR GENES

(75) Inventors: Thomas M. Roberts, Cambridge, MA (US); Jean Zhao, Brookline, MA (US); David E. Hill, Arlington, MA (US); William C. Hahn, Newton, MA (US); Jesse Boehm, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 233 days.

(21) Appl. No.: 12/150,941

(22) Filed: May 1, 2008

(65) Prior Publication Data

US 2009/0047675 A1 Feb. 19, 2009

Related U.S. Application Data

(60) Provisional application No. 60/927,066, filed on May 1, 2007.

(51) Int. Cl.
*C12P 21/06* (2006.01)
*C07H 21/02* (2006.01)

(52) U.S. Cl. ...................... 435/69.1; 536/23.1

(58) Field of Classification Search .............. 536/23.1; 435/69.1
See application file for complete search history.

(56) References Cited

U.S. PATENT DOCUMENTS

| 5,741,899 A * | 4/1998 | Capon et al. ............... 536/23.4 |
| 6,916,846 B2 | 7/2005 | Farrar et al. |
| 2004/0081647 A1 * | 4/2004 | Afeyan et al. ............ 424/94.63 |

FOREIGN PATENT DOCUMENTS
WO WO-01/83808 11/2001

OTHER PUBLICATIONS

Golub et al. 1994; Fusion of PDGF receptor_to a novel ets-like gene, tel, in chronic myelomonocytic leukemia with t(5; 12) chromosomal translocation. Cell. 77:307-316.*
Maeda et al. 2005, published on-line 2004; Transforming property of TEL-FGFR3 mediated through PI3-K in a T-cell lymphoma that subsequently progressed to aML. Blood 105(5):2115-2123.*
Jarvik et al. 1998; Epitope tagging. Annual Review of Genetics. 32:601-618.*
McWhirter et al. 1993; A coiled-coil oligomerization domain of Bcr is essential for the transforming function of Bcr-ABL oncoproteins. Molecular and cellular Biology. 13(12): 7587-7595.*
Aoki, M. et al., "The AKT Kinase: Molecular Determinants of Oncogenicity," Proc. Natl. Acad. Sci. USA 95:14950-14955 (1998).
Boehm, J.S. et al., "Integrative Genomic Approaches Identify IKBKE as a Breast Cancer Oncogene," Cell 129:1065-1079 (2007).
Jaaro, H. et al., "A Genome Wide Screening Approach for Membrane-Targeted Proteins," Molec. Cell. Proteomics 4:328-333 (2005).

Mende, I. et al., "Oncogenic Transformation Induced by Membrane-Targeted AKT2 and AKT3," Oncogene 20:4419-4423 (2001).
Invitation to Pay Additional Fees and Partial International Search Report dated Oct. 14, 2008 from PCT/US2008/062230.
Bamford et al., "The COSMIC (Catalogue of Somatic Mutations in Cancer) database and website," British Journal of Cancer, 91:355-358 (2004).
Bartkova et al., "Cyclin D1 protein expression and function in human breast cancer," Int. J. Cancer, 57(3):353-361 (1994).
Berger et al., "Androgen-Induced Differentiation and Tumorigenicity of Human Prostate Epithelial Cells," Cancer Research, 64:8867-8875 (2004).
Boehm et al., "Transformation of Human and Murine Fibroblasts without Viral Oncoproteins," Molecular and Cellular Biology, 25(15):6464-6474 (2005).
Brown et al., "Control of I kappa B-alpha proteolysis by site-specific, signal-induced phosphorylation," Science, 267:1485-1488 (1995).
Brunet et al., "Constitutively active mutants of MAP kinase kinase (MEK1) induce growth factor-relaxation and oncogenicity when expressed in fibroblasts," Oncogene, 9(11):3379-3387 (1994).
Carroll et al., "The TEL/platelet-derived growth factor β receptor (PDGFβR) fusion in chronic myelomonocytic leukemia is a transforming protein that self-associates and activates PDGFβR kinase-dependent signaling pathways," Proc. Natl. Acad. Sci. USA, 93:14845-14850 (1996).
Chudnovsky et al., "Use of human tissue to assess the oncogenic activity of melanoma-associated mutations," Nat. Genet., 37(7):745-749 (2005).
Davies et al., "Mutations of the BRAF gene in human cancer," Nature, 417:949-954 (2002).
Downward, J., "Targeting RAS signalling pathways in cancer therapy," Nat. Rev. Cancer, 3(1):11-22 (2003).
Eisenhaber et al., "Post-translational GPI lipid anchor modification of proteins in kingdoms of life: analysis of protein sequence data from complete genomes," Protein Engineering, 14(1):17-25 (2001).
Elenbaas et al., "Heterotypic signaling between epithelial tumor cells and fibroblasts in carcinoma formation," Exp. Cell Res., 264(1):169-184 (2001).
Fan et al., "Homo- and Hetero-Oligomerization of the c-Abl Kinase and Abelson-Interactor-1," Cancer Research, 63:873-877 (2003).
Farrar et al., "Activation of the Raf-1 kinase cascade by coumermycin-induced dimerization," Nature, 383:178-181 (1996).
Fitzergerald et al., "IKKepsilon and TBK1 are essential components of the IRF3 signaling pathway," Nat. Immunol., 4(5):491-496 (2003).
Garraway et al., "Integrative genomic analyses identify MITF as a lineage survival oncogene amplified in malignant melanoma," Nature, 436:117-122 (2005).

(Continued)

*Primary Examiner* — Karen Carlson
(74) *Attorney, Agent, or Firm* — Foley Hoag LLP

(57) ABSTRACT

Provided herein are nucleic acids, proteins, vectors, cells, kits, devices and methods useful for identifying regulatable proteins that are able to complement components of cellular signaling pathways. Also provided are compositions and methods using these complementing genes directly as markers for cancer diagnosis or prognosis and as targets for anti-neoplastic therapeutics. Further provided are methods for using changes caused by expression of the complementing genes to indirectly identify associated genes to be used as markers for cancer diagnosis or prognosis and as targets for anti-neoplastic therapeutics.

35 Claims, 20 Drawing Sheets

OTHER PUBLICATIONS

Golub et al., "Oligomerization of the ABL Tyrosine Kinase by the Ets Protein TEL in Human Leukemia," Molecular and Cellular Biology, 16(8):4107-4116 (1996).
Hahn et al., "Creation of human tumour cells with defined genetic elements," Nature, 400:464-468 (1999).
Hahn et al., "Enumeration of the Simian Virus 40 Early Region Elements Necessary for Human Cell Transformation," Molecular and Cellular Biology, 22(7):2111-2123 (2002).
Hanks et al., "The protein kinase family: conserved features and deduced phylogeny of the catalytic domains," Science, 241:42-52 (1988).
Harbury et al., "A switch between two-, three-, and four-stranded coiled coils in GCN4 leucine zipper mutants," Science, 262:1401-7 (1993).
Harris et al., "Nuclear Accumulation of cRel following C-Terminal phosphorylation by TBK1/IKKε1," J. Immunol., 177:2527-2535 (2006).
Hunter, T., "Cooperation between oncogenes," Cell, 64(2):249-270 (1991).
Johnson et al., "Genetic and biochemical studies of protein N-myristoylation," Annu. Rev. Biochem., 63:869-914 (1994).
Kendall et al., "A Network of Genetic Events Sufficient to Convert Normal Human Cells to a Tumorigenic State," Cancer Res. 65:9824-9828 (2005).
Klippel et al., "Membrane Localization of Phosphatidylinositol 3-Kinase Is Sufficient to Activate Multiple Signal-Transducing Kinase Pathways," Molecular and Cellular Biology, 16(8):4117-4127 (1996).
Kohn et al., "Akt, a Pleckstrin Homology Domain Containing Kinase, Is Activated Primarily by Phosphorylation," J. Biol. Chem., 271(36):21920-21926 (1996).
Li et al., "A novel conditional Akt 'survival switch' reversibly protects cells from apoptosis," Gene Therapy, 9:233-244 (2002).
Lundberg et al., "Immortalization and transformation of primary human airway epithelial cells by gene transfer," Oncogene, 21:4577-4586 (2002).
MacKenzie et al., "Multiple stages of malignant transformation of human endothelial cells modelled by co-expression of telomerase reverse transcriptase, SV40 T antigen and oncogenic N-ras," Oncogene, 21:4200-4211 (2002).
Manning et al., "The protein kinase complement of the human genome," Science, 298:1912-1934 (2002).
Maurer-Stroh et al., "N-terminal N-myristoylation of proteins: prediction of substrate proteins from amino acid sequence," J. Mol. Biol., 317(4):541-557 (2002).
Maurer-Stroh et al., "Refinement and prediction of protein prenylation motifs," Genome Biology, 6:R55 (2005).
Moffat et al., "A lentiviral RNAi library for human and mouse genes applied to an arrayed viral high-content screen," Cell, 124(6):1283-1298 (2006).
Monaco et al., "The RFG oligomerization domain mediates kinase activation and re-localization of the RET/PTC3 oncoprotein to the plasma membrane," Oncogene, 20:599-608 (2001).
Morgenstern et al., "Advanced mammalian gene transfer: high titre retroviral vectors with multiple drug selection markers and a complementary helper-free packaging cell line," Nucleic Acids Research, 18(12):3587-3596 (1990).
Ney et al., "Purification of the Human NF-E2 Complex: cDNA Cloning of the Hematopoietic Cell-Specific Subunit and Evidence for an Associated Partner," Molecular and Cellular Biology, 13(9):5604-5612 (1993).
Ozes et al., "NF-kappaB activation by tumour necrosis factor requires the Akt serine-threonine kinase," Nature, 401:82-85 (1999).
Peters et al., "IKKepsilon is part of a novel PMA-inducible IkappaB kinase complex," Mol. Cell, 5(3):513-522 (2000).
Pinkel et al., "High Resolution analysis of DNA copy number variation using comparative genomic hybridization to microarrays," Nat. Genet., 20(2):207-211 (1998).
Pollock et al., "Regulation of gene expression with synthetic dimerizers," Methods Enzymol., 306:263-281 (1999).
Ramaswamy et al., "Regulation of $G_1$ progression by the PTEN tumor suppressor protein is linked to inhibition of the phosphatidylinositol 3-kinase / Akt pathway," Proc. Natl. Acad. Sci. USA, 96:2110-2115 (1999).
Rennstam et al., "Patterns of Chromosomal Imbalances Defines Subgroups of Breast Cancer with Distinct Clinical Features and Prognosis. A Study of 305 Tumors by Comparative Genomic Hybridization," Cancer Research, 63:8861-8868 (2003).
Rich et al., "A Genetically Tractable Model of Human Glioma Formation," Cancer Research, 61:3556-3560 (2001).
Rivera, V.M., "Controlling Gene Expression Using Synthetic Ligands," Methods, 14(4):421-429 (1998).
Romashkova et al., "NF-kappaB is a target of AKT in anti-apoptotic PDGF signaling," Nature, 401:86-90 (1999).
Rual et al., "Human ORFeome Version 1.1: A Platform for Reverse Proteomics," Genome Research, 14:2128-2135 (2004).
Serrano et al., "Oncogenic ras provokes premature cell senescence associated with accumulation of p53 and p16INK4a," Cell, 88(5):593-602 (1997).
Sharma et al., "Triggering the interferom antiviral response through an IKK-related pathway," Science, 300:1148-1151 (2003).
Sigal et al., "Amino-terminal basic residues of Src mediate membrane binding through electrostatic interaction with acidic phospholipids," Proc. Natl. Acad. Sci. USA, 91:12253-12257 (1994).
Stanton et al., "Definition of the Human raf Amino-Terminal Regulatory Region by Deletion Mutagenesis," Molecular and Cellular Biology, 9(2):639-647 (1989).
Towler et al., "The biology and enzymology of eukaryotic protein acylation," Annu. Rev. Biochem., 57:69-99 (1988).
Ung et al., "Heterologous dimerization domains functionally substitute for the double-stranded RNA binding domains of the kinase PKR," The EMBO Journal, 20(14):3728-3737 (2001).
Weinstein et al., "Mechanisms of disease: Oncogene addiction—a rationale for molecular targeting in cancer therapy," Nat. Clin. Pract. Oncol., 3(8):448-457 (2006).
Yao et al., "Combined cDNA Array Comparative Genomic Hybridization and Serial Analysis of Gene Expression Analysis of Breast Tumor Progression," Cancer Res. 66(8):4065-4078 (2006).
Yu et al., "Critical Role for SV40 Small-t Antigen in Human Cell Transformation," Virology, 290(2):192-198 (2001).
Zhao et al., "Functional genetics and experimental models of human cancer," Trends Mol. Med., 10(7):344-350 (2004).
Zhao et al., "Human mannary epithelial cell transformation through the activation of phosphatidylinositol 3-kinase," Cancer Cell, 3(5):483-495 (2003).
Zhao et al., "The oncogenic properties of mutant p110α and p110β phosphatidylinositol 3-kinases in human mammary epithelial cells," Proc. Natl. Acad. Sci. USA, 102:18443-18448 (2005).
Zhao et al., "RSK3 Encodes a Novel pp90*rsk* Isoform with a Unique N-Terminal Sequence: Growth Factor-Stimulated Kinase Function and Nuclear Translocation," Molecular and Cellular Biology, 15(8):4353-4363 (1995).
Zhao et al., "An Integrated View of Copy Number and Allelic Alterations in the Cancer Genome Using Single Nucleotide Polymorphism Arrays," Cancer Research, 64:3060-3071 (2004).

* cited by examiner

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Ala Ile Lys
  1

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Gly Ser Ser Lys Ser Lys Pro Lys Asp Pro Ser Gln Arg Arg Arg
  1               5                  10                  15

Arg Ile Arg Gly
             20

<210> SEQ ID NO 3
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Glu Thr Pro Ala Gln Cys Ser Ile Lys Gln Glu Arg Ile Ser
  1               5                  10                  15

Tyr Thr Pro Pro Glu Ser Pro Val Pro Ser Tyr Ala Ser Ser Thr Pro
                 20                  25                  30

Leu His Val Pro Val Pro Arg Ala Leu Arg Met Glu Glu Asp Ser Ile
             35                  40                  45

Arg Leu Pro Ala His Leu Arg Leu Gln Pro Ile Tyr Trp Ser Arg Asp
         50                  55                  60

Asp Val Ala Gln Trp Leu Lys Trp Ala Glu Asn Glu Phe Ser Leu Arg
 65                  70                  75                  80
```

```
Pro Ile Asp Ser Asn Thr Phe Glu Met Asn Gly Lys Ala Leu Leu Leu
                85                  90                  95

Leu Thr Lys Glu Asp Phe Arg Tyr Arg Ser Pro His Ser Gly Asp Val
        100                 105                 110

Leu Tyr Glu Leu Leu Gln His Ile Leu Lys Gln Arg Lys Pro Arg Ile
    115                 120                 125

Leu Phe Ser Pro Phe Phe His Pro Gly Asn Ser Ile His Thr Gln Pro
    130                 135                 140

Glu Val Ile Leu His Gln Asn His Glu Glu
145                 150

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgcgtgcaga agtatcaagc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tacaggcagc cacagaacag                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctggactc catgaaagac                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacacgtgtg gccattgtag                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aactacctgg accgcttcct                                              20
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccacttgagc ttgttcacca                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcgggtagt ggaaaaccag                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagcagctcg aatttcttcc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgagcatcta cggtttgctg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgcttgtctg gaacaactgc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aatgacgccc tcaatcaaag                                              20

<210> SEQ ID NO 15
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgggtatctc aggcatctcc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttgacagcga caagaagtgg                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccattcacg tcgtccttat                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cccactgagg agtccaacat                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tttcttgcgc tttcgttttt                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccaggtccct cgtatcaaaa                                               20

<210> SEQ ID NO 21
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 21
aaaccagcac gagcaagact                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctttgcctgt ggtggaaaat                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acttgcaagc tgctcaggat                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaggattgtg gccttctttg                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acagttccac aaaggcatcc                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actgcctcaa ggacaggatg                                                   20

<210> SEQ ID NO 27
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 27
agccaggagg ttctcaacaa                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccatattcct cggacaccac                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgtactcccg aacccatttc                                                   20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cccttcattg tagatctgat t                                                 21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gccaacctgg aagaggaatt t                                                 21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgggcaggag ctaatgtttc g                                                 21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 33
gtccttagtc acacacggca a                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gagcattgga gtgaccttgt a                                              21
```

COMPOSITIONS AND METHODS FOR IDENTIFYING TRANSFORMING AND TUMOR SUPPRESSOR GENES

RELATED APPLICATIONS

This application claims the benefit of U.S. Provisional Application Ser. No. 60/927,066 filed on May 1, 2007; the entire contents of the application is incorporated herein by reference.

STATEMENT OF RIGHTS

This invention was made with government support under Grants K01 CA94223, P50 CA112962, CA30002, CA89021 and CA015607 awarded by the National Institutes of Health and BC051565 awarded by the Department of Defense. The government has certain rights in the invention.

BACKGROUND OF THE INVENTION

Cancer is one of the leading causes of death in the United States. Each year, more than half a million Americans die from cancer and more than one million are newly diagnosed with the disease. Cancer develops from normal tissues through a stepwise accumulation of genetic mutations that causes a cell to escape from its normal growth regulatory mechanisms and proliferate in an uncontrolled manner. Tumor cells can metastasize to secondary sites if treatment of the primary tumor is either incomplete or not initiated before the disease progresses substantially. Early diagnosis and effective treatment of tumors are therefore essential for survival.

Cancer involves the clonal replication of cell populations that have gained a competitive advantage over normal cells through the alteration of regulatory gene expression. Regulatory genes can be broadly classified into two categories including "oncogenes" which, when activated or overexpressed, promote unregulated cell proliferation and "tumor suppressor genes" which, when inactivated or underexpressed, fail to prevent abnormal cell proliferation. A handful of oncogenes have been identified that, when abnormally activated, are involved in the initiation or progression of human cancers. Known oncogenes include, for example, Myc, Ras, Src, and HER2. Similarly, a handful of tumor suppressor genes have been identified that, when inactivated, are involved in the initiation or progression of human cancers. Known tumor suppressor genes include, for example, RB, p53, DCC, APC/MCC, NF1, NF2, WT1, VHL, BRCA1, MST1 and WAF1/CIP1.

In contrast to the small handful of characterized oncogenes and tumor suppressor genes, the recent completion of the human genome sequence has revealed the existence of upwards of 30,000 genes that may contain critical, unidentified oncogenes and tumor suppressor genes. For example, protein kinases are just one family of signaling pathway regulators whose members are known to cause malignant transformation when dysregulated. It is now appreciated that the total complement of human protein kinases is encoded by greater than 500 genes, making them the most populated class of potential druggable cancer targets.

Despite the potential for discovering critical oncogenes and tumor suppressor genes that the human genome has allowed, the route to realizing this potential has been blocked by the fact that most human cancers, particularly epithelial cancers, exhibit global genomic alterations and karyotypic abnormalities that make it difficult to identify specific mutations critical for cell transformation. Moreover, abundant evidence suggests that multiple mutations are required to program the transformed phenotype.

These facts underscore the importance of dissecting the molecular interactions taking place in cells as they develop increasing numbers of mutations. There exists a need, therefore, both to identify novel oncogenes and tumor suppressor genes and to dissect and better characterize the interactions among members of each class.

SUMMARY OF THE INVENTION

This invention relates generally to compositions and methods useful for the dissection of signal transduction pathways that cause oncogenesis in humans and, more specifically, for the identification of genes that modulate cellular transformation that are both physiologically relevant to human cancers and therapeutically attractive for cancer treatment. Described herein are methods that comprise an essential tool to identify oncogenes and tumor suppressor genes.

Provided herein are compositions comprising one or more nucleic acids encoding one or at least two regulatable proteins, each linked to one or more regulatory signals, wherein expression of the regulatable proteins in a cell results in the regulatable protein being regulated, e.g., constitutively regulated. The one or more nucleic acids may encode at least 1, 2, 3, 5, 10 or more regulatable proteins. A regulatable protein may be a kinase, e.g., in Table 1, or a biologically active fragment thereof, such as an intracellular domain, e.g., a catalytic domain. The regulatable proteins or biologically active portions thereof may be linked to an activation signal, such as a membrane targeting signal, e.g., a myristoylation signal. This signal may be linked to the N- or C-terminus of the kinases or biologically active portions thereof. In one embodiment, the kinase is a receptor tyrosine kinase that is linked to a membrane targeting signal.

A regulatable protein may also be linked to an activation signal that is an oligomerization, e.g., dimerization domain. The dimerization domain may be an inducible dimerization domain, e.g., a dimerization domain that is induced to dimerize in the presence of a small molecule. The oligomerization domain may be linked to the N- or C-terminus of the kinases or biologically active portions thereof. A regulatable protein may be linked to both a membrane targeting signal and an oligomerization domain.

A regulatable protein may further be linked to a detectable peptide, such as a FLAG tag. At least one regulatable protein may be linked directly to one or more regulatory signals. At least one regulatable protein may be linked to one or more regulatory signals through a linker.

One or more nucleic acids may comprise one or more strong transcriptional regulatory sequences controlling the expression of the regulatable proteins. The nucleic acids may be in an expression vector, e.g., a viral expression vector.

In certain embodiments, a composition comprises a reagent for introducing the composition into a cell. In certain embodiments, a composition is in contact with or within a cell. A cell may be an immortalized non-tumorigenic cell. A cell may be a human cell.

A composition may also comprise at least 1, 2, 5, 10 or more nucleic acids, wherein each nucleic acid encodes a regulatable protein linked to one or more regulatory signals. A composition may also comprise a library of nucleic acids encoding regulatable proteins linked to one or more regulatory signals.

Also provided are kits, e.g., kits comprising a nucleic acid encoding a regulatable protein linked to one or more regulatory signals and packaging for said kit. Also provided are devices, e.g., devices comprising a location, wherein the location comprises a nucleic acid encoding a regulatable protein linked to one or more regulatory. A device may be a multiwell device and the location may be a well.

Further provided are compositions comprising one or more nucleic acids encoding one or at least two inhibitory mutants of proteins, wherein expression of the inhibitory mutants in a cell downregulates one or more biological activities associated with the corresponding wild-type proteins. At least one protein may be a kinase, a phosphatase, an acetylase, or a deacetylase. At least one inhibitory mutant of a protein may be a dominant negative mutant of the protein, a deletion mutant of the protein, a protein comprising a substitution of one or more amino acids, e.g., wherein one or more substitutions of amino acids results in a change in posttranslational modification of the protein. One or more substitutions of amino acids may result in a change in a posttranslational modification of the protein, such as acetylation, glycosylation or phosphorylation.

The following exemplary methods are also encompassed. A method comprising contacting one or more cells with a composition comprising one or more nucleic acids or proteins encoded thereby. The cells may be contacted with the composition under conditions in which at least some of the nucleic acids of the composition are taken up by the cells. The cells may be immortal but not tumorigenic cells. The cells may comprises one or more of the following genes and oncogenes or proteins including, but not limited to: the catalytic subunit of telomerase (hTERT), telomerase, human papilloma virus E6, Human papilloma virus E7, cyclin D1, an R24C form of CDK4 (CDK4$^{R24C}$), p53DD, MYC, phosphatidylinositol-3-kinase, adenovirus early region 1A (E1A), E6, E7, MDM2, SV40 large T antigen, SV40 small T antigen, RAC/RHO, PI3K, AKT, RAF, MEK, MEKDD, MAPK, RAL-GEFs, RAL, PLD1, H-RAS, an activated allele of H-RAS (H-RAS$^{V12}$), ALT, CycD1/CDK4, or variants or fragments thereof that may be oncogenic or other such genes known in the art. The cells may also comprise one or more inactivated or inhibited tumor suppressor genes or proteins, including, but not limited to: p53, retinoblastoma (Rb), PP2A, p19ARF, p16$^{INK4A}$ or PTEN tumor suppressor genes or variants or fragments thereof that may be tumor suppressors or other such genes known in the art. Quasi-transformed cells may also comprise a combination of one or more oncogenes and one or more inactivated tumor suppressor genes. The method may further comprise determining whether the cells contacted with the composition are tumorigenic. This may comprise determining whether the cells contacted with the nucleic acids grow in an anchorage-independent manner and/or promote tumor formation in animal hosts. In one method, the cells require a growth factor, e.g., IL-3, for growth and the method further comprises determining whether the cells contacted with the composition grow independently of the growth factor.

Also provided herein are methods for determining whether a subject has or is likely to develop a disease or disorder, e.g. cancer, associated with a regulatable protein identified herein. A method may comprise determining the level of the regulatable protein, e.g., IKKε, in a sample of a subject, wherein a higher or lower level and/or activity of the regulatable protein in the sample of the subject relative to that in a control indicates that the sample is or may become cancerous. A method may also comprise determining the expression level of the regulatable protein in a tissue in a subject, wherein the presence of a higher or lower level of the regulatable protein in the tissue relative to a control indicates that the subject has or may develop cancer. Determining the level of the regulatable protein may comprise (i) determining the protein level of the regulatable protein, e.g., by immunohistochemical staining or by activity such as a phosphorylation assay; (ii) determining the level of RNA encoding the regulatable protein, e.g., by Northern blot or quantitative PCR; and/or (iii) detecting changes in copy number of genomic loci encoding the regulatable protein, e.g. by array comparative genome hybridization or fluorescence in situ hybridization. A control may be the level of the regulatable protein in non-cancerous cells of the same origin as those of the potentially cancerous tissue sample. The potentially cancerous tissue sample may be a cancerous tumor. The method may further comprise first obtaining a biopsy of a tissue sample of the subject.

Other methods provided herein are methods for monitoring the progression of a cancer in a subject. A method may comprise monitoring the level of a regulatable protein, e.g., IKKε, in a cancerous tumor of the subject over time, wherein an increase or decrease in the level of the regulatable protein in a cancerous tumor of the subject indicates that the cancer is progressing.

Further provided herein are kits, e.g., kits comprising one or more agents for detecting the level of a regulatable protein, e.g., IKKε. A kit may also comprise a control. A control may be the level of the regulatable protein in a cancerous tumor or in a tissue of a healthy subject. The agent for detecting the level of the regulatable protein may be an antibody or a variant, e.g., a fragment, thereof. The agent for detecting the level of the regulatable protein may also comprise reagents necessary to detect the protein of the regulatable protein, the RNA encoding the regulatable protein and changes in copy number of genomic loci encoding the regulatable protein.

Therapeutic methods are also provided herein. An exemplary method for treating a subject having a cancer associated with abnormal levels or activity of a regulatable protein, e.g. high levels of IKKε, relative to an appropriate control, comprises administering to the subject a therapeutically effective amount of an agent that modulates the level of the regulatable protein, e.g. reduces the level of IKKε.

BRIEF DESCRIPTION OF THE DRAWING

FIG. 2A is a schematic diagram outlining the library generation and screening strategies. FIG. 2B is a graph showing AI growth of pools named by their plate number (1-5) and row (A-H). (−) and GFP indicate the number of colonies produced by mock- and GFP-vector-infected cells, respectively. Black line and red dotted line indicate the median and 2 standard deviations above the median, respectively. FIG. 2C is a graph identifying putative kinase oncogenes from top scoring pools. Error bars indicate the mean±standard deviation for 3 independent experiments.

FIG. 3A shows analysis of the IKBKE locus by single nucleotide polymorphism (SNP) arrays in 49 breast cancer cell lines. Colorgrams representing SNP copy number at 1q32 are shown. Red indicates allelic gain, while blue denotes allelic loss. FIG. 3B shows clustering of array comparative genome hybridization (aCGH) data based on chromosome 1 copy number gain of 30 breast primary tumors. Colored rectangles indicate tumor grade (red-high, purple-intermediate, and blue-low grade) and lymph node (LN), estrogen receptor (ER), or HER2 status (red-positive, blue-negative, and gray-unknown). FIG. 3C shows fluorescence in situ hybridization (FISH) analysis of IKBKE amplification in UACC-812, ZR-75-1 and MCF-7 breast cancer cell lines and BWH-T18 primary breast tumor. Green signal indicates hybridization using an IKBKE-specific BAC probe, while red color indicates hybridization using a chromosome 1-specific alpha satellite DNA probe (left panels) or chromosome 1 painting probe (right panels). FIG. 3D shows quantitative RT-PCR (qRT-PCR) analysis of IKBKE expression in breast cancer cell lines and patient samples. Carcinomas and cell lines are color-coded to indicate presence of amplified 1q32 (blue-non-amplified, red-amplified). Asterisks (*) indicate patient samples with corresponding aCGH data in FIG. 3B. Raw values were normalized to RPL39 levels determined in parallel. Fold changes are referenced to values obtained with the normal sample with the highest IKBKE expression, N050702. FIG. 3E shows immunoblotting for IKKε. Using the K-14 anti-IKKε antibody (Santa Cruz), immunoblot in left panel compares breast cancer and immortalized breast cell lines lacking IKBKE copy number gain (MCF10A, MCF10A.DCIS.COM) to breast cancer cell lines with low levels of IKBKE (MCF-7, MDA-MB-231) and the middle immunoblot compares breast cancer cell lines harboring different levels of IKBKE copy number gain. The immunoblot on the right was performed with a different anti-IKKε antibody (Sigma C-terminal). FIG. 3F shows AI growth of HMEC-M cells harboring either a control vector (vector) or myr-IKBKE. Bar represents 2 mm. Colony number reflects large macroscopic colonies (>1 mm).

FIG. 4A shows that IKBKE is essential for MCF-7 cell viability. Lower panels show IKKε expression in MCF-7 cells expressing IKBKE-specific shRNAs or a control shRNA targeting GFP (shGFP). FIG. 4B shows the effects of suppressing kinase genes located at 1q32. MCF-7 cells were infected with shRNA constructs (5/gene) targeting 10 kinases (ETNK2, PIK3C2B, RIPK5, DYRK3, IKBKE, MAPKAP2, PCTK3, PFKFB2, NIJCKS1 and NUAK2) located at 1q32. Solid line represents the median, dotted lines indicate 1 and 1.5 SD below the median. shRNA targeting IKBKE (red), NUAK2 (blue), PFKFB2 (yellow), and ETNK2 (black) or the other genes (gray) are shown. FIG. 4C shows the effects of IKKε suppression on viability. Representative micrographs obtained 5 days after infection with the indicated shRNA are shown. FIG. 4D shows the effects of IKKε suppression on proliferation. Cells were plated on day 0, infected with IKBKE shRNA 24 hours later and cumulative cell numbers determined for 11 days. The doubling time for each cell line was determined and then normalized to cells expressing a control, scrambled shRNA (shScr). Expression of IKKε is shown in lower panels for the indicated cell lines.

FIGS. 5A-D show that IKKε activates the NF-κB pathway in transformation models. FIG. 5A and FIG. 5B show the effects of IKKε expression on IκBα stability. Cytoplasmic IκBα levels in HA1E-M cells are shown and quantified. FIG. 5C shows RT-PCR and immunoblot (Western blot) analysis of IκBα overexpression. MUT: IκBα super-repressor, wt: wt IκBα allele. FIG. 5D and FIG. 5E show localization of NF-κB p50. The antibody used here detects both NF-κB p50 and the NF-κB p50 precursor (p105). FIG. 5F shows NF-κB reporter activity in the indicated cell lines. FIG. 5G shows changes in expression of selected NF-κB-regulated genes in HA1E-M cells harboring either a control vector (−) or myr-IKBKE (+). FIG. 5H shows changes in expression of selected NF-κB-regulated genes in HMEC-M cells harboring either a control vector (−) or WT IKBKE (+). FIG. 5I shows an analysis of cyclin D1 protein levels in HA1E cells expressing MEKDD and/or the indicated genes. FIG. 5J and FIG. 5K show the effects of expressing MUT IκBα on the doubling time (FIG. 5J) and AI growth (FIG. 5K) of HA1E-M cells expressing either myr-IKBKE or myr-AKT. FIG. 5L shows the effects of suppressing IKBKE on AI growth of AKT-transformed cells. (−) indicates control cells.

FIG. 6A shows downregulation of NF-κB target genes in ZR-75-1 breast cancer cells after IKBKE suppression as determined by quantitative RT-PCR. FIG. 6B and FIG. 6C show the relative expression of MMP9 (FIG. 6B) and BCL2 (FIG. 6C) in breast cancer cell lines that harbor (UACC-812, ZR-75-1, MCF-7) or lack (SUM52) IKKε gain or amplification. UACC-812 cells do not express BCL2. FIG. D and FIG. 6E show examination of IKKε overexpression and NF-κB pathway activation in primary breast cancer specimens. FIG. 6D shows representative IHC staining and scoring used to assess IKKε and nuclear c-REL expression. 0: no staining, 1: low staining, 2: moderate staining, 3: high staining. FIG. 6E shows co-expression of IKKε and nuclear c-REL. Each point represents one breast cancer specimen. p values were determined by Fisher's exact test.

FIG. 7A shows the efficiency of retroviral infection of Gateway®-compatible retroviral vectors. HA1E cells were infected with pBabe-GFP (green bars-left) or pBabe-YFP (yellow bars-left) constructs. pWN-MF-DEST-YFP and pWN-MF-DEST-GFP were created by performing site-specific LR recombination reactions between pEntry-YFP or pEntry-GFP and pWN-MF-DEST. HA1E cells were infected with pWN-MF-DEST-GFP (green bars-right) and pWN-MF-DEST-YFP (yellow bars-right). The percentage of GFP- or YFP-positive cells was determined by fluorescence activated cell sorting after a single retroviral infection. FIG. 7B shows localization of ORFs expressed by pWN-MF-DEST. 293T cells were transfected with pBabe-GFP control vector or pWN-MF-DEST-GFP. GFP in this experiment occupies the position of a kinase ORF. Micrographs depict membrane localization of GFP, confirming that the myristoylation tag is in frame and functional.

FIG. 9A shows the activity of the IRF3-responsive interferon-regulated promoter element (ISRE) derived from the IFIT2 gene encoding ISG54 in HA1E-M cells harboring either a control vector or vectors encoding myr-IKBKE or WT IKBKE. FIG. 9B and FIG. 9C show quantitative PCR analysis of interferon regulated genes, IFNB1 and CCL5, in HA1E-M cells expressing myr-IKBKE (FIG. 9B) or HMEC-M cells expressing WT IKBKE (FIG. 9C). Raw values were normalized to GAPDH and to cells expressing a control vector. FIG. 9D shows suppression of IRF3 in IKBKE-expressing cells by two IRF-3-specific shRNA (shIRF3-#1, shIRF3-#2). FIG. 9E shows effects of suppressing IRF3 on IKBKE-induced transformation. AI colony formation for HA1E-M cells expressing myr-IKBKE plus shIRF3-#1 or shIRF3-#2. (−) indicates mock-infected cells. Error bars in A, B, and E represent mean±SD for 3 independent experiments.

FIG. 10A shows a schematic diagram illustrating how kinase can be activated by either myristoylation or dimerization. FIG. 10B shows activation of cRaf, a serine/threonine kinase, by either a myristoylation or Tel tag.

FIG. 11A shows a schematic diagram of ligand-independent dimerization of receptor tyrosine kinases (RTKs) mediated by Tel-domains. FIG. 11B shows the expression and activation of PDGFRβ-Tel and FGFR1-Tel under growth factor free conditions. Antibody 4G10 specifically recognizes phospho-Tyrosine.

DETAILED DESCRIPTION OF THE INVENTION

Figure 1:
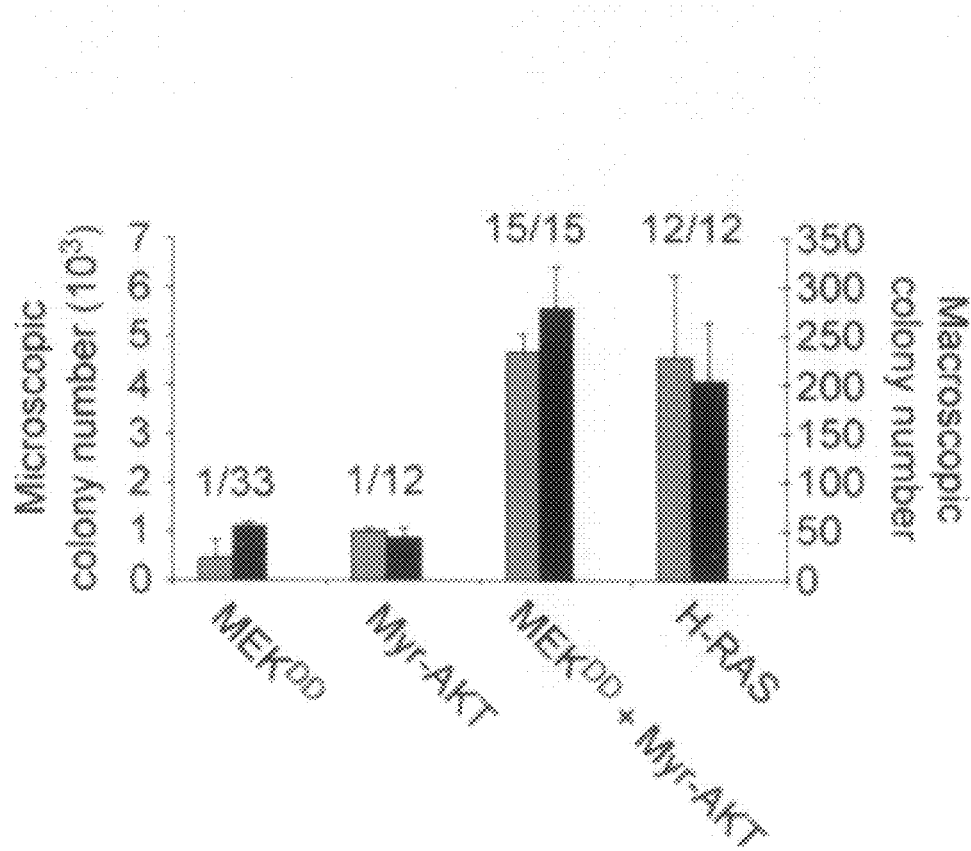
FIG. 1 is a graph showing that activated MEK1 and AKT1 can cooperate to replace H-RAS$^{V12}$ in causing anchorage-independent microscopic/macroscopic colonies and tumor formation. Anchorage-independent microscopic colonies (100 μm-200 nm, grey bars), macroscopic colonies (>200 nm, blue bars) and tumor formation (number of tumors formed/ tumor sites injected) are shown for HEK cells expressing hTERT, the SV40 ER, and the indicated genes. Error bars represent the mean±standard deviation for 3 independent experiments.

The present invention pertains, at least in part, to compositions comprising a library of nucleic acids encoding regulatable proteins, e.g., kinase and kinase related proteins or biologically active portions thereof, optionally linked to one or more regulatory signals, wherein expression of the regulatable proteins or biologically active portions thereof in a cell results in the regulatable protein or biologically active portion thereof being regulated.

Provided herein are nucleic acids, proteins, vectors, cells, kits, devices and methods for identifying genes that are able to complement genes in signaling pathways (e.g. PI3K signaling). Also provided are methods using these complementing genes directly as markers for cancer diagnosis or predisposition and as targets for anti-neoplastic therapeutics. Further provided are methods for using changes caused by expression of the complementing genes to indirectly identify associated genes to be used as markers for cancer diagnosis or predisposition and as targets for anti-neoplastic therapeutics.

Various aspects of the invention are described in further detail herein.

I. Regulatable Proteins

Described herein are compositions comprising one or more nucleic acids encoding one or at least two regulatable proteins linked to one or more regulatory signals, wherein expression of the regulatable proteins in a cell results in the regulatable protein being regulated. Compositions may comprise one or more nucleic acids encoding at least about 1, 2, 3, 4, 5, 10, 20, 50, 100, 200, 300, or 500 or more regulatable proteins. In one embodiment, a composition may comprise a library of nucleic acids encoding regulatable proteins, or pools of nucleic acids thereof. A pool of nucleic acids may encode about 5-10, 10-20, 10-30 or more regulatable proteins.

In one embodiment, each regulatable protein is encoded by a separate nucleic acid. For example, a composition may comprise at least about 1, 2, 3, 4, 5, 10, 20, 50, 100, 200, 300, or 500 nucleic acids, wherein each nucleic acid encodes one regulatable protein. As further discussed below, the nucleic acids do not need to be in one composition. In particular, each member of a library of nucleic acids may be physically separated from the other members, e.g., by being present in a well of a multiwell plate. In one embodiment, each member of a library of nucleic acids encoding regulatable proteins is present in a separate well from the other nucleic acids of the library.

Also provided herein are compositions comprising one or more regulatable proteins linked to one or more regulatory signals. A composition can comprise at least about 1, 2, 3, 4, 5, 10, 20, 50, 100 or more proteins. A composition may comprise a library of regulatable proteins or pools of proteins thereof. A pool of proteins may comprise about 5-10, 10-20, 10-30 or more proteins. The members of the library do not need to be in a composition. Each member of the library may be in a separate vial or well of a multiwell dish.

A "regulatable protein" refers to a protein whose activity can be regulated, e.g., by targeting the protein to the cell membrane or by oligomerization. A regulatable protein may be a naturally occurring protein, or a protein that is not naturally occurring, e.g., one which differs from the naturally occurring form by one or more amino acid deletions, additions or substitutions. A regulatable protein may be a biologically active fragment of a naturally occurring regulatable protein.

In one embodiment, a regulatable protein is a protein that is involved in a signal transduction pathway. As it is known in the art, a signal transduction pathway is a system within a cell that transmits information from outside the cell to the cell nucleus, resulting in a change in the expression of one or more genes. Signal transduction pathways involve the interactions of protein factors that regulate enzymatic activities (e.g., phosphorylation, phosphatase and protease activity) or the association of signal transducing factors with other factors in a cascade of interactions, wherein the cascade serves to amplify and/or direct a signal to a particular set of genes.

In one embodiment, a regulatable protein(s) regulates signal transduction pathways controlling cell growth, division, migration, survival or apoptosis. These proteins may comprise members of one or more of the following families of signaling-related proteins: cell surface receptor, kinase, phosphatase, G-protein, small GTPase, hydrolase, adapter (e.g. EF hand, SH2, SH3, PTB, TIR, FHA, MH2, WD40, BRCT, Polo-Box, FF, WW and PH domain-containing adapter and the like), ubiquitin ligase, methylase, demethylase, and transcription factors. These regulatable proteins may be components of the same biological pathway or of different biological pathways.

In one embodiment, a regulatable protein is a kinase or a kinase related protein or a biologically active fragment thereof. A kinase or a kinase related protein is capable of modulating its own phosphorylation state (autophosphorylation) or the phosphorylation state of another cellular component, such as that of other proteins or polypeptides. Such regulatable proteins may be involved in phosphorylation of proteins, lipids, carbohydrates, and/or nucleic acids. In one embodiment, a regulatable protein is a protein kinase, which is defined by the presence of at least one eukaryotic protein kinase (ePK) catalytic domain (e.g., see Manning et al. (2002) *Science* 298: 1912-1919). An ePK catalytic domain generally contains three motifs that are thought to be critical for catalytic function, each of which contains an almost invariant residue that is thought to be involved in catalysis. These three motifs include a "VAIK" motif (SEQ ID NO: 1) in which K is thought to interact with the alpha and beta phosphates of ATP to anchor and orient them, an "HRD" motif in which D likely acts as a base acceptor during catalysis, and "DFG" in which D is thought to chelate Mg++ ions of ATP (see, e.g., Hardie, D. G., et al. (1995) The Protein Kinase Factsbook, Academic Press, London and Manning et al. (2002) Science 298: 1912-1919), although kinases with different motif sequences are known in the art. A "kinase related protein" is a protein that comprises an amino acid sequence that has sequence or structural similarity to an ePK domain or a known atypical protein kinase (aPK) domain (e.g., see Manning et al. (2002) Science 298: 1912-1919) or contains the word "kinase" in its name but does not exhibit said sequence or structural features. An exemplary kinase related protein is an atypical protein kinase (aPK), such as an atypical protein kinase C, e.g., the mammalian p62-atypical protein kinase C.

Most kinases that phosphorylate proteins can have a specificity for (i.e., a specificity to phosphorylate) serine/threonine residues, tyrosine residues, or both serine/threonine and tyrosine residues, e.g. the dual specificity kinases. Conserved structural motifs provide clear indication as to how the kinases transfer the γ-phosphate of a purine nucleotide triphosphate to the hydroxyl groups of protein substrates. The kinase domains that define protein kinases contain 12 conserved subdomains (I-XII) that fold into a common catalytic core structure, as revealed by the 3-dimensional structures of several kinases. The central core of the catalytic domain, the region with greatest frequency of highly conserved residues, consists of subdomains VI through IX. As referred to herein, protein kinases include a kinase catalytic domain of about 20-400 amino acid residues in length, about 50-300 amino acid residues in length, about 100-300 amino acid residues in length, about 200-300 amino acid residues in length or about 250-300 amino acid residues in length. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) Science 241, 42-52, the contents of which are incorporated herein by reference).

Protein kinases that have closely related catalytic domains define families and represent products of genes that have undergone relatively recent evolutionary divergence. Clustering appears to be of predictive value in the determination of the properties and function of novel protein kinases. Accordingly, members of a given family tend also to share related functions. This is manifested by similarities in overall structural topology, mode of regulation, and substrate specificity (see, generally, Hardie, D. G., et al. (1995) The Protein Kinase Factsbook, Academic Press, London).

The complete repertoire of human kinases can be subdivided into "families", according to a dendrogram-based organization of human kinases, e.g. as shown in Manning et al. (2002) Science 298: 1912-1919, which are distinguished from each other according to sequence comparison of kinase catalytic domains, comparison of sequence and protein structures outside of the catalytic domains, known biological functions, and classification of kinases in other species. The following are exemplary kinase families: A6, ABC1, Abl, Ack, AKT, Alk, Alpha, AUR, Axl, BCR, BRD, BUB, Bud32, CAMK1, CAMK2, CAMKK, CAMKL, CAMK-Unique, CASK, CCK4, CDC7, CDK, CDKL, CK1, CK2, CLK, Csk, DAPK, DCAMKL, DDR, DMPK, DYRK, EGFR, Eph, Fak, FAST, Fer, FGFR, G11, GRK, GSK, H11, Haspin, IKK, InsR, IRAK, IRE, JakA, JakB, LISK, Lmr, LRRK, MAPK, MAPKAPK, MAST, Met, MLCK, MLK, MOS, Musk, NAK, NDR, NEK, NKF1, NKF2, NKF3, NKF4, NKF5, NRBP, Other-Unique, PDFGR, PDHK, PEK, PHK, PIKK, PIM, PKA, PKB, PKC, PKD, PKG, PKN, PLK, PSK, RAD53, RAF, RCK, Ret, RGC, RIO, RIPK, Ror, RSK, RSKb, RSKL, Ryk, SCY1, Sev, SGK, Slob, Src, SRPK, STE11, STE20, STE7, STE-Unique, STKR, Syk, TAF1, TBCK, Tec, Tie, TIF1, TKL-Unique, TYK-Unique, TLK, TOPK, Trbl, Trio, Trk, TSSK, TTBK, TTK, ULK, VEGFR, VPS15, VRK, WEE, Wnk, YANK, sphingosine kinases (SKs), diacylglycerol kinases (DGKs), ceramide kinases (CKs), 1-acyl-glycerol kinases, phosphatidylinositol-phosphate kinases, carbohydrate kinases, lipid kinases, nucleotide kinases, and urokinases.

In one embodiment, a regulatable protein comprises, consists essentially of, or consists of a kinase or kinase related protein in Table 1. A regulatable protein may also be a kinase or kinase related protein that is not listed in Table 1. A regulatable protein may also be an orthologue of a protein in Table 1 or other kinase or kinase related protein, e.g., a non-human orthologue, such as a mammalian, vertebrate, ovine, bovine, equine, feline, canine, mouse, or other orthologue. Regulatable proteins may be components of the same biological pathway or of different biological pathways.

In certain embodiments, a composition comprises one or more regulatable proteins or nucleic acids encoding such, wherein at least some of the regulatable proteins are kinases or kinase related proteins with the proviso that the proteins are not specific proteins, e.g., proteins known in the art to have been linked to a regulatory signal. In certain embodiments, one or more nucleic acids encode one or more regulatable proteins, e.g., kinases or kinase related proteins, with the proviso that the protein is not of a specific family of kinases, e.g., one of the families further described herein.

A regulatable protein may also be a fragment of a naturally occurring regulatable protein, e.g., a kinase or kinase related protein. A fragment may be a biologically active fragment, such as a fragment that retains the catalytic activity of the protein, e.g., the ability to phosphorylate a target protein. For example, a regulatable protein may be a protein that comprises, consists essentially of, or consists of a catalytic kinase domain, such as those further described herein. A fragment may comprise more than one conserved domain, e.g., a catalytic domain and a protein-protein interaction domain, an extracellular ligand binding domain, and/or a transmembrane domain of a receptor kinases. A fragment may also comprise a catalytic kinase domain and about 1, 2, 3, 4, 5, 10, 15, 20, or 50 or more consecutive amino acids on the N- or C-terminus. A fragment may also comprise a full length naturally occurring regulatable protein lacking 1, 2, 3, 4, 5, 10, 15, 20, or 50 or more amino acids at the N- or C-terminus. The term "regulatable protein" includes full length regulatable protein, such as they occur in nature, or biologically active fragments thereof or homologs thereof, such as a protein that can be used in or more of the complementation assays described herein.

In one embodiment, a regulatable protein comprises, consists essentially of, or consists of an amino acid sequence that is at least about 70%, 80%, 90%, 95%, 98% or 99% identical to the amino acid sequence of a naturally-occurring kinase or kinase related protein, e.g., shown in Table 1, or a portion thereof. A regulatable protein may comprise an amino acid sequence that is at least about 70%, 80%, 90%, 95%, 98% or 99% identical to a kinase catalytic domain, e.g., present in one of the proteins of Table 1.

A regulatable protein may also be a protein that is encoded by a nucleic acid that is at least about 70%, 80%, 90%, 95%, 98% or 99% identical to a nucleotide sequence encoding a protein of Table 1 or other kinase or kinase related protein or fragment thereof, such as the nucleotide sequence that encodes the catalytic domain.

The term "percent identical" refers to sequence identity between two amino acid sequences or between two nucleotide sequences. Identity can be determined by comparing a position in each sequence, which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Regulatory proteins may also be encoded by nucleic acids that hybridize, e.g., under stringent hybridization conditions, to a nucleic acid encoding a protein in Table 1 or other kinase or kinase related protein or biologically active fragment thereof. Hybridization may be under high stringency conditions of 0.2 to 1×SSC at 65° C. followed by a wash at 0.2×SSC at 65° C. Regulatory proteins may also be encoded by nucleic acids that hybridize under low stringency conditions of 6×SSC at room temperature followed by a wash at 2×SSC at room temperature to a nucleic acid encoding a protein in Table 1 or other kinase or kinase related protein or biologically active fragment thereof. Other hybridization conditions include 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays," Elsevier, N.Y. provide a basic guide to nucleic acid hybridization.

The present invention also provides for analogs of naturally occurring regulatable proteins, such as those in Table 1. Analogs can differ from naturally occurring proteins by conservative amino acid sequence differences or by modifications which do not affect sequence, or by both. Any number of procedures may be used for the generation of mutant, derivative or variant forms of regulatable proteins using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

For example, conservative amino acid changes may be made, which although they alter the primary sequence of a protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine (in positions other than proteolytic enzyme recognition sites); phenylalanine, tyrosine.

Other variants of naturally occurring regulatable proteins are those that differ from the naturally-occurring protein in 1, 2, 3, 4, 5, 10, 20, 50 or more amino acid substitutions, deletions or additions. The substitutions may be conservative substitutions or non-conservative substitutions. Guidance in determining which amino acid residues may be substituted, inserted, or deleted without abolishing biological activity may be found using computer programs well known in the art, for example, LASERGENE software (DNASTAR).

A regulatable protein may also differ from a naturally occurring regulatable protein, e.g., a protein in Table 1, by the addition of 1, 2, 3, 4, 5, 10, 20, 50 or more consecutive amino acids having a sequence that is unrelated to, or not part of (e.g., heterologous to), the sequence of the naturally occurring regulatable protein. In one embodiment, a regulatable protein is a biologically active fragment of a naturally occurring regulatable protein to which 1, 2, 3, 4, 5, 10, 20, 50 or more consecutive amino acids are added to the N- and/or C-terminus of the protein, which consecutive amino acids form an amino acid sequence that is not present at the same place in the naturally occurring regulatable protein.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified by, for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

Peptides and proteins may also comprise one or more non-naturally occurring amino acids. For example, nonclassical amino acids or chemical amino acid analogs can be introduced as a substitution or addition into peptides. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general.

Also provided are derivatives of regulatable proteins, such as chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

Moreover, mimetopes of the subject peptides and proteins can be provided. Peptidomimetics can have such attributes as being non-hydrolyzable (e.g., increased stability against proteases or other physiological conditions which degrade the corresponding peptide). For illustrative purposes, peptide analogs can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988, p123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, L, 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modified (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988).

Additionally, peptidomimetics based on more substantial modifications of the backbone of a peptide can be used. Peptidomimetics which fall in this category include (i) retro-inverso analogs, and (ii) N-alkyl glycine analogs (so-called peptoids).

In addition to a variety of side chain replacements which can be carried out to generate peptidomimetics, the description specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Peptides may comprise at least one amino acid or every amino acid that is a D stereoisomer. Other peptides may comprise at least one amino acid that is reversed. The amino acid that is reversed may be a D stereoisomer. Every amino acid of a peptide may be reversed and/or every amino acid may be a D stereoisomer.

In another illustrative embodiment, a peptidomimetic can be derived as a retro-enantio analog of a peptide. Retro-enantio analogs such as this can be synthesized with commercially available D-amino acids (or analogs thereof) and standard solid- or solution-phase peptide-synthesis techniques, as described, e.g., in WO 00/01720. The final product may be purified by HPLC to yield the pure retro-enantio analog.

Also included are peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

Modifications that do not normally alter primary sequence include in vivo or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are proteins which have phosphorylated amino acid residues, e.g., phosphotyrosine, phosphoserine, or phosphothreonine.

A skilled artisan will readily understand that the nucleotide sequences encoding proteins with specific cellular activities or the proteins themselves may be modified in a number of ways as to make the proteins regulatable such that said cellular activities can be activated or inactivated independent of natural cellular regulatory mechanisms.

In one embodiment, a regulatable protein is linked to a regulatory signal. A "regulatory signal" is a protein domain, which when linked to a regulatory protein, causes the regulatory protein to exhibit at least some of the biological activity of the corresponding wild type or naturally occurring protein in the absence of regulation by its natural factors. A regulatory signal can be an activation signal or a repression signal. An activation signal is a protein domain, which when linked to a regulatory protein, causes the regulatory protein to exhibit at least some of the biological activity of the corresponding wild type or naturally occurring protein in the absence of activation by its natural factors. A regulatory domain may be linked to the N-terminus or C-terminus of a regulatable protein or it can be located internally to the regulatable protein. It can be linked directly or indirectly, e.g., through 1, 2, 3, 4, 5, 6, 7, 8, 9, 10 or more consecutive amino acids, which may be unrelated in sequence to the regulatable protein or the regulatory signal.

In one embodiment, a regulatory protein is a protein that is active as a result of a modification, such as a modification that allows the protein to oligomerize or to be targeted to a particular compartment in a cell, e.g., the cell membrane. Linking the regulatory protein to a regulatory signal will regulate, i.e., activate or repress, the protein, either, constitutively or inducibly. Its activity may be similar to, higher or lower relative to the naturally occurring corresponding regulatable protein. For example, a regulatable protein may be a kinase that is activated by being targeted to the cell membrane and/or by dimerization, events that will happen naturally in a cell under certain circumstances. Linking a kinase to a domain that will target it to the cell membrane or allow it to dimerize will allow the kinase to be active independently of whether the specific circumstances that usually activate kinase are present.

In one embodiment, a regulatable protein, e.g., a kinase, is constitutively regulated, e.g., activated, by linking it to one or more of the following domains/signals: an oligomerization domain, a cellular membrane localizing signal, or a signal for covalent binding of lipid groups.

In one embodiment, a regulatable protein is linked to an activation signal that allows its trafficking and insertion into cellular membranes. Additionally, the signal may be a novel sequence created, for example, from all or part of two or more different signals. In one, embodiment, a regulatable protein is linked to an activation signal allowing it to be covalently modified by lipid groups. Such lipid groups that can be covalently attached include, but are not limited to, fatty acids, isoprenoids and glycosylphosphatidylinositol (GPI) anchors, either alone or in combinations thereof. Various proteins involved in signal transduction have been shown to be fatty-acylated (Johnson et al. (1994) *Ann. Rev. Biochem.* 63, 869-914) and this modification has been demonstrated to be sufficient for the constitutive activation of many kinases, including PI3K p110α subunit and AKT (Klippel et al. (1996) *Mol. Cell. Biol.* 16, 4117-4127; Kohn et al. (1996) *J. Biol. Chem.* 271, 21920-21926).

In one embodiment, fatty acids will contain from between about 1 to 100 carbons or between about 12 to 24 carbons. In another embodiment, fatty acylation involves the covalent attachment of the 14-carbon saturated fatty acid myristate (myristoylation) by either N-myristoyltransferase 1 (NMT-1) or NMT-2 or the 16-carbon fatty acid palmitate (palmitoylation) to a regulatable protein. These regulatable proteins may be modified by myristate or palmitate, either alone or in combinations thereof. Myristoylated proteins include the α subunit of some heterotrimeric G proteins, cAMP-dependent protein kinase, Src, myristoylated protein kinase C substrate (MARCKS) protein and numerous retroviral coat proteins. Through analysis of amino acid sequence variability of known myristoylated substrate proteins, binding site analyses in X-ray structures or 3D homology models for NMTs from various taxa, and on kinetic data, a refinement of the motif for N-terminal (glycine) myristoylation has been accomplished (Maurer-Stroh et al. (2002) *J. Mol. Biol.* 317, 541-557). In one embodiment, myristoylated regulatable proteins contain a canonical myristoylation motif (MGXXXS/T, where X is an intervening amino acid residue). Additional information regarding myristoylation motifs can be found in, e.g., Towler et al. (1988) *Ann. Rev. Biochem.* 57: 69-99. Exemplary myristoylation motifs that may be used includes MET GLY SER SER LYS SER LYS PRO LYS ASP PRO SER GLN ARG ARG ARG ARG ILE ARG GLY (SEQ ID NO: 2) from c-src.

It is understood that there are at least three motif regions present within the approximately 17 N-terminal residues of N-myristoylated proteins: region 1 (approximately positions 1-6) that fits the binding pocket of NMTs, region 2 (approximately positions 7-10) that interact with the NMT's surface at the mouth of the catalytic cavity and region 3 (approximately positions 11-17) comprising a hydrophilic linker. In another embodiment, these residues, or the nucleotides that encode them, can be modified according to known structure-function relationships to generate signals that will result in myristoylation of a given protein (e.g., Maurer-Stroh et al. (2002) *J. Mol. Biol.* 317, 541-557). Proteins can also be fatty acylated with palmitoyl moieties linked through thioester bonds to one or more cysteine residues. Because other medium- and long-chain fatty acids can also be attached to 'palmitoylated' proteins, the term S-acylation is often used. There is no consensus sequence for protein palmitoylation, although some modified sites can be predicted. In addition, all of these motifs or their variants may also be found at the C-terminus or at any other position within the protein to signal myristoylation. Examples of C-terminal and internal myristoylation signals are well known in the art. Various DNA sources known in the art can be used to clone and encode such sequences.

Proteins can also be lipidated by prenylation, a process involving protein modification of lipid anchors comprising isoprene units ($C_5$). In one embodiment, prenylation may involve protein modification of lipid anchors composed of between 1 and 20 isoprene units. In general, prenylation can be conveniently subdivided into three types: (1) Farnesylation generally involves the linkage of a farnesyl (15-carbon) group(s) to cysteine residues at or near the C terminus of proteins. One consensus target sequence for farnesylation is CAAX (where C is cysteine, A is an amino acid with a hydrophobic side chain and X is another amino acid). This sequence is recognized by farnesyltransferase (FT). Additionally, palmitoylation of cysteines close to the farnesylated cysteine occurs in some proteins. The farnesyl group is donated by farnesyl pyrophosphate, an intermediate in the sterol biosynthetic pathway. The enzymology of farnesylation and its associated modifications appears to have been conserved in eukaryotes. These processes occur in both mammalian cells and in the budding yeast, *S. cerevisiae*. Farnesylated proteins include G subunits of some heterotrimeric G proteins, ras proteins and the nuclear lamins. For example, it is well known in the art that it is possible to fuse the last eleven amino acids of a ras protein to a given protein and confer membrane association upon that protein. (2) Geranylgeranylation generally involves the addition of a geranylgeranyl (20-carbon) group(s) to the cysteine residues at or near the C terminus of proteins. One consensus target sequence for geranylgeranylation is CAAX, where A is preferably an aliphatic amino acid and X is preferably L, F, I, V or M. The enzyme which performs this type of geranylgeranylation is geranylgeranyl transferase I (GGT1), which contains a subunit that is common to farnesyl transferase. Proteins that undergo this modification include several ras-related G proteins, such as rac1; rac2 and ra1A and the G subunits of some heterotrimeric G proteins. (3) Geranylgeranylation can also be effected by geranylgeranyl transferase II (GGT2), which recognizes a variety of C terminal motifs. Examples of known C-terminal motifs include, but are not limited to, -CC, -CXC, -CCX, -CCXX, -CCXXX, and -CXXX (where C is cysteine and X is another amino acid). GGT2 appears to be especially important for geranylgeranylation of Rab proteins, a large subgroup of Ras-related GTPases involved in vesicular trafficking. Through analysis of amino acid sequence variability of known substrates for FT, GGT1 and GGT2 and evolutionary motif conservation, a refinement of the motif for recognition by these enzymes has been accomplished (Maurer-Stroh and Eisenhaber (2005) *Genome Biol.* 6, R55) and it has been determined that the motifs recognized by these enzymes is more flexible than recognition of the canonical 'CAAX' box. In one embodiment, these flexible amino acid motifs, or the nucleotides that encode them, can be modified according to known structure-function relationships to generate signals that will result in either farnesylation or geranylgeranylation of a given protein (e.g., Maurer-Stroh and Eisenhaber (2005) *Genome Biol.* 6, R55). In addition, all of these motifs or their variants may also be found at the N-terminus or at any other position within the protein to signal prenylation. Examples of N-terminal and internal prenylation signals are well known in the art. Various DNA sources known in the art can be used to clone and encode such sequences.

Proteins can also be lipidated by post-translational addition of glycosylphosphatidylinositol (GPI) anchors and this process generally involves a transamidation reaction in which a GPI moiety is attached at or near the C-terminus of a polypeptide in the endoplasmic reticulum. In general, the GPI signal sequence consists of a triplet of small amino acids (termed ω, ω+1, and ω+2 in the art), a hydrophilic spacer sequence of 7-10 amino acids, and a C-terminal hydrophobic stretch. The ω amino acid constitutes the site of GPI attachment and this attachment is catalyzed by GPI transamidase (GPIT). Through analysis of amino acid sequence variability of known GPI-modified proteins and site-directed mutant information, a refinement of the motif signal required for GPI-modification has been accomplished (Eisenhaber et al. (2001) *Protein Eng.* 14, 17-25 and references therein). In one embodiment, the amino acid motif signals, or the nucleotides that encode them, can be modified according to known structure-function relationships to generate signals that will result in GPI-modification of a given protein (e.g., Eisenhaber et al. (2001) *Protein Eng.* 14, 17-25 and references therein). In addition, all of these motifs or their variants may also be found at the N-terminus or at any other position within the protein to signal GPI modification. Examples of N-terminal and internal GPI signals are well known in the art. Various DNA sources known in the art can be used to clone and encode such sequences.

In a specific embodiment, a regulatable protein is targeted to a membrane in an inducible fashion. Several inducible membrane targeting strategies for proteins are known. In one embodiment, a regulatable protein is linked to a FRAP rapamycin binding (FRB) domain or a variant thereof. This FRB-regulatable protein fusion protein can then be induced to heterodimerize in the presence of a small molecule, e.g., rapamycin or a rapamycin analog, with an FKBP domain or a variant of FKBP12 or its homolog. The FKBP domain(s) can be expressed at the membrane, for example, through linkage to a membrane targeting signal (e.g. myristoylation moiety) and will thus effect inducible membrane targeting of regulatable proteins upon exposure to said small molecule (e.g., Li et al (2002) *Gene Therapy* 9, 233-244). The basic FRB-rapamycin-FKBP strategy, especially as applied in mammalian cells, has been extensively described in the art (e.g. Rivera (1998) *Methods* 14: 421-429 and Pollock and Rivera (1999) *Methods Enzymol.* 306: 263-281). Alternatively, a regulatable protein can be fused to an FKBP domain or a variant thereof that can be induced to heterodimerize in the presence of a small molecule, e.g., rapamycin or a rapamycin analog, with an FRB domain or a variant thereof from FKBP12 or its homolog such that expression of a membrane bound FRB domain, effected through linkage to a membrane targeting signal (e.g. myristoylation moiety), will effect membrane targeting of the regulatable protein. Membrane targeting of regulatable proteins can be controlled by the availability of the small molecule, rapamycin, or its derivatives.

A skilled artisan will appreciate that stable membrane binding of proteins post-translationally modified for membrane localization may be enhanced by the addition of one or more membrane targeting modifications. For example, membrane binding of the Src kinase is mediated by an N-terminal myristoylation in addition to a polybasic residue domain (Sigal et al. (1994) *Proc. Natl. Acad. Sci. USA* 91, 12253-12257).

An activation signal may also comprise, consist essentially of or consist of a dimerization or oligomerization domain that allows homo- and hetero-dimerization or oligomerization of a regulatable protein with itself or with additional regulatable proteins. Homodimerization and homo-oligomerization refer to the association of like components to form dimers or oligomers. Heterodimerization and hetero-oligomerization refer to the association of dissimilar components to form dimers or oligomers. Homo-oligomers thus comprise an association of multiple copies of a particular components, while hetero-oligomers comprise an association of copies of different components. "Oligomerization", "oligomerize" and "oligomer", with or without prefixes, are intended to encompass "dimerization", "dimerize" and "dimer". Oligomerization brings the action domains of the encompassed components into close proximity with one another thus triggering cellular processes normally associated with the respective action domain, such as kinase-mediated signal transduction. Numerous examples in the literature indicate that naturally occurring mutations resulting in oligomerization of both receptor and non-receptor protein kinases can cause cellular transformation (e.g., Monaco et al. (2001) *Oncogene* 20, 599-608 and Fan et al. (2003) *Cancer Res.* 63, 873-877). An oligomerization domain can be linked to the N-terminus, C-terminus or internally to the regulatable protein. Oligomerization may be enhanced by the addition of two or more oligomerization domains. Regarding kinases, such oligomerization domains may replace or be used in conjunction with membrane localizing domains in order to activate or enhance the activity of kinases whose activities are influenced by dimerization and which are minimally or completely nonresponsive to membrane localization.

In general, dimerization and oligomerization domains can be conveniently subdivided into two types: (1) domains whose associations are constitutive and (2) domains whose associations are regulated. In general, domains whose associations are constitutive can be fused to regulatable proteins to allow heterologous homo- and hetero-dimerization or oligomerization in a constitutive manner upon expression. A skilled artisan will recognize that many heterologous domains whose associations are constitutive are well known in the art. Examples described in the art include, but are not limited to, heterodimerization of PDZ domains from the mammalian proteins neuronal nitric oxide synthase (nNOS) and syntrophin (Ung et al. (2001) *EMBO J.* 20: 3728-3737), heterodimerization of the *Xenopus* XLIM1 and LDB1 proteins (Ung et al. (2001) *EMBO J.* 20: 3728-3737), oligomerization of RFG (also named ELE1 or ARA70) through its coiled-coil domain (Monaco et al. (2001) *Oncogene* 20: 599-608), oligomerization of the leucine zipper domain of yeast GCN4 (Harbury et al. (1993) *Science* 262: 1401-1407), and oligomerization of the TEL helix-loop-helix (HLH) domain (Golub et al. (1996) *Mol. Cell. Biol.* 16, 4107-4116) and their variants. In one embodiment, the activation domain consists of the TEL protein or an oligomerization domain thereof, which is a member of the Ets family of transcription factors, or the helix-loop-helix (HLH) domain of TEL. An exemplary TEL sequence comprises the amino acid sequence (SEQ ID NO: 3)
MSETPAQCSIKQERISYTPPESPVPSYASSTPLHVPVPRALRMEEDSIRL

PAHLRLQPIYWSRDDVAQWLKWAENEFSLRPIDSNTFEMNGKALLLLTKE

DFRYRSPHSGDVLYELLQHILKQRKPRILFSPFFHPGNSIHTQPEVILHQ

NHEE.

TEL-kinase fusion proteins form HLH-dependent homo-oligomers in vitro, a process critical for constitutive tyrosine kinase phosphorylation, and hence, constitutive activation (Golub et al. (1996) *Mol. Cell. Biol.* 16, 4107-4116).

In general, oligomerization domains can be fused to regulatable proteins to allow heterologous homo- and heterodimerization or oligomerization in a regulated manner. A skilled artisan will recognize that many heterologous domains whose associations are regulated, rather than constitutive, are well known in the art. Examples include, but are not limited to, the Gyrase B-coumermycin system, the FKBP-rapamycin-FRAP system, and their variants. In general, these heterologous domains are domains from naturally occurring proteins or truncated active portions thereof. The binding domain can be small (<25 kDa to allow efficient transfection in viral vectors), nonimmunogenic and accessible to cell permeable, nontoxic ligands. In one embodiment, a regulatable protein is fused to bacterial Gyrase B polypeptide or a fragment or derivatives thereof (e.g. amino acids 1-220 of *E. coli* GyrB) that can be induced to dimerize in the presence of coumermycin or a coumermycin analog (Farrar et al. (1996) *Nature* 383, 178-181 and Farrar et al., U.S. Pat. No. 6,916, 846). In another embodiment, a regulatable protein is fused to the FRB (FRAP rapamycin binding) domain(s) or its variants of FRAP/mTOR or to an FKBP domain(s) or its variants of FKBP12 or its homologs, such that expression of a chimeric protein comprising the regulatable protein fused to the FRB domain and identical regulatory proteins or other regulatory proteins fused to FKBP, or vice versa, can dimerize in the presence of rapamycin or a rapamycin analog. In another embodiment, the linking ligand can have different receptor binding molecules with different epitopes to mediate oligomerization of chimeric proteins having the same or different binding domains. For example, the ligand may comprise rapamycin or a rapamycin-type moiety and a cyclosporinA or cyclosporin type moiety. Both moieties may be covalently attached to a common linker moiety. Such a ligand would be useful for mediating the oligomerization of a first and second chimeric protein where the first chimeric protein contains a receptor domain, such as an FKBP domain from FKBP12 or its homolog that is capable of binding to the rapamycin or rapamycin-type moiety, and the second chimeric protein contains a receptor domain, such as cyclophilin, that is capable of binding to the cyclosporin A or cyclosporin type moiety. A variety of pairs of synthetic ligands and ligand binding proteins or domains known in the art can be employed.

Detection and confirmation of protein-protein interactions resulting from dimerization or oligomerization can be accomplished in a number of manners well known in the art. These approaches generally employ the affinities between interacting proteins to isolate and analyze proteins in a bound state or the distance between interacting proteins. Examples of such methods include, but are not limited to, non-reducing SDS-PAGE, chromatography, density gradient densitometry, microscopy including transmission electron microscopy, mass spectrometry, immunoprecipitation employing dimerization- or oligomerization-specific antibodies, bioluminescence resonance energy transfer (BRET), fluorescence resonance energy transfer (FRET) and the like.

Also provided herein are compositions comprising one or more nucleic acids encoding at least 1, 2, 3, 4, 5, 10, 20, 50, 100, 500 or more inhibitory mutants of proteins, wherein expression of the inhibitory mutants in a cell downregulates one or more biological activities associated with the corresponding wild-type or naturally occurring proteins. In one embodiment, a composition may comprise a library of nucleic acids encoding inhibitory mutant proteins, or pools of nucleic acids thereof (a "dead library"). A pool of nucleic acids may encode about 5-10, 10-20, 10-30 or more inhibitory mutants.

In one embodiment, each inhibitory mutant is encoded by a separate nucleic acid. For example, a composition may comprise at least about 1, 2, 3, 4, 5, 10, 20, 50, 100, 200, 300, or 500 nucleic acids, wherein each nucleic acid encodes one inhibitory mutant. As further discussed below, the nucleic acids do not need to be in one composition. In particular, each member of a library of nucleic acids may be physically separated from the other members, e.g., by being present in a well of a multiwell plate. In one embodiment, each member of a library of nucleic acids encoding inhibitory mutants is present in a separate well from the other nucleic acids of the library.

Also provided herein are compositions comprising one or more inhibitory mutants. A composition can comprise at least about 1, 2, 3, 4, 5, 10, 20, 50, 100 or more proteins. A composition may comprise a library of inhibitory mutants or pools of proteins thereof. A pool of proteins may comprise about 5-10, 10-20, 10-30 or more proteins. The members of the library do not need to be in a composition. Each member of the library may be in a separate vial or well of a multiwell dish.

An inhibitory mutant may be a mutant of a protein involved in signal transduction, e.g., a kinase or a phosphatase. An inhibitory mutant may be a dominant negative mutant, a deletion mutant, a mutant comprising one or more substitution or addition of amino acids.

In one embodiment, a protein, e.g., a kinase, in a cell is inactivated by introducing into the cell an inhibitory mutant of the protein, such that the inhibitory mutant downregulates one or more biological activities associated with the corresponding wild-type protein. Such mutants can be generated by the following, but are not limited to, mutation, deletion, modification or rearrangement of nucleotide sequences that encode domains used to define the protein family with which the protein is associated (e.g. the kinase domain of kinase proteins), regulatory elements, protein-protein interaction domains, residues that are targets of cell signaling (e.g. phosphorylation), protein degradation signal domains and cellular localization domains. In one embodiment, these inhibitory mutants are dominant negative mutants. As used herein, a dominant negative mutant is a mutant polypeptide which, when expressed, disrupts the activity of the wild type protein. It may act by binding to the active protein and rendering it inactive or inhibited, or where it is an enzyme, by binding the target protein without enzymatically activating the protein, thus blocking and preventing, the active enzymes from binding and activating the target protein. A dominant negative protein is encoded by a dominant negative gene, which is itself derived from a change with regard to at least one position in its sequence relative to the corresponding wild type version of the gene. A dominant negative gene encodes a product that disrupts an endogenous genetic process of a host cell which expresses the gene and that is effective in a single copy or may produce an effect due to overexpression of the gene either by increased production of the gene product, or by coexpression of multiple copies of the gene. In one embodiment, a change can occur due to alternative splicing of gene products, which have lost an important site or domain, and thus become enzymatically inactive or inhibited. In another embodiment a change can occur at a position that encodes a changed amino acid residue position at an active site required for biological and/or pharmacological activity in the native peptide, as can happen, for example, due to amino acid alterations in residues critical for catalytic function of kinase domains. Such critical regions are described in the art, as in Hanks et al. (1988) *Science* 241, 42-52. In yet another embodiment, the dominant negative mutants are the result of substitutions in one or more amino acids that causes a change in posttranslational modification of the protein (e.g. a change in acetylation, glycosylation, phosphorylation, ubiquitination, alkylation, glutamylation, acylation, isoprenylation, lipoylation, phosphopantetheinylation, sulfation, selenation, or C-terminal amidation). These inhibitory proteins are said to be "constitutively regulated" because they do not exhibit specific activity despite potential stimulation by natural factors and do not produce any of the cellular responses normally induced by said natural factors even with potential stimulation by these natural factors.

Also provided herein are compositions comprising one or more nucleic acids comprising or capable of expressing at least 1; 2, 3, 4, 5, 10, 20, 50, 100, 500 or more small nucleic acids or antisense oligonucleotides or derivatives thereof, wherein said small nucleic acids or antisense oligonucleotides or derivatives thereof in a cell specifically hybridize (e.g., bind) under cellular conditions, with small nucleic acids (e.g., small RNAs and microRNAs), with cellular mRNA and/or genomic DNA encoding one or more cellular proteins. In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 5-10, 10-20-, 10-30 or more nucleic acids comprising or capable of expressing small nucleic acids or antisense oligonucleotides or derivatives thereof.

In one embodiment, each small nucleic acid or antisense oligonucleotide or derivative thereof is generated by a separate nucleic acid. For example, a composition may comprise at least about 1, 2, 3, 4, 5, 10, 20, 50, 100, 200, 300, or 500 nucleic acids, wherein each nucleic acid generates a small nucleic acid or antisense oligonucleotide or derivative thereof. As further discussed below, the nucleic acids do not need to be in one composition. In particular, each member of a library of nucleic acids may be physically separated from the other members, e.g., by being present in a well of a multiwell plate. In one embodiment, each member of a library of nucleic acids that generate a small nucleic acid or antisense oligonucleotide or derivative thereof is present in a separate well from the other nucleic acids of the library. Such nucleic acids may be used alone or in combinations with regulatable proteins and/or inactive mutants described herein.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

Small nucleic acids and/or antisense constructs of the methods and compositions presented herein can be delivered, for example, as an expression plasmid which, when transcribed in the cell, produces RNA which is complementary to at least a unique portion of cellular nucleic acids (e.g., small RNAs; mRNA, and/or genomic DNA). Alternatively, Small nucleic acids and/or antisense constructs are oligonucleotide probes that are generated ex vivo and which, when introduced into the cell, results in hybridization with cellular nucleic acids (e.g., small RNAs, mRNA, and/or genomic DNA). Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., small RNAs, mRNA, and/or genomic DNA). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon; should work most efficiently at inhibiting translation. However, sequences complementary to the 3' untranslated sequences of mRNAs have recently been shown to be effective at inhibiting translation of mRNAs as well. (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and nonspecific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215:327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports. (Sarin et al. (1988) Proc. Natl. Acad. Sci. U.S.A. 85:7448-7451), etc.

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. In vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. Nature 2001; 411(6836):494-8). Accordingly, translation of a gene in a cell can be inhibited by contacting the cell with short doublestranded RNAs having a length of about 15 to 30 nucleotides or of about 18 to 21 nucleotides or of about 19 to 21 nucleotides. Alternatively, a vector encoding for such siRNAs or hairpin RNAs that are metabolized into siRNAs can be introduced into a target cell (see, e.g., McManus et al. (2002) RNA 8:842, Xia et al. (2002) Nature Biotechnology 20:1006; and Brummelkamp et al. (2002) Science 296:550. Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247: 1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.) and should be delivered to cells which express Foxo genes in vivo. A preferred method of delivery involves using a DNA construct "encoding" the ribozyme under the control of a strong constitutive pol HI or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Small nucleic acids, antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that regulatable proteins, inhibitory mutants, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

Regulatable proteins and inhibitory mutants, e.g., as described herein, may be encoded by one or more nucleic acids or variants thereof. Small nucleic acids and antisense oligonucleotides can comprise or be expressed by one or more nucleic acids or variants thereof. The terms "polynucleotide" and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semisynthetic, or synthetic origin which either does not occur in nature or is linked to another polynucleotide in a nonnatural arrangement. The term "oligonucleotide" may be used to refer to a single stranded polynucleotide having less than about 100 nucleotides, less than about, e.g, 75, 50, 25, or 10 nucleotides.

Nucleic acids described herein may also be variants, e.g., variants of those in Table 1. The term "variant," when used in the context of a polynucleotide sequence, may encompass a polynucleotide sequence related to that of a particular gene or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variation is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

A nucleic acid that encodes a protein described herein may be linked to a regulatory element, e.g., a promoter, enhancer, silencer, and termination signal, as further described herein.

One of skill in the art will readily understand that the proteins described herein can be expressed by expression vectors harboring nucleic acids that encode these proteins and that these expression vectors may be modified in a number of ways. The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide. In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto. Appropriate vectors may be introduced into host cells using well known techniques, such as infection, transduction, transfection, transvection, electroporation and transformation and accompanying reagents typically used to introduce the compositions into a cell. Generally, a plasmid vector is introduced in a precipitate, such as a calcium phosphate precipitate, or in a complex with a charged lipid. If the vector is a virus, it may be packaged in vitro using an appropriate packaging cell line and then transduced into cells. In one embodiment, the vector may be, for example, a phage, plasmid, viral or retroviral. Exemplary viral and retroviral vectors include adenovirus vectors, adeno-associated virus vectors, lentivirus vectors, herpes simplex virus (HSV) vectors, human immunodeficiency virus (HIV) vectors, bovine immunodeficiency virus (BIV), murine leukemia virus (MLV), and the like. Retroviral vectors may be replication competent or replication defective. In the latter case, viral propagation generally will occur only in complementing host cells. In a preferred embodiment, the vector is a recombinant retroviral vector. A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. Recombinant retroviruses and various uses thereof have been described in numerous references including, for example, Mann et al., Cell 33: 153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from Moloney murine leukemia virus, e.g., Morgenstern and Land, Nucleic Acids Res. 18:3587-3596, 1990, herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth, Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses.

Modifications may include individual nucleotide substitutions to a constitutively regulated vector or insertions or deletions of one or more nucleotides in the vector sequences. Modifications or operable linkages to a constitutively regulated vector that alter (i.e., increase or decrease) expression of a sequence interval (e.g., alternative promoters), provide greater cloning flexibility (e.g. alternative multiple cloning sites), provide greater experimental efficiency (e.g. alternative reporter genes), and/or increase vector stability are contemplated herein.

In one embodiment, an expression vector of the invention may be modified to replace a Gateway® cloning cassette with a multi-cloning sequence, containing restriction enzyme sites for insertion of potential enhancers through standard ligation.

A "promoter" herein refers to a DNA sequence recognized by the synthetic machinery of the cell required to initiate the specific transcription of a gene. In another embodiment, an expression vector of the invention may be modified to eliminate the strong CMV promoter sequence, to allow testing of an enhancer-promoter combination, including the endogenous gene promoter, inducible promoter, cell type-specific promoter, minimal promoter or other alternative enhancer-promoter sequences known to the skilled artisan. It is also known that many proteins, e.g., kinases, can be activated simply by being overexpressed in a given cell. In one embodiment, the strong CMV promoter sequence can be replaced with an even stronger promoter or coupled with an improved enhancer or the like in order to cause increased expression of wild type or regulatable proteins. In another embodiment, increased expression of wild type or regulatable proteins can be effected through coexpression of multiple copies of the gene with standard promoters.

In one embodiment, an expression vector will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

In one embodiment, a vector of the invention may be modified to include reporter genes, including genes encoding fluorescent proteins or enzymes, such as β-galactosidase and alkaline phosphatase. In certain embodiments, fluorescent reporters may be replaced with alternate fluorescent reporters with shorter or longer protein half-life allowing more precise evaluation of the timing of regulatory control. A reporter may also be replaced by cassettes encoding protein substrates that allow observation (direct or indirect) of response based on cell/biochemical activity, e.g., in screens of chemical libraries to identify potential therapeutic chemical targets/leads.

In one embodiment, an expression vector can include at least one selectable marker. Such markers include dihydrofolate reductase, neomycin or puromycin resistance for eukaryotic cell culture and tetracycline, kanamycin, or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Sf9 cells; animal cells such as CHO, COS and Bowes melanoma cells; and plant cells. Appropriate culture mediums and conditions for the above-described host cells are known in the art.

Nucleic acids or proteins described herein may be present in one or more compositions. For example, nucleic acids or proteins may be present in wells of a multiwell plate or in individual tubes or devices. They may also be present, e.g., linked, to a solid surface. Accordingly, also provided herein are devices comprising a location, wherein the location comprises one or more nucleic acids described herein, e.g., a nucleic acid encoding a regulatable protein linked to one or more regulatory signals, wherein expression of the regulatable proteins in a cell results in the regulatable protein or biologically active portion thereof being constitutively regulated.

Also provided herein are cells comprising one or more proteins, e.g., regulatable proteins linked to one or more regulatory signals or inhibitory mutants, or nucleic acid encoding these. A cell may be an isolated cell or it may be a cell that is part of a tissue or an organism. A cell may be a eukaryotic or a prokaryotic cell. A eukaryotic cell may be a human or a non-human mammalian or vertebrate cell, e.g., a simian, ovine, bovine, equine, porcine, canine, feline, rat or mouse cell. A prokaryotic cell may be a bacterial cell. Cells may comprise one or more nucleic acids or proteins. Exemplary cells are further described herein.

Further provided are methods comprising contacting a cell with a nucleic acid or a protein described herein. Contacting may be under conditions in which the nucleic acid or protein is taken up by the cell. For example, a cell may be contacted with a nucleic acid, or a pool of nucleic acids, under conditions resulting in transient transfection, in which the nucleic acids are essentially not integrated into the genome of the cell. Nucleic acids may also be contacted with a cell under conditions for stable transfection, resulting in one or more nucleic acids being integrated into the genome of the cell or in the form of an episome. The presence of an introduced nucleic acid or a protein in a cell can be determined according to methods known in the art.

II. Kits

Also provided herein are kits comprising one or more nucleic acids described herein, e.g., encoding a regulatable protein linked to one or more regulatory signals, wherein expression of the regulatable proteins in a cell results in the regulatable protein or biologically active portion thereof being constitutively regulated and packaging for said kit. Said kit may comprise one or more reagents necessary to express the regulatable proteins. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g. green fluorescent protein and beta-galactosidase), proteins not classified in any pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

III. Exemplary Assays

Provided herein are cell-based assays for identifying genes that are involved in causing cellular transformation or protecting against cellular transformation. A method may comprise contacting one or more cells with a nucleic acid or protein described herein. The method may further comprise determining whether a characteristic of the cells has changed.

In one embodiment, a method comprises providing a cell that is not transformed and introducing into the cell one or more regulatable proteins linked to one or more regulatory signals or one or more nucleic acids encoding such. The method may further comprise determining whether the cell is transformed. In an illustrative embodiment, a pool of nucleic acids encoding about 10-100 regulatable proteins each linked to one or more regulatory signals is introduced into cells that are not transformed. The cells are cultured under conditions that allow the nucleic acids to express the encoded proteins and then the method comprises determining whether the cells have been transformed as a result of the presence and expression of the nucleic acids. If the cells have been transformed, the nucleic acids are divided into subpools, e.g., of about 10-20 nucleic acids, and these are introduced into the same or other non-transformed cells such that the encoded proteins are expressed. The method then comprises determining again whether the cells have been transformed. If the cells have been transformed, it indicates that one or more nucleic acids encodes a protein that has transforming capacity. The nucleic acids can then progressively combined into smaller pools and introduced into cell and the above-described steps are reiterated until the nucleic acid that causes the cell to become transformed has been identified. The regulatable protein encoded by the nucleic acid can be identified using well known techniques.

In one embodiment, members of the regulatable protein library are administered in pools to determine whether any individual species within the set of pooled species is capable of altering characteristics of cellular transformation and/or tumorigenesis. In order to determine the identity of the effective species from each pool capable of altering characteristics of cellular transformation and/or tumorigenesis, transient expression or stable cell lines expressing individual species from each pool can be generated and analyzed for the ability to alter characteristics of cellular transformation and/or tumorigenesis. In a another embodiment, pools consisting of about 1-2, 1-5, 1-10, 1-20, 1-30, 1-40, 1-50, 1-100, 1-150, 1-300, 1-600 or 1-1200 unique regulatable proteins are contacted simultaneously with cells. In another embodiment, pools may be divided according to a dendrogram-based organization of human kinases as described, for example, by Manning et al. (2002) *Science* 298: 1912-1919. One of skill in the art may expect to identify some regulatable proteins that will induce alterations in characteristics of cellular transformation in any cell type and others that display cell type-specificity with regard to such alterations.

The methods may also employ any of a variety of non-transformed cells. A cell may be immortalized or not immortalized. In one embodiment, a cell is an immortalized cell that contains one or more genetic modifications that leads the cell to the path of being transformed, without, however, transforming it. For example, a cell may comprise 1, 2, 3 or more oncogenes but be only partially transformed, such that upon the addition of one more oncogene, the cell becomes transformed. Cells that are transformed but for the presence of one or more other genes or oncogenes are referred to herein as "quasi-transformed." In one example, a cell comprises one or more of the following genes and oncogenes or proteins: the catalytic subunit of telomerase (hTERT), telomerase, human papilloma virus E6, Human papilloma virus E7, cyclin D1, an R24C form of CDK4 ($CDK4^{R24C}$), p53DD, MYC, phosphatidylinositol-3-kinase, adenovirus early region 1A (E1A), E6, E7, MDM2, SV40 large T antigen, SV40 small T antigen, RAC/RHO, PI3K, AKT, RAF, MEK, MEKDD, MAPK, RAL-GEFs, RAL, PLD1, H-RAS, an activated allele of H-RAS (H-$RAS^{V12}$), ALT, CycD1/CDK4, or variants or fragments thereof that may be oncogenic or other such genes known in the art (see, e.g., Zhao et al., Trends Mol. Med., 10:344-350, 2004; Hunter, Cell, 64:249-270, 1991; and references incorporated therein). As shown in the Examples, a quasi-transformed cell may comprise hTERT, SV40 large T antigen and SV40 small T antigen. Other cells are those in which one or more tumor suppressor genes are inhibited or inactivated. A cell may have, for example, an inhibited or inactivated copy of p53, retinoblastoma (Rb), PP2A, p19ARF, $p16^{INK4A}$ or PTEN tumor suppressor genes or proteins or variants or fragments thereof that may be tumor resppressors or other such genes known in the art (see, e.g., Zhao et al., Trends Mol. Med., 10:344-350, 2004; Hunter, Cell, 64:249-270, 1991; and references incorporated therein). Quasi-transformed cells may also comprise a combination of one or more oncogenes and one or more inactivated tumor suppressor genes. Thus, in some embodiments, cells express, although not limited to, c-myc, H-RAS, hTERT individually or together with loss of function of the p53, retinoblastoma (RB) or PTEN tumor suppressor genes individually or in various combinations to cause transformation and/or tumorigenicity. Quasi-transformed cells can also be created by inactivating an oncogene or by activating inactivated tumor suppressor genes.

The quasi-transformed cell may be of human or non-human origin. Exemplary cells include human kidney epithelial (HEK) cells, human mammary epithelial cells (HMEC) and human prostate epithelial cells (HPEC). In one embodiment a quasi-transformed cell is an HEK cell comprising SV40 large and small T antigen and hTERT (HA1E cell). Other quasi-transformed cells are described in the Examples.

The principle of quasi-transformed cells is based at least on the following. Recent work indicates that a limited set of genetic changes can suffice to transform human cells (Hahn et al. (1999) *Nature* 436, 117-122). In one embodiment, the constitutive expression of the catalytic subunit of telomerase (hTERT) and the Large T (LT) and Small T (ST) oncoprotein of the SV40 Early Region (SV40ER) is sufficient to render a wide range of human cells transformed and/or tumorigenic, if supplied with an activated allele of H-RAS (H-$RASV^{12}$, H-RAS) (Zhao et al. (2004) *Trends Mol. Med.* 10, 344-350). It is known that LT contributes to cell transformation by binding to and inactivating the retinoblastoma (RB) and p53 tumor suppressor pathways. It is also known that ST contributes to cell transformation through its effects on the serine-threonine phosphatase family PP2A. In one embodiment, this set of proteins is expressed in human kidney epithelial (HEK), human mammary epithelial (HMEC) and human prostate epithelial cells (HPEC) (Berger et al. (2004) *Cancer Res.* 64, 8867-8875; Elenbaas and Weinberg (2001) *Exp. Cell Res.* 264, 169-184; Lundberg et al. (2002) *Oncogene* 21, 45774586; MacKenzie et al. (2002) *Oncogene* 21, 4200-4211; Rich et al. (2001) *Cancer Res.* 61, 3556-3560; Yu et al. (2001) *Virology* 290, 192-198).

Other embodiments include experimental models containing defined combinations of cancer-associated mutations that are able to transform human cells without viral oncoproteins (Boehm et al. (2005) *Mol. Cell. Biol.* 25, 6464-6474; Kendall et al. (2005) *Cancer Res.* 65, 9824-9828; Zhao et al. (2005) *Proc. Natl. Acad. Sci. USA* 102, 18443-18448) or experimental models that recapitulate particular tumor stages and types (Berger et al. (2004) *Cancer Res.* 64, 8867-8875; Chudnovsky et al. (2005) *Nat. Genet.* 37, 745-749; Zhao et al., (2003) *Cancer Cell* 3, 483-495). In yet another embodiment, the methods involve identifying genes and proteins affect cellular characteristics of transformation and/or tumorigenicity through the use of transformed and/or tumorigenic cells that are caused by undefined mutations or through the use of untransformed cells.

Methods described herein may be referred to as complementing methods. As used herein, the term "complement" refers to the ability of a gene or gene product to substitute for the expression of another gene or gene product to affect cellular characteristics of transformation and/or tumorigenicity.

In one embodiment, non-transformed and/or non-tumorigenic cells are contacted with and made to take up and express compositions capable of expressing regulatable or inhibitory protein(s), either alone or in combinations thereof, to alter characteristics of cellular transformation and/or tumorigenicity and thereby identify proteins that can complement existing genetic changes that together cause transformation and/or tumorigenesis. In another embodiment, transformed and/or tumorigenic cells with undefined mutations can be contacted with and made to take up and express compositions capable of expressing either a regulatable or inhibitory protein(s), either alone or in combinations thereof, to identify proteins that can complement undefined mutations in altering transformation characteristics of the cell. For example, the activation or inactivation of an expressed kinase in a transformed cell may cause a transformed cell whose growth is no longer regulated by dependence on IL3 to become IL3-dependent. In yet another embodiment, non-transformed cells can be contacted with and made to take up compositions capable of expressing a regulatable protein or inhibitory protein(s), either alone or in combinations thereof, to identify proteins that can complement wild type proteins in altering transformation characteristics of the cell. For example, the activation or inactivation of an expressed kinase may cause a non-transformed cell whose growth is IL3-dependent to no longer be regulated by IL3 for growth. A skilled artisan will appreciate that many cytokines or growth factors can be similarly used, including, but not limited to, members of the platelet-derived growth factor (PDGF), epidermal growth factor (EGF), fibroblast growth factor (FGF), bone morphogenetic proteins (BMPs), nerve growth factor (NGF), erythropoietin, insulin-like growth factor (IGF), tumor necrosis factor (TNF), colony stimulating factor (CSF), neurotrophin, transforming growth factor beta (TGFβ), IL-2, interferon (IFN), IL-10, IL-1, and L-17 families.

In one embodiment a transformed cell is contacted with one or more nucleic acids encoding one or more inhibitory mutants of proteins. Expression of one or more inhibitory mutants of proteins may downregulate one or more biological activities associated with the corresponding wild-type proteins. For example, cells can be contacted with pools of nucleic acids, such that the nucleic acids enter the cells and are expressed therein. The cell is then tested for loss of transforming capacity. Subpools of nucleic acids are then introduced into the same or different cells and the cells are tested for modulation, e.g. loss, of transforming capacity. These steps are reiterated until a nucleic acid encoding a protein that modulates, e.g. reverses, transformation is identified.

Several in vitro and in vivo assays for assessing characteristics of cellular transformation and/or tumorigenicity are envisioned. These assays rely on well described changes in cellular characteristics related to cellular transformation including, but not limited to, formation of foci, anchorage independence, loss of growth factor or serum requirements (e.g. IL-3-independent growth), change in cell morphology, ability to form tumors when injected into suitable animal hosts, and/or immortalization of the cell. In one embodiment, the well described anchorage-independent growth and colony formation in soft agar constitutes an in vitro transformation assay. When anchorage independence is the transformation characteristic being used in a particular assay, the cells used in the assay are cells which, when not transformed, are anchorage dependent. That is, when such cells are not transformed, they grow only when attached to a solid surface. Upon becoming transformed, such cells will grow in a medium (e.g. semi-solid agar) without being attached to a solid surface. In another embodiment, the well described tumor formation assay in immunocompromised ("nude") animals constitutes an in vivo transformation assay. Clones from colonies that grow in soft agar or as tumors in animals can be re-isolated by PCR on genomic DNA using vector-specific primers. Re-introduction of re-isolated regulatable proteins into the parental cells can serve to confirm that they reproducibly confer a transformed phenotype.

The methods envision subsequent assays to determine if the regulatable proteins that suffice to transform human cells are physiologically related to processes involved in driving spontaneously arising human cancers. An assay may rely on changes in expression characteristics of the gene identified in the above assay in human cancer specimens or cell lines derived from human cancer specimens relative to normal counterparts including, but not limited to, copy number gain, increased transcript levels, increased protein levels and oncogene addiction (Weinstein and Joe (2006) Nat. Clin. Pract. Oncol. 3, 448-457). Increased gene copy number can be detected by standard techniques currently known in the art and include for example, high-density SNP array (Zhao et al. (2004) Cancer Res. 64, 3060-3071), comparative genome hybridization (aCGH) (Pinkel et al. (1998) Nat. Genet. 20, 207-211) and/or fluorescence in situ hybridization (FISH) analyses. Increased transcript levels can be detected by standard techniques currently known in the art and include, for example, serial analysis of gene expression (SAGE), transcript expression microarray, publicly or privately available transcript expression databases, quantitative reverse transcription-coupled polymerase chain reaction (qRT-PCR), Northern blot, and/or RNase protection analyses. The degree of differences in expression levels need only be large enough to be visualized or measured via standard characterization techniques. Increased protein levels can be detected by standard techniques currently known in the art and include, for example, quantitative Western blot analyses using antibodies that detect either the protein itself or a peptide tag associated with the protein. Oncogene addiction is a phenomenon in which the expression of many oncogenes renders cancer cells unusually dependent upon the expression of the oncogene for cell proliferation or viability (Weinstein and Joe (2006) Nat. Clin. Pract. Oncol. 3, 448-457). The degree of oncogene addiction may be assessed by determining the extent to which cell proliferation or viability is affected when the cell is deprived of the functional oncoprotein. This may be achieved, for example, using RNA interference (RNAi), immunodepletion, dominant negative mutations, or loss of function mutations directed against the oncoprotein itself or the messenger RNA transcript or DNA gene encoding the oncoprotein.

IV. Exemplary Uses for Transforming and Anti-Tumor Genes

Regulatable proteins that alter characteristics of cellular transformation and/or tumorigenesis and were, e.g., identified by the methods described herein, can be used as a marker for the detection of disorders or diseases, e.g., cancer, that are associated with abnormal expression of the regulatable protein or generally for predicting whether a subject has or is likely to develop such as disorder or disease In one embodiment, a regulatable protein causing cellular transformation identified as described herein is expressed in a cell and the phosphorylation profile (i.e., the phosphorylation status of proteins within the cell) of the cell is determined. Comparison of the phosphorylation profile to that of a cell that was not transformed with the transforming regulatable protein will indicate a specific set of proteins that are phosphorylated only in the transformed cell. This phosphorylation profile can then be used as a point of comparison to determine whether a cell is transformed, e.g., by this particular transforming regulatable protein.

In another embodiment, an inhibitory protein, e.g. a dominant negative protein, causing cellular transformation identified as described herein is expressed in a cell and the phosphorylation profile (i.e., the phosphorylation status of proteins within the cell) of the cell is determined. Comparison of the phosphorylation profile to that of a cell that was not transformed with the inhibitory protein will indicate a specific set of proteins that are phosphorylated only in the transformed cell. This phosphorylation profile can then be used as a point of comparison to determine whether a cell is transformed, e.g., by this particular inhibitory protein.

In another embodiment, gene expression products of a cell in which a transforming regulatable protein is expressed are determined. By comparison with a cell that does not express the transforming regulatable protein, a specific set of gene expression products that are up- or down-regulated by the regulatable protein can be identified. This expression profile can then be used as a point of comparison to determine whether a cell is transformed, e.g., by this particular transforming regulatable protein.

In another embodiment, gene expression products of a cell in which a transforming inhibitory protein is expressed are determined. By comparison with a cell that does not express the transforming inhibitory protein, a specific set of gene expression products that are up- or down-regulated by the inhibitory protein can be identified. This expression profile can then be used as a point of comparison to determine whether a cell is transformed, e.g., by this particular inhibitory protein.

Determination of gene expression products from cells can be performed using common methods in the art (see, e.g., U.S. Patent Application Nos: 20030013208A1; 20020155493A1, 20030017515 and U.S. Pat. Nos. 6,329,209; 6,365,418, 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). The genes and proteins identified may be used for treating or preventing cancer, e.g., by down-regulating or up-regulating the levels of said identified genes and proteins. The genes and proteins identified can also be used to determine if the expression of such genes and proteins (e.g. a particular gene splice variant or a protein with a particular phosphorylation state) is associated with: 1) the identity of a sample (i.e. tumor or normal); 2) the state of differentiation; or 3) the predicted clinical outcome (e.g., either non-recurrence of tumor after surgery or recurrence).

In one embodiment, a biological sample can be classified with respect to a phenotypic effect, e.g. presence or absence cellular transformation characteristics, comprising the steps of isolating a gene expression product from a sample, for example from a cell or cells in the sample, and determining a gene expression profile of at least one informative gene, wherein the gene expression profile is correlated with a phenotypic effect, thereby classifying the sample with respect to a phenotypic effect. According to the methods of the invention, samples can be classified as belonging to (i.e. derived from) an individual who has or is likely to develop cancer. In a preferred embodiment, this cancer is breast cancer.

As used herein, "gene expression products" include proteins, peptides and nucleic acid molecules (e.g., mRNA, tRNA, rRNA, or cRNA). The nucleic acid molecule levels measured can be derived directly from the gene or, alternatively, from a corresponding regulatory gene. All forms of gene expression products can be measured, including, for example, splice variants or states of protein modification (e.g., phosphorylated versus unphosphorylated states of a given protein). Similarly, gene expression can be measured by assessing the level of protein or derivative thereof translated from mRNA. The sample to be assessed can be any sample that contains a gene expression product. Suitable sources of gene expression products, i.e., samples, can include cells, lysed cells, cellular material for determining gene expression, or material containing gene expression products. Examples of such samples are blood, plasma, lymph, urine, tissue, mucus, sputum, saliva or other cell samples. Methods of obtaining such samples are known in the art. In a preferred embodiment, the sample is derived from an individual who has been clinically diagnosed as having cancer or at risk of developing cancer.

As used herein, "obtaining" means acquiring a sample, either by directly procuring a sample from a patient or a sample (tissue biopsy, primary cell, cultured cells), or by receiving the sample from one or more people who procured the sample from the patient or sample and determining the gene expression levels therein.

Once the samples are obtained, the profile of gene expression levels of the sample are determined. As used herein, "gene expression profiles" are defined as the level of gene expression of a particular gene, protein or modified protein and groups thereof as assessed by methods described herein. In one embodiment, the gene expression product is a nucleic acid. The skilled artisan will readily know many methods to determine gene expression levels of individual or groups of gene transcripts expressed in a given sample. For example, gene transcript levels can be determined using serial analysis of gene expression (SAGE), transcript expression microarray, publicly or privately available transcript expression databases, quantitative reverse transcription-coupled polymerase chain reaction (qRT-PCR), Northern blot, and/or RNase protection analyses. In another embodiment, the gene expression product is a protein or polypeptide. Protein levels can be detected by standard techniques currently known in the art and include, for example, quantitative Western blot analyses using antibodies that detect either the protein itself or a peptide tag associated with the protein. Such antibodies, if directed against modified proteins (e.g. phosphorylated protein forms), are useful for detecting modified protein species that may be differentially present in cancer cells relative to appropriate controls. A skilled artisan will understand that transcript and protein levels of a given gene may be altered due to alterations in the copy of number of that gene in the genome. A skilled artisan will also understand that expression of numerous genes can be measured simultaneously, using genome-wide methods known in the art and that the assessment of numerous genes provides for a more accurate evaluation of the sample because there are more genes that can assist in classifying the sample.

Once the gene expression levels of the sample are obtained, the levels are compared or evaluated against appropriate controls, and the sample is classified. The evaluation of the sample determines whether or not the sample should be assigned to the particular phenotypic class being studied. The gene expression value measured or assessed can be interpreted using a number of methods familiar to the skilled artisan. For example, numeric expression values can be quantified and analyzed with software (e.g., Microsoft Excel® spreadsheet and Affymetrix GENECHIP® software). Phenotype classification (e.g. presence or absence of cancer, diagnostic risk assessment for developing cancer or state of therapeutic outcome) can be made by comparing the gene expression profile of the sample with respect to one or more informative genes, proteins and modified proteins with one or more appropriate control gene expression profiles (e.g., in a database). For example, a level of a regulatable protein, e.g., IKKε, that is higher or lower in a sample of a subject relative to a control sample indicates that the subject may have or is likely to develop cancer.

As used herein, "informative genes" can be cancer identification genes, for example, all or a subset of the genes having increased or decreased expression in immediately transformed cells relative to appropriate controls; cancer differentiation genes, for example, all or a subset of the genes having increased or decreased expression in established transformed cells relative to appropriate controls; and tumor recurrence genes, for example, all or a subset of genes having increased or decreased expression in recurrent tumors relative to appropriate controls. A skilled artisan will readily understand that not all informative genes for a particular class distinction must be assessed in order to classify a sample. For example, it may be sufficient to determine that a level of a regulatable protein, e.g., IKKε, that is higher or lower in a sample of a subject relative to a control sample indicates that the subject may have or is likely to develop cancer. Similarly, the set of informative genes for one phenotypic effect may or may not be the same as the set of informative genes for a different phenotypic effect. For example, a subset of the informative genes which demonstrate a high correlation with a class distinction can be used. This subset can be, for example, 1 or more genes, 2 or more genes, 3 or more genes, 4 or more genes, 5 or more genes, 10 or more genes, 25 or more genes, or 50 or more genes. It will be understood that the methods of the present invention classify a sample by evaluating a sample for a gene or combination of genes, proteins or modification states of proteins whose expression is increased and/or decreased in transformed cells relative to appropriate controls.

The correlation between gene expression criteria used to classify a sample and class distinction can be used to evaluate the effectiveness of the given gene expression criteria as a diagnostic marker for a given class distinction. This correlation can be determined using a variety of methods. For example, methods of defining classes and classifying samples are known in the art, as exemplified in U.S. patent application Ser. No. 09/544,627, filed Apr. 6, 2000 by Golub et al.

Also provided are methods for monitoring the effect of a regulatable protein on characteristics of cellular transformation or for monitoring the effect of a treatment regimen in an individual by monitoring the gene expression profile for one or more informative genes relative to appropriate controls. For example, a baseline gene expression profile for an immortal, non-transformed cell (e.g. HMEL) can be determined, and repeated gene expression profiles can be determined at time points after which a regulatable protein(s) is added that is able to complement a known protein in altering characteristics of cellular transformation (e.g. HMELs expressing MEKDD and IKBKE). Analysis of gene expression differences at different time points can identify informative genes useful in the diagnosis of cancer types and stages and useful in identifying therapeutic targets. Similarly, a baseline gene expression profile from an individual at risk for cancer or having cancer can be determined, and repeated gene expression profiles can be determined at various time points during cancer treatment. For example, a shift in gene expression profile from a profile correlated with poor treatment outcome to a profile correlated with improved treatment outcome is evidence of an effective therapeutic regimen, while a repeated profile correlated with poor treatment outcome is evidence of an ineffective therapeutic regimen.

V. Compositions and Methods for Diagnosing a Disease or Disorder Based on Regulatable Proteins Identified Herein The term "cancer" is meant to be interpreted in the broadest sense, and to include solid and nonsolid malignancies, premalignancies, and tumors which are malignant by virtue of their location such as, for example, within the brain. The term "cancers of epithelial origin" refers to cancers that arise from epithelial cells which include, but are not limited to, breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body.

The term "aggressive" or "invasive" with respect to cancer refers to the proclivity of a tumor for expanding beyond its boundaries into adjacent tissue (Darnell, J. (1990), Molecular Cell Biology, Third Ed., W.H. Freeman, N.Y.). Invasive cancer can be contrasted with organ-confined cancer wherein the tumor is confined to a particular organ. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located.

The term "metastasis", as used herein, refers to the condition of spread of cancer from the organ of origin to additional distal sites in the patient. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

A "biological sample" refers to a sample of biological material obtained from a subject, preferably a human subject, including a tissue, a tissue sample, a cell sample, a tumor sample, and a biological fluid, e.g., blood, urine and a nipple aspirate. A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy, and an endoscopic biopsy.

An "isolate" of a biological sample (e.g., an isolate of a tissue or tumor sample) refers to a material or composition (e.g., a biological material or composition) which has been separated, derived, extracted, purified or isolated from the sample and additionally may be substantially free of undesirable compositions and/or impurities or contaminants associated with the biological sample.

A "tissue sample" includes a portion, piece, part, segment, or fraction of a tissue which is obtained or removed from an intact tissue of a subject, preferably a human subject.

A "tumor sample" includes to a portion, piece, part, segment, or fraction of a tumor, for example, a tumor which is obtained or removed from a subject (e.g., removed or extracted from a tissue of a subject), preferably a human subject.

A "primary tumor" is a tumor appearing at a first site within the subject and can be distinguished from a "metastatic tumor" which appears in the body of the subject at a remote site from the primary tumor.

The term "level" refers to the qualitative and/or quantitative amount and/or activity of, for example, a regulatable protein in a given specimen, cell, tissue, organ, subject, etc.

Provided herein are methods for determining whether a subject has or is likely to develop a disease or disorder, e.g. cancer, associated with a regulatable protein identified herein. A method may comprise measuring the level of expression of a regulatable protein, e.g., IKKε, in a subject, e.g., in a biological sample obtained from a patient. The method may further comprise comparing the observed level of the regulatable protein in said sample against one or a range of levels of the regulatable protein normally found in biological samples (of the same type) of healthy individuals.

Determining the level of a regulatable protein in a cell or a biological sample includes qualitatively or quantitatively determining the level and/or the activity of the protein of the regulatable protein or degradation product thereof, the level of mRNA or pre-mRNA encoding said regulatable protein, the number of genomic loci encoding said regulatable protein, or the level and/or activity of any biological molecule or product that is indicative of expression of said regulatable protein, or degradation product thereof.

It may be sufficient to detect the presence of the regulatable protein rather than determining its level and comparing it to a standard or control level, as the levels of the regulatable protein may be relatively low in normal cells and tissues and may not be detectable by standard methods of detection, e.g., immunohistochemistry.

In one embodiment, a control may constitute the level of a regulatable protein, e.g., IKKε, in a normal or healthy tissue of the same type as that from which a sample was obtained. A control may be an average or mean value of at least 2, 5, 10 or more values of levels of the regulatable protein in normal or healthy tissues. A control may also be a normal control sample, i.e., a sample obtained from a normal or healthy individual, or an individual who does not have cancer, or at least not the type of cancer that is being investigated.

For purposes of comparison, a test sample and a normal control sample may be of the same type, that is, obtained from the same biological source. A normal control sample can also be a standard sample that contains the same concentration of a regulatable protein that is normally found in a biological sample of the same type and that is obtained from a healthy individual, e.g., an individual who does not have cancer, e.g., breast cancer. For example, there can be a standard normal control sample for the amounts of a regulatable protein normally found in a cell or tissue.

When comparing the level of a regulatable protein to a control value, an increased likelihood for developing cancer or having cancer may be concluded from the presence of at least about 1.5 fold, 2 fold, 5 fold, 10 fold, 30 fold, 50 fold, 100 fold higher or lower levels of the regulatable protein in the sample of the subject compared to the control value. The term "higher or lower level" in the context of levels of a regulatable protein in a sample from a patient relative to a control value of the level in a tissue from a healthy subject refers to a level that is statistically significant or significantly above or below levels found in the control value or tissue from the healthy subject. The term "statistically significant" or "significantly" refers to statistical significance and generally means a two standard deviation (2SD) or larger difference in regulatable protein levels of the marker in the experimental sample relative to the control. The levels of the regulatable protein can be represented by arbitrary units, for example, as units obtained from a densitometer, luminometer, or an ELISA plate reader.

Levels of a regulatable protein, e.g., IKKε, may also be determined in cells or tissue adjacent to or in the vicinity of a tumor, e.g., lymph node cells. A control value or sample may then be obtained from the same type of cells.

Based at least on the fact that tests based on a regulatable protein described herein may be more sensitive than known tests in predicting the presence or development of cancer, one can also determine levels of the regulatable protein in tissue that does not appear to contain a growth or tumor. The presence of higher or lower levels of the regulatable protein in such a tissue would indicate the presence or the likelihood of development of cancer in said tissue or potentially another tissue.

The methods described herein may be useful for determining whether a subject has or is likely to develop any one of a variety of cancers. Examples of such cancers include, but are not limited to, epithelial cancers, urogenital cancer, e.g., urinary bladder cancer, transitional cell carcinoma (TCC), prostate cancer, lung carcinoma, breast carcinoma, thyroid carcinoma, brain cancers (cerebellum, medulloblastoma, astrocytoma, ependymoma, glioblastoma), pancreatic carcinoma, ovarian carcinoma, uterine cancer, eye cancer (retinoblastoma), muscle (rhabdosarcoma), lymphoma, stomach cancer, liver cancer, and colon cancer. Generally, cancers may be cancers of the prostate, lung, breast, thyroid, brain (e.g., cerebellum, medulloblastoma, astrocytoma, ependymoma, glioblastoma), pancreas, ovary, eye (e.g., retinoblastoma), muscle (e.g., rhabdosarcoma), lymph, stomach, liver, colon, bladder, uterus, and kidney.

Determining the levels of a regulatable protein, e.g., IKKε, in a subject or a biological sample may also be used to determine whether a subject has or is likely to develop cancer. In one embodiment, a method for determining whether a subject has or is likely to develop cancer comprises determining the level of a regulatable protein in the subject, such as in cells or tissues of the subject. The method allows the detection or likelihood of development of any cancer that is associated with high or low expression of the regulatable protein relative to an appropriate control, as further described herein. A method may involve measuring levels of the regulatable protein in a test sample obtained from a patient having or suspected of having cancer. A method may further comprise comparing the observed levels of the regulatable protein to a control or to levels of the regulatable protein found in a normal control sample, for example, a sample obtained from a subject that does not have cancer. The presence of regulatable protein at levels that are higher or lower than those observed in an appropriate control indicate the presence of cancer or the likelihood of developing cancer.

Additionally, disease progression can be assessed by following the levels of a regulatable protein, e.g. IKKε levels, in individual patients over time. Accordingly, methods provided herein also include methods for monitoring the progression of cancer in a subject, comprising, e.g., monitoring the presence or level of the regulatable protein in a cell, e.g., in a cancerous cell or tumor, of the subject over time. A change in the regulatable protein over time indicates that the cancer is progressing or retreating. In another embodiment, a reference reading is taken after an operation involving the cancer and others taken at regular intervals subsequent to the operation. Any change in the level of the regulatable protein over time indicates that the cancer is progressing or retreating.

The information provided by the methods described herein may be used by the physician in determining the most effective course of treatment. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

Also provided herein are methods for diagnosing followed by treating a subject having cancer. A method may comprise (i) determining the level of a regulatable protein, e.g., IKKε, in a cancerous tumor of a subject; and (ii) if the level of the regulatable protein is higher or lower in the cancerous tumor of the subject relative to a control, treating the subject aggressively, whereas if the level of the regulatable protein in the cancerous tumor of a subject is statistically within the range of an appropriate control, treating the subject less aggressively. An aggressive therapy may comprise surgical removal of cancer cells or a tissue comprising the cancer cells, e.g., mastectomy in the case of breast cancer, chemotherapy, radiation, or a combination thereof. Surgical removal may be followed by early systematic therapy. The treatment may then be followed by continued monitoring of the levels of the regulatable protein.

The levels of the regulatable protein in cancer patients can be easily added in the pathology report with other pathological predictors including tumor size, grade, subtype, and stage for the patient's outcome information and clinical treatment.

Determining the level of a regulatable protein, e.g., IKKε, may also be combined with the detection of one or more other biomarkers for which increased or decreased expression correlates with cancer. The selected biomarker can be a general diagnostic or prognostic marker useful for multiple types of cancer, such as CA 125, CEA or LDH, or can be a cancer-specific diagnostic or prognostic marker, such as a breast cancer marker (for example, CA 15-2. Her-2/neu and CA 27.29), colon cancer marker (for example, sialosyl-TnCEA, CA19-9, or LASA), ovarian cancer marker (for example, CA72-4), lung cancer (for example, neuron-specific enolase (NSE) and tissue polypeptide antigen (TPA)), prostate cancer (for example, PSA, prostate-specific membrane antigen and prostatic acid phosphatase), melanoma (for example, S-100 and TA-90), as well as other biomarkers specific for other types of cancer. Those skilled in the art will be able to select useful diagnostic or prognostic markers for detection in combination with a regulatable protein. Similarly, three or more, four or more or five or more or a multitude of biomarkers can be used together for determining a diagnosis or prognosis of a patient.

Also provided herein are kits, e.g., kits for determining the level of a regulatable protein, e.g. IKKε, in a subject or in a biological sample of a subject. A kit may comprise any agent useful for qualitatively or quantitatively detecting the regulatable protein, RNA (including pre-mRNA and mRNA) encoding the regulatable protein, or changes in copy number of genomic loci encoding the regulatable protein, such as agents further described herein. A kit may further comprise a control, such as a control value or control sample or control tissue. A control may be protein or nucleic acid attached to a solid support. A kit may also comprise additional components or reagents necessary for the detection of the regulatable protein, such as secondary antibodies for use in immunohistochemistry.

In one embodiment, the protein level of a regulatable protein, e.g., IKKε, is measured. It is generally preferred to use antibodies, or antibody equivalents, to detect the regulatable protein. Methods for the detection of protein are well known to those skilled in the art, and include ELISA (enzyme linked immunosorbent assay), RIA (radioimmunoassay), Western blotting, and immunohistochemistry. Immunoassays, such as ELISA or RIA, which can be extremely rapid, are more generally preferred. Antibody arrays or protein chips can also be employed, see for example U.S. Patent Application Nos: 20030013208A1; 20020155493A1, 20030017515 and U.S. Pat. Nos. 6,329,209; 6,365,418, herein incorporated by reference in their entirety.

ELISA and RIA procedures may be conducted such that a protein standard for the regulatable protein is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the regulatable protein in the sample is allowed to react with the corresponding immobilized antibody, radioisotope or enzyme-labeled antibody that specifically recognizes the regulatable protein is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring the levels of a regulatable protein comprises the steps of: contacting a biological specimen with an antibody or variant (e.g., fragment) thereof which selectively binds the regulatable protein, and detecting whether said antibody or variant thereof is bound to said sample and thereby measuring the levels of the regulatable protein.

Enzymatic and radiolabeling of the regulatable protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect a regulatable protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Antibodies that bind the regulatable protein (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of the regulatable protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Antibodies that bind the regulatable protein may also be used for imaging purposes, for example, to detect the presence of the regulatable protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{121}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the patient, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99 m. The labeled antibody or antibody fragment will then preferentially accumulate at the location of cells which contain the regulatable protein. The labeled antibody or antibody fragment can then be detected using known techniques.

Antibodies that may be used to detect a regulatable protein include any antibody, whether natural or synthetic, full length or a fragment thereof, monoclonal or polyclonal, that binds sufficiently strongly and specifically to the regulatable protein to be detected. An antibody may have a Kd of at most about $10^{-6}$ M, $10^{-7}$ M, $10^{-8}$ M, $10^{-9}$ M, $10^{-10}$ M, $10^{-11}$ M, $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the regulatable protein relative to other proteins, such as related proteins, including homologs of the regulatable protein.

Such antibodies may be commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., binding fragments a regulatable protein, of antibodies. For example, antibody fragments capable of binding to the regulatable protein or portions thereof, including, but not limited to, Fv, Fab, Fab' and F (ab') 2 fragments can be used. Such fragments can be produced by enzymatic cleavage or by recombinant techniques. For example, papain or pepsin cleavage can generate Fab or F (ab') 2 fragments, respectively. Other proteases with the requisite substrate specificity can also be used to generate Fab or F (ab') 2 fragments. Antibodies can also be produced in a variety of truncated forms using antibody genes in which one or more stop codons have been introduced upstream of the natural stop site. For example, a chimeric gene encoding a F (ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a regulatable protein, e.g., IKKε, other than antibodies are used, such as peptides. Peptides that specifically bind to the regulatable protein can be identified by any means known in the art. For example, specific peptide binders of the regulatable protein can be screened for using peptide phage display libraries.

Generally, agents that are capable of detecting protein of the regulatable protein, such that the presence of the regulatable protein is detected and/or quantitated, may be used. As defined herein, an "agent" refers to a substance which is capable of identifying or detecting the regulatable protein in a biological sample (e.g., identifies or detects protein of or nucleic acid encoding the regulatable protein). In one embodiment, the agent is a labeled or labelable antibody that specifically binds to the regulatable protein. As used herein, the phrase "labeled or labelable" refers to the attaching or including of a label (e.g., a marker or indicator) or ability to attach or include a label (e.g., a marker or indicator). Markers or indicators include, but are not limited to, for example, radioactive molecules, colorimetric molecules, and enzymatic molecules which produce detectable changes in a substrate.

In addition, the regulatable protein may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) *Tibtech* 18, 151-160; Rowley et al. (2000) Methods 20, 383-397; Kuster and Mann (1998) *Curr. Opin. Structural Biol.* 8, 393-400). Further, mass spectrometric techniques have been developed that permit at least partial de novo sequencing of isolated proteins (see, e.g., Chait et al. (1993) *Science* 262, 89-92; Keough et al. (1999) *Proc. Natl. Acad. Sci. USA.* 96, 7131-7136; reviewed in Bergman (2000) *EXS* 88, 133-44).

In certain embodiments, a gas phase ion spectrophotometer is used. In other embodiments, laser-desorption/ionization mass spectrometry is used to analyze the sample. Modem laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes (see, e.g., Hellenkamp et al., U.S. Pat. No. 5,118,937 and Beavis and Chait, U.S. Pat. No. 5,045,694).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied (see, e.g., Hutchens and Yip, U.S. Pat. No. 5,719,060 and Hutchens and Yip, WO 98/59361). The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually or by computer analysis) to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands that any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to be mixed with the known control sample in the same mass spectrometry run.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantification of the amount of the biomolecule present in the first sample. In certain embodiments, the identity of the biomolecules in the first and second sample can also be determined.

In one embodiment, detecting or determining levels of a regulatable protein comprises detecting or determining the levels of RNA encoding the regulatable protein. In one embodiment, one or more cells from the subject to be tested are obtained and RNA is isolated from the cells. When obtaining the cells, it is preferable to obtain a sample containing predominantly cells of the desired type, e.g., a sample of cells in which at least about 50%, preferably at least about 60%, even more preferably at least about 70%, 80% and even more preferably, at least about 90% of the cells are of the desired type. Tissue samples can be obtained according to methods known in the art.

It is also possible to obtain a cell sample from a subject, and then to enrich it in the desired cell type. For example, cells can be isolated from other cells using a variety of techniques, such as isolation with an antibody binding to an epitope on the cell surface of the desired cell type. Where the desired cells are in a solid tissue, particular cells can be dissected out, e.g., by microdissection.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly-become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190: 199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the Message-Maker® kit (Life Technologies, Grand Island, N.Y.).

In another embodiment, the RNA population is enriched in sequences encoding a regulatable protein, e.g., IKKε. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used (see Examples).

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 454-4610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a patient may be hybridized to a solid surface comprising DNA encoding a regulatable protein. Positive hybridization signal is obtained with the sample containing RNA transcripts, DNA or cDNA encoding the regulatable protein. Methods of preparing DNA arrays and their use are well known in the art (see, e.g., U.S. Pat. Nos. 6,618, 6796; 6,379,897; 6,664,377; 6,451,536; 548,257; U.S. 20030157485 and Schena et al. (1995) Science 20, 467-470; Gerhold et al. (1999) Trends In Biochem. Sci. 24, 168-173; and Lennon et al. (2000) Drug Discovery Today 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to cDNA generated from transcripts encoding a regulatable protein are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize mRNA transcripts of a regulatable protein, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the gene encoding the regulatable protein. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

In one embodiment, a change in copy number of genomic loci encoding a regulatable protein, e.g., IKKε, is detected. In one embodiment, the biological sample is tested for the presence of copy number changes in genomic loci encoding the regulatable protein. A copy number of at least 3, 4, 5, 6, 7, 8, 9, or 10 is indicative of the presence of cancer or the likelihood of developing cancer.

Methods of evaluating the copy number of a particular biomarker or chromosomal region associated with a regulatable protein (e.g., IKBKE or chromosome 1q32) include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the copy number of a gene encoding a regulatable protein in a sample involves a Southern Blot. In a Southern Blot, the genomic DNA (typically fragmented and separated on an electrophoretic gel) is hybridized to a probe specific for the target region (e.g., IKBKE or chromosome 1q32). Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA encoding the regulatable protein can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets, e.g., cells, are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a form that is visualizable, if necessary. Chromosomal regions in the test cells, which are at increased or decreased copy number, can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.). In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93) may also be used to identify regions of amplification or deletion.

VI. Therapeutics for Treating a Disease or Disorder Based on Regulatable Proteins Identified Herein Based at least on the observation that altered levels of regulatable proteins, e.g., IKKε, identified herein lead to altered characteristics of cellular transformation and/or tumorigenicity, it may be possible to diminish the likelihood of developing cancer, halt the progression of cancer, or prevent cancer altogether by controlling the level of a regulatable protein in a tumor or tissue of the subject. In one embodiment, a method for treating or preventing cancer comprises reducing the level of expression of a regulatable protein. A method may include reducing the level of nucleic acid encoding the regulatable protein, reducing the amount of the regulatable protein, or inhibiting the activity of the regulatable protein. In a method for treatment, one may decrease levels and/or activity of the regulatable protein or the nucleic acid encoding it in a tumor, e.g., a primary tumor. In a method for preventing cancer, one may decrease levels and/or activity of the regulatable protein or the nucleic acid encoding it in tissue likely to develop cancer.

Prophylaxis may be appropriate even at very early stages of the disease, to prevent tumorigenesis or metastasis. Thus, administration of an agent that decreases levels and/or activity of a regulatable protein or the nucleic acid encoding it may be effected as soon as cancer is diagnosed, and treatment continued for as long as is necessary, generally until the threat of the disease has been removed. Such treatment may also be used prophylactically in individuals at high risk for developing cancer.
ment of certain cancers, e.g., breast cancer.

RNAi Technology

In one embodiment, levels of nucleic acid encoding a regulatable protein are decreased by administration of or expression in a subject, e.g., in cells or a tissue of the subject, of one or more siRNAs.

Isolated RNA molecules specific to mRNA encoding the regulatable protein, which mediate RNAi, are antagonists useful in the method of the present invention (see, e.g., U.S. Patent Application Nos: 20030153519A1; 20030167490A1; and U.S. Pat. Nos. 6,506,559; 6,573,099, which are herein incorporated by reference in their entirety).

In one embodiment, the RNA is comprised of, or capable of being cleaved to, short interfering or small interfering RNAs (siRNAs). The term "short interfering RNAs (siRNA)" as used herein is intended to refer to any nucleic acid molecule capable of mediating RNAi or gene silencing. The term siRNA is intended to encompass various naturally generated or synthetic compounds, with RNAi function. Such compounds include, without limitation, duplex synthetic oligonucleotides, of about 21 to 23 base pairs with terminal overlaps of 2 or 3 base pairs; hairpin structures of one oligonucleotide chain with sense and complementary, hybridizing, segments of 21-23 base pairs joined by a loop of 3-5 base pairs; and various genetic constructs leading to the expression of the preceding structures or functional equivalents. Such genetic constructs are usually prepared in vitro and introduced in the test system, but can also include siRNA from naturally occurring siRNA precursors encoded by the genome of the host cell or animal.

It is not a requirement that the siRNA be comprised solely of RNA. In one embodiment, the siRNA comprises one or more chemical modifications and/or nucleotide analogues. The modification and/or analogue may be any modification and/or analogue, respectively, that does not negatively affect the ability of the siRNA to inhibit expression of nucleic acid encoding a regulatable protein. The inclusion of one or more chemical modifications and/or nucleotide analogues in an siRNA may be used to prevent or slow nuclease digestion, and in turn, create a more stable siRNA for practical use. Chemical modifications and/or nucleotide analogues which stabilize RNA are known in the art. Phosphorothioate derivatives, which include the replacement of non-bridging phosphoryl oxygen atoms with sulfur atoms, are one example of analogues showing increased resistance to nuclease digestion. Sites of the siRNA which may be targeted for chemical modification include the loop region of a hairpin structure, the 5' and 3' ends of a hairpin structure (e.g. cap structures), the 3' overhang regions of a double-stranded linear siRNA, the 5' or 3' ends of the sense strand and/or antisense strand of a linear siRNA, and one or more nucleotides of the sense and/or antisense strand.

As used herein, the term siRNA is intended to be equivalent to any term in the art defined as a molecule capable of mediating sequence-specific RNAi. Such equivalents include, for example, double-stranded RNA (dsRNA), microRNA (miRNA), short hairpin RNA (shRNA), short interfering oligonucleotide, endoribonuclease-prepared siRNA (esiRNA), and post-transcriptional gene silencing RNA (ptgsRNA).

siRNAs may be introduced into cells to suppress gene expression for therapeutic or prophylactic purposes as described in International Publication Number WO 0175164. Such molecules may be introduced into cells to suppress gene expression for therapeutic or prophylactic purposes as described in various patents, patent applications and papers. Publications herein incorporated by reference, describing RNAi technology include, but are not limited to, the following: U.S. Pat. No. 6,686,463, U.S. Pat. No. 6,673,611, U.S. Pat. No. 6,623,962, U.S. Pat. No. 6,506,559, U.S. Pat. No.

6,573,099, and U.S. Pat. No. 6,531,644; International Publication Numbers WO04061081; WO04052093; WO04048596; WO04048594; WO04048581; WO04048566; WO04046320; WO04044537; WO04043406; WO04033620; WO04030660; WO04028471; WO 0175164. Papers which describe the methods and concepts for the optimal use of these compounds include, but are not limited to, the following: Brummelkamp Science 296: 550-553 (2002); Caplen Expert Opin. Biol. Ther. 3:575-86 (2003); Brummelkamp, Science Express 21 Mar. 3 1-6 (2003); Yu Proc Natl Acad Sci USA 99:6047-52 (2002); Paul, Nature Biotechnology 29:505-8 (2002); Paddison, Proc Natl Acad Sci USA 99:1443-8 (2002); Brummelkamp, Nature 424: 797-801 (2003); Brummelkamp, Science 296: -550-3 (2003); Sui, Proc Natl Acad Sci USA 99: 5515-20 (2002); Paddison, Genes and Development 16:948-58 (2002).

A composition comprising an siRNA effective to inhibit expression of nucleic acid encoding a regulatable protein, e.g., IKBKE, may include an RNA duplex comprising a sense sequence encoding the regulatable protein. In this embodiment, the RNA duplex comprises a first strand comprising a sense sequence encoding the regulatable protein and a second strand comprising a reverse complement of the sense sequence encoding the regulatable protein. In one embodiment the sense sequence encoding the regulatable protein comprises of from 10 to 25 nucleotides in length. In another embodiment, the sense sequence encoding the regulatable protein comprises of from 19 to 25 nucleotides in length. In yet another embodiment, the sense sequence encoding the regulatable protein comprises of from 21 to 23 nucleotides in length. The sense sequence encoding the regulatable protein can comprises a sequence of the regulatable protein containing a translational start site or a portion of the regulatable protein sequence within the first 400 nucleotides of the nucleic acid encoding the regulatable protein.

In another embodiment, a composition comprising an siRNA effective to inhibit the nucleic acid encoding the regulatable protein expression may comprise in a single molecule a sense sequence encoding the regulatable protein, the reverse complement of the sense sequence encoding the regulatable protein, and an intervening sequence enabling duplex formation between the sense and reverse complement sequences. The sense sequence encoding the regulatable protein may comprise 10 to 25 nucleotides in length, 19 to 25 nucleotides in length, or 21 to 23 nucleotides in length.

It will be readily apparent to one of skill in the art that an siRNA of the present invention may comprise a sense sequence encoding the regulatable protein or the reverse complement of the sense sequence encoding the regulatable protein which is less than perfectly complementary to each other or to the targeted region encoding the regulatable protein. In other words, the siRNA may comprise mismatches or bulges within the sense or reverse complement sequence. In one aspect, the sense sequence or its reverse complement may not be entirely contiguous. The sequence or sequences may comprise one or more substitutions, deletions, and/or insertions. The only requirement of the present invention is that the siRNA sense sequence possess enough complementarity to its reverse complement and to the targeted region of the regulatable protein to allow for RNAi activity. It is an object of the present invention, therefore, to provide for sequence modifications of an siRNA of the present invention that retain sufficient complementarity to allow for RNAi activity. One of skill in the art may predict that a modified siRNA composition of the present invention will work based on the calculated binding free energy of the modified sequence for the complement sequence and targeted region encoding the regulatable protein. Methods for calculating binding free energies for nucleic acids and the effect of such values on strand hybridization are known in the art.

A wide variety of delivery systems are available for use in delivering an siRNA of the present invention to a target cell in vitro and in vivo. An siRNA of the present invention may be introduced directly or indirectly into a cell in which inhibition of the nucleic acid encoding the regulatable protein is desired. An siRNA may be directly introduced into a cell by, for example, injection. As such, it is an object of the invention to provide for a composition comprising an siRNA effective to inhibit the nucleic acid encoding the regulatable protein in injectable, dosage unit form. An siRNA of the present invention may be injected intravenously or subcutaneously, as an example, for therapeutic use in conjunction with the methods and compositions of the present invention. Such treatment may include intermittent or continuous administration until therapeutically effective levels are achieved to inhibit expression of the nucleic acid encoding the regulatable protein in the desired tissue.

Indirectly, an expressible DNA sequence or sequences that encode the siRNA may be introduced into a cell and the siRNA, thereafter, transcribed from the DNA sequence or sequences. It is an object of the present invention, therefore, to provide for compositions comprising a DNA sequence or sequences which encode an siRNA effective to inhibit the regulatable protein expression.

A DNA composition of the present invention comprises a first DNA sequence which encodes a first RNA sequence comprising a sense sequence of a regulatable protein, e.g., IKBKE, and a second DNA sequence which encodes a second RNA sequence comprising the reverse complement of the sense sequence encoding the regulatable protein. The first and second RNA sequences, when hybridized, form an siRNA duplex capable of forming an RNA-induced silencing complex, the RNA-induced silencing complex being capable of inhibiting expression of the nucleic acid encoding the regulatable protein. The first and second DNA sequences may be chemically synthesized or synthesized by PCR using appropriate primers to the regulatable protein. Alternatively, the DNA sequences may be obtained by recombinant manipulation using cloning technology, which is well known in the art. Once obtained, the DNA sequences may be purified, combined, and then introduced into a cell in which inhibition of the regulatable protein is desired. Alternatively, the sequences may be contained in a single vector or separate vectors and the vector or vectors introduced into the cell in which inhibition of the regulatable protein is desired.

Delivery systems available for use in delivering a DNA composition of the present invention to a target cell include, for example, viral and non-viral systems. Examples of suitable viral systems include, for example, adenoviral vectors, adeno-associated virus, lentivirus, poxvirus, retroviral vectors, vaccinia, herpes simplex virus, HIV, the minute virus of mice, hepatitis B virus and influenza virus. Non-viral delivery systems may also be used, for example using, uncomplexed DNA, DNA-liposome complexes, DNA-protein complexes and DNA-coated gold particles, bacterial vectors such as *salmonella*, and other technologies such as those involving VP22 transport protein, Co-X-gene, and replicon vectors. A viral or non-viral vector in the context of the present invention may express the antigen of interest.

Antisense Technology

In another embodiment, the level of nucleic acid encoding a regulatable protein, e.g., IKBKE, is decreased by administration or the expression of antisense molecules in a subject or tissue or cell thereof.

Gene expression can be controlled through triple-helix formation or antisense DNA or RNA, both of which methods are based on binding of a polynucleotide to DNA or RNA. An antisense nucleic acid molecule which is complementary to a nucleic acid molecule encoding the regulatable protein can be designed based upon the isolated nucleic acid molecules encoding the regulatable protein. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence in the coding region of the mRNA or can be complementary to a 5' or 3' untranslated region of the mRNA. Furthermore, an antisense nucleic acid can be complementary in sequence to a regulatory region of the gene encoding the mRNA, for instance, a transcription initiation sequence or regulatory element. In one embodiment, an antisense nucleic acid complementary to a region preceding or spanning the initiation codon or in the 3' untranslated region of an mRNA is used. An antisense nucleic acid can be designed based upon the nucleotide sequence encoding the regulatable protein. A nucleic acid is designed which has a sequence complementary to a sequence of the coding or untranslated region of the regulatable protein. Alternatively, an antisense nucleic acid can be designed based upon sequences of gene(s) encoding the regulatable protein, which can be identified by screening a genomic DNA library with an isolated nucleic acid of the invention. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids. For example, phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1 (1)1986.

In addition, ribozymes can be used to inhibit in vitro expression of nucleic acids encoding a regulatable protein, e.g., IKBKE. For example, the nucleic acids of the invention can further be used to design ribozymes which are capable of cleaving a single-stranded nucleic acid encoding the regulatable protein, such as an mRNA transcript encoding the regulatable protein. A catalytic RNA (ribozyme) having ribonuclease activity can be designed which has specificity for an mRNA encoding the regulatable protein based upon the sequence of a nucleic acid of the invention. For example, a derivative of a Tetrahymena L-19 IVS RNA can be constructed in which the base sequence of the active site is complementary to the base sequence to be cleaved in an mRNA encoding the regulatable protein (see, e.g., Cech et al., U.S. Pat. No. 4,987,071; Cech, et al., U.S. Pat. No. 5,116, 742). Alternatively, a nucleic acid of the invention could be used to select a catalytic RNA having a specific ribonuclease activity from a pool of RNA molecules (see, e.g., Bartel and Szostak (1993) *Science* 261, 1411-1418).

Blocking Antibodies and Aptamer Technology

In yet another embodiment, levels and/or activity of a regulatable protein, e.g., IKKε, are reduced by administration to or expression in a subject or a cell or tissue thereof, of blocking antibodies or aptamers against the regulatable protein.

Antibodies, or their equivalents and derivatives, e.g., intrabodies, or other antagonists of the regulatable protein, may be used in accordance with the present invention for the treatment or prophylaxis of cancers. Administration of a suitable dose of the antibody or the antagonist may serve to block the activity of the protein and this may provide a crucial time window in which to treat malignant growth.

A method of treatment involves attachment of a suitable toxin to the antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of suitable physiologically active compounds, which may be used, for example, to treat cancers.

In addition to using antibodies to inhibit the levels and/or activity of the regulatable protein, it may also be possible to use other forms of inhibitors. For example, it may be possible to identify antagonists that functionally inhibit the regulatable protein. In addition, it may also be possible to interfere with the binding of the regulatable protein to target proteins. Other suitable inhibitors will be apparent to the skilled person.

The antibody (or other inhibitors or intrabody) can be administered by a number of methods. One method is set forth by Marasco and Haseltine in PCT WO94/02610, which is incorporated herein by reference. This method discloses the intracellular delivery of a gene encoding the antibody. In one embodiment, a gene encoding a single chain antibody is used. In another embodiment, the antibody would contain a nuclear localization sequence (e.g. an SV40 nuclear localization signal). By this method, one can intracellularly express an antibody, which can block activity of the regulatable protein in desired cells.

Where the present invention provides for the administration of, for example, antibodies to a patient, then this may be by any suitable route. If the tumor is still thought to be, or diagnosed as, localized, then an appropriate method of administration may be by injection direct to the site. Administration may also be by injection, including subcutaneous, intramuscular, intravenous and intradermal injections.

Aptamers can be produced using the methodology disclosed in a U.S. Pat. No. 5,270,163 and WO 91/19813.

Other Inhibitors of Regulatable Protein

Compounds that inhibit the activity of a regulatable protein may also be used. Such compounds include small molecules, e.g., molecules that interact with the active site or a binding site of the protein, e.g., an ATP binding site or substrate binding site. Small molecules can also act as allosteric inhibitors of the protein. Such compounds may be identified according to methods known in the art.

Pharmaceutical Formulations

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters constitute another mode of administration.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The antibodies, nucleic acids or antagonists of the invention may be administered orally, topically, or by parenteral means, including subcutaneous and intramuscular injection, implantation of sustained release depots, intravenous injection, intranasal administration, and the like. Accordingly, antibodies or nucleic acids of the invention may be administered as a pharmaceutical composition comprising the antibody or nucleic acid of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol Registered™, vegetable oils, and the like. One may additionally include suitable preservatives, stabilizers, antioxidants, antimicrobials, and buffering agents, for example BHA, BHT, citric acid, ascorbic acid, tetracycline, and the like. Cream or ointment bases useful in formulation include lanolin, Silvadene Registered™ (Marion), Aquaphor Registered™ (Duke Laboratories), and the like. Other topical formulations include aerosols, bandages, and other wound dressings. Alternatively, one may incorporate or encapsulate the compounds in a suitable polymer matrix or membrane, thus providing a sustained-release delivery device suitable for implantation near the site to be treated locally. Other devices include indwelling catheters and devices such as the Alzet Registered™ minipump. Ophthalmic preparations may be formulated using commercially available vehicles such as Sorbi-care Registered™ (Allergan), Neodecadron Registered™ (Merck, Sharp & Dohme), Lacrilube Registered™, and the like, or may employ topical preparations such as that described in U.S. Pat. No. 5,124,155, incorporated herein by reference. Further, one may provide an antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The amount of antibody, nucleic acid or inhibitor required to treat any particular disorder will of course vary depending upon the nature and severity of the disorder, the age and condition of the subject, and other factors readily determined by one of ordinary skill in the art.

Immunotherapy

In further aspects, the present invention provides methods for using a regulatable protein, e.g., IKKε, or an immunoreactive polypeptide thereof (or DNA encoding the protein or polypeptides) for immunotherapy of cancer in a patient. As used herein, a "patient" refers to any warm-blooded animal, preferably a human. A patient may be afflicted with a disease, or may be free of detectable disease. Accordingly, the regulatable protein or an immunoreactive polypeptide thereof, may be used to treat cancer or to inhibit the development of cancer.

In accordance with this method, the protein, polypeptide or DNA is generally present within a pharmaceutical composition and/or a vaccine. Pharmaceutical compositions may comprise the full length protein or one or more immunogenic polypeptides, and a physiologically acceptable carrier. The vaccines may comprise the full length protein or one or more immunogenic polypeptides and a non-specific immune response enhancer, such as an adjuvant, biodegradable microsphere (PLG) or a liposome (into which the polypeptide is incorporated).

Alternatively, a pharmaceutical composition or vaccine may contain DNA encoding the regulatable protein or an immunogenic polypeptide thereof, such that the full length protein or polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus*-Calmette-Guerrin) that expresses an epitope of a breast cell antigen on its cell surface. In one embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345, 242; WO 91/02805; Berkner, Biotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in published PCT application WO 90/11092, and Ulmer et al., Science 259:1745-1749 (1993), reviewed by Cohen, Science 259:1691-1692 (1993).

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3-24 week period. In one embodiment, 4 doses are administered, at an interval of 3 months, and booster administrations may be given periodically thereafter. Alternative protocols may be appropriate for individual patients. A suitable dose is an amount of polypeptide or DNA that is effective to raise an immune response (cellular and/or humoral) against tumor cells, e.g., kidney tumor cells, in a treated patient. A suitable immune response is at least 10-50% above the basal (i.e. untreated) level. In general, the amount of polypeptide present in a dose (or produced in situ by the DNA in a dose) ranges from about 1 pg to about 100 mg per kg of host, from about 10 pg to about 1 mg, or from about 100 pg to about 1 pg. Suitable dose sizes will vary with the size of the patient, but will typically range from about 0.01 mL to about 5 ml.

The regulatable protein or an immunogenic polypeptide thereof can be used in cell based immunotherapies, i.e. stimulation of dendritic cells with the regulatable protein or fusion with cells expressing the regulatable protein. The modified dendritic cells, once injected into the patient, are a cellular vaccine, where the dendritic cells activate an immune response against the cancer expressing the regulatable protein.

While any suitable carrier known to those of ordinary skill in the art may be employed in the pharmaceutical compositions of this invention, the type of carrier will vary depending on the mode of administration. For parenteral administration, such as subcutaneous injection, the carrier can comprise water, saline, alcohol, a fat, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polyleptic galactide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, Bordella pertussis or *Mycobacterium tuberculosis*. Such adjuvants are commercially available as, for example. Freund's Incomplete Adjuvant and Complete Adjuvant® (Difco Laboratories. Detroit, Mich.) and Merck Adjuvant 65® (Merck and Company, Inc., Rahway, N.J.).

The present description is further illustrated by the following examples, which should not be construed as limiting in any way. The contents of all cited references (including literature references, issued patents, published patent applications and GenBank Accession numbers as cited throughout this application) are hereby expressly incorporated by reference.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2$^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. L. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Contributions of Ras Effector Pathways to Human Cell Transformation

It was previously shown that immortalized human embryonic kidney (HEK) epithelial cells expressing hTERT, LT and ST (HA1E), are rendered tumorigenic by the introduction of H-RAS$^{V12}$ (Hahn et al. (1999) *Nature* 436, 117-122). Activation of Ras stimulates many effector pathways including, but not limited to, the MAPK, PI3K and RALGDS pathways (Downward (2003) *Nat. Rev. Cancer* 3, 11-22). However, it was likely that only a subset of these pathways participate directly in H-RAS$^{V12}$-induced transformation. Since activating mutations are found in several members of the MAPK and PI3K pathways in many human cancers, it was reasoned that the co-activation of these two pathways might be sufficient to replace H-RAS$^{V12}$ in transformation. To test this hypothesis, the MAPK and PI3K pathways were manipulated in a combinatorial manner in HA1E cells.

To activate the PI3K pathway, one of three mutant alleles was expressed: myristoylated (myr), and therefore constitutively active, alleles of PIK3CA p110α (Klippel et al. (1996) *Mol. Cell. Biol.* 16, 4117-4127) (myr-110α) or AKT1 (myr-AKT) (Kohn et al. (1996) *J. Biol. Chem.* 271, 21920-21926); or a short hairpin RNA (shRNA) targeting PTEN (Boehm et al. (2005) *Mol. Cell. Biol.* 25, 6464-6474). To activate the MAPK pathway, one of three mutant alleles was expressed: an activated allele of CRAF (C-Raf 22W) (Stanton et al. (1989) *Mol. Cell. Biol.* 9, 639-647); the BRAF$^{E600}$ allele (Davies et al. (2002) *Nature* 417, 949-954); or a constitutively active MEK1$^{D218,D222}$ allele (MEKDD) (Brunet et al. (1994) *Oncogene* 9, 3379-3387). Using these reagents, sixteen cell lines expressing all possible combinations of these mutant alleles were created. All of these cell lines were confirmed to stably express each of the activated alleles, either singly or in pairwise combinations, and the ability of these cells to grow in an anchorage independent (AI) manner or to form tumors in immunodeficient animals was analyzed (TABLE 2).

When introduced singly, none of the mutant alleles promoted AI colony formation (TABLE 2). However, certain combinations of activated alleles were found to substitute for H-RAS$^{V12}$ to render these immortalized HEK cells tumorigenic (TABLE 2). Specifically, activation of the MAPK pathway by either BRAF$^{E600}$ or MEKDD expression together with activation of the PI3K pathway by myr-AKT expression induced AI growth indistinguishable from that induced by H-RAS$^{V12}$ (TABLE 2, upper panel and FIG. 1). Surprisingly, while either BRAF$^{E600}$ or MEKDD cooperated with myr-AKT to induce AI growth, only cells expressing the MEKDD+myr-AKT combination induced tumor growth comparable to that observed in cells expressing H-RAS$^{V12}$ (TABLE 2, lower panel and FIG. 1). These observations indicate that co-activation of specific members of the MAPK and PI3K pathways suffices to replace H-RAS$^{V12}$ in human cell transformation. In these HEK cells, co-expression of MEKDD and myr-AKT most closely recapitulated the AI growth and tumorigenicity phenotypes induced by H-RAS$^{V12}$ (FIG. 1).

Example 2

Identification of Transforming Kinases

This approach not only identified specific combinations of activated members of the MEK and PI3K pathways that replace H-RAS$^{V12}$ in HEK cell transformation, but also established an experimental platform to discover other transforming genes. This work was therefore extended by screening a large collection of genes to identify those that can substitute for myr-AKT. Because phosphorylation plays a key role in Ras signaling, it was hypothesized that other kinases might participate in PI3K-induced transformation.

Figure 2:
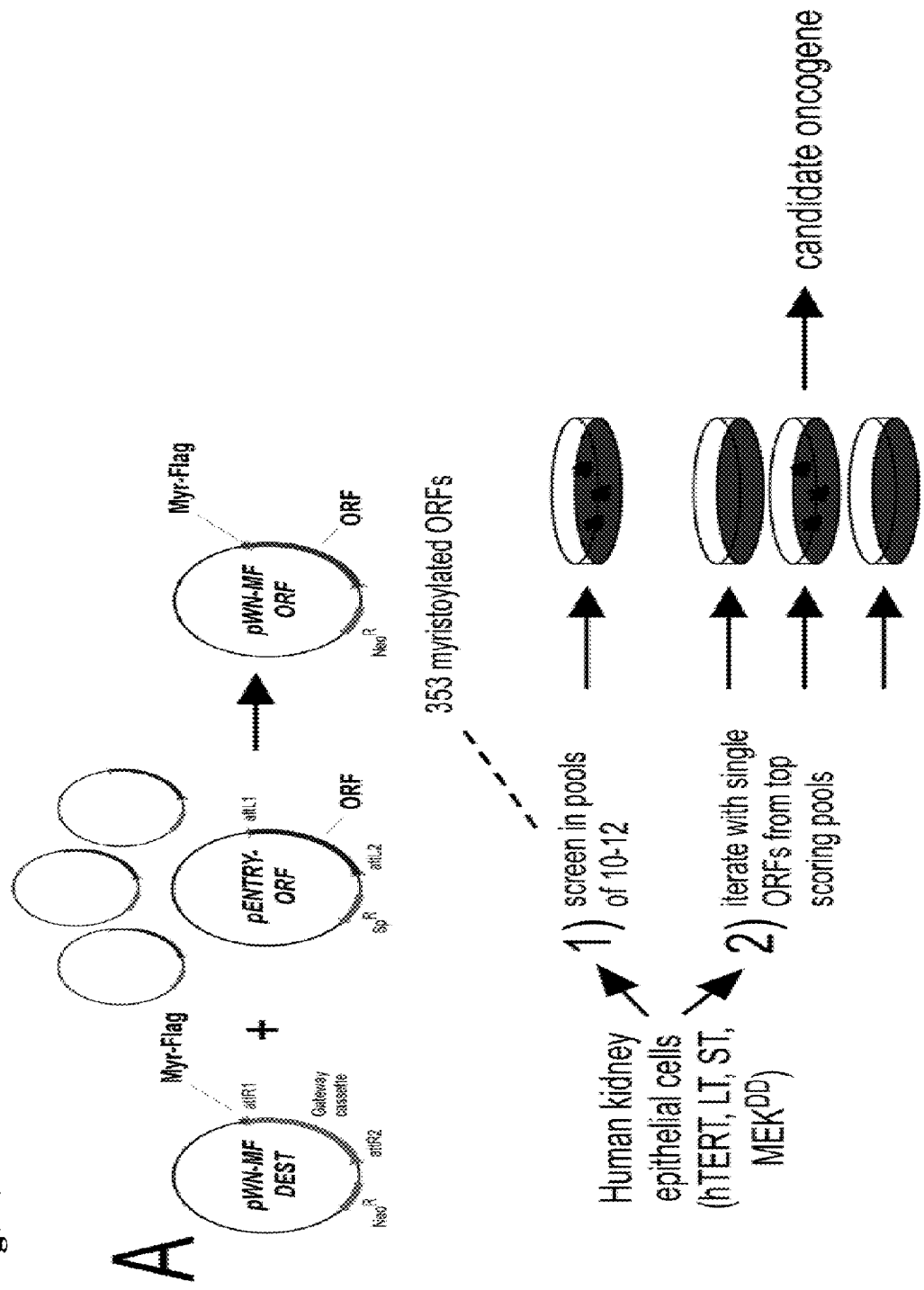
FIGS. 2A-C show the results of identifying putative oncogenes using a myristoylated kinase library.
FIG. 2D shows tumor formation by IKBKE in HA1E-M cells. Tumorigenicity is indicated as the number of tumors formed/number of tumor sites injected and shown above the bars for each cell line.
Figure 2:
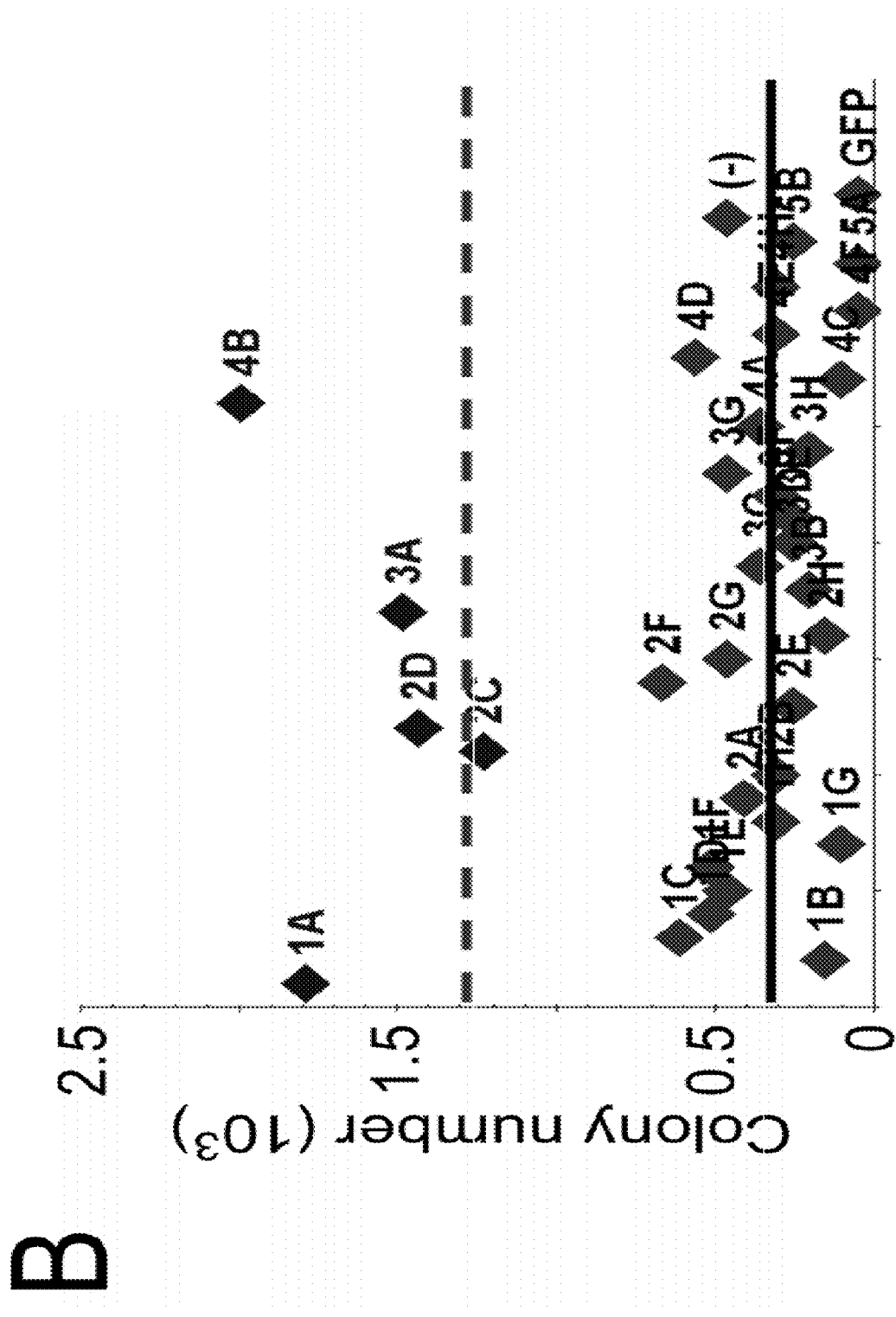
Figure 2:
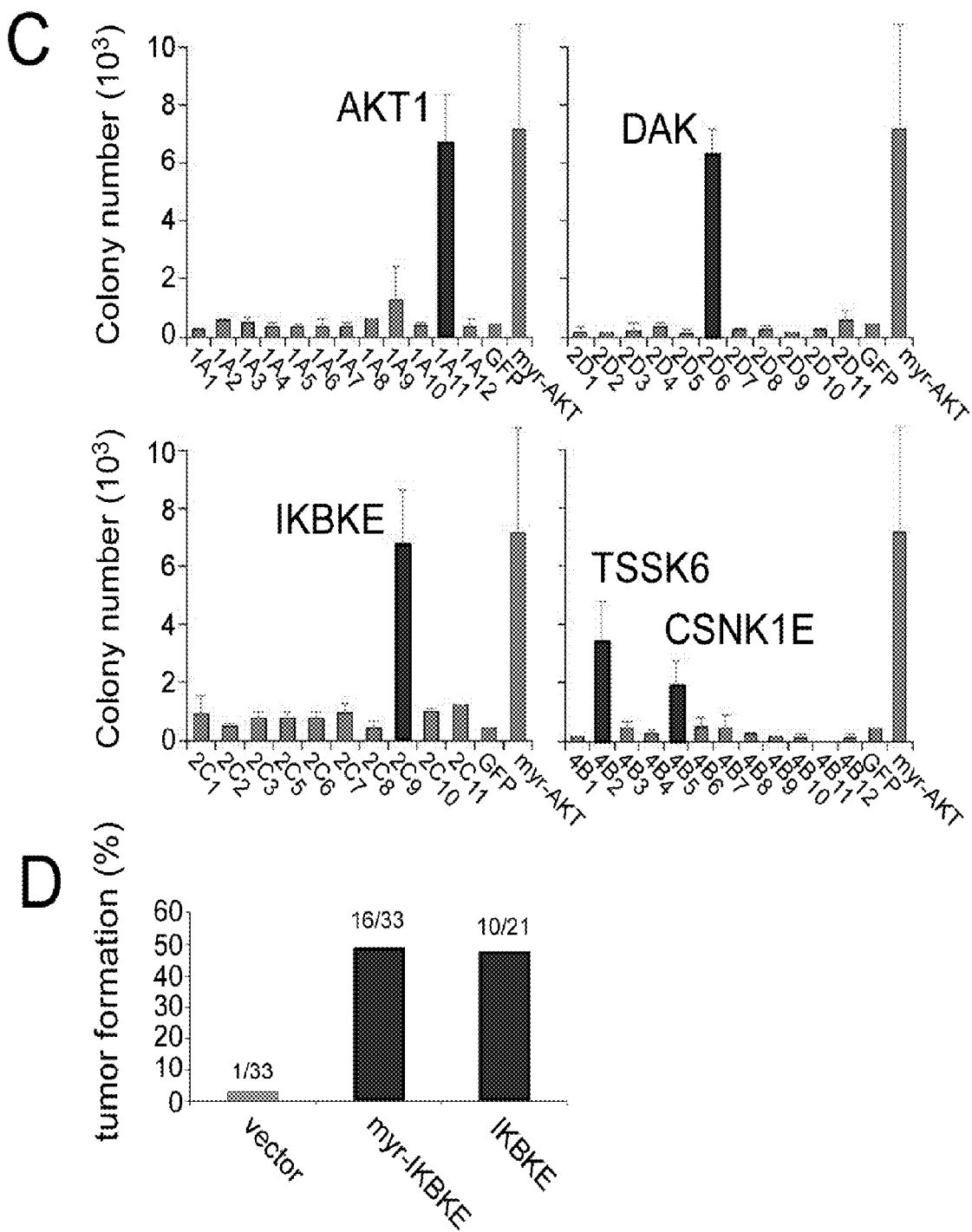
Figure 7:
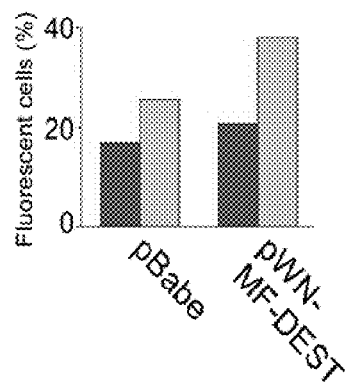
FIGS. 7A-B shows the results of pWN-MF-DEST vector validation.
Figure 7:
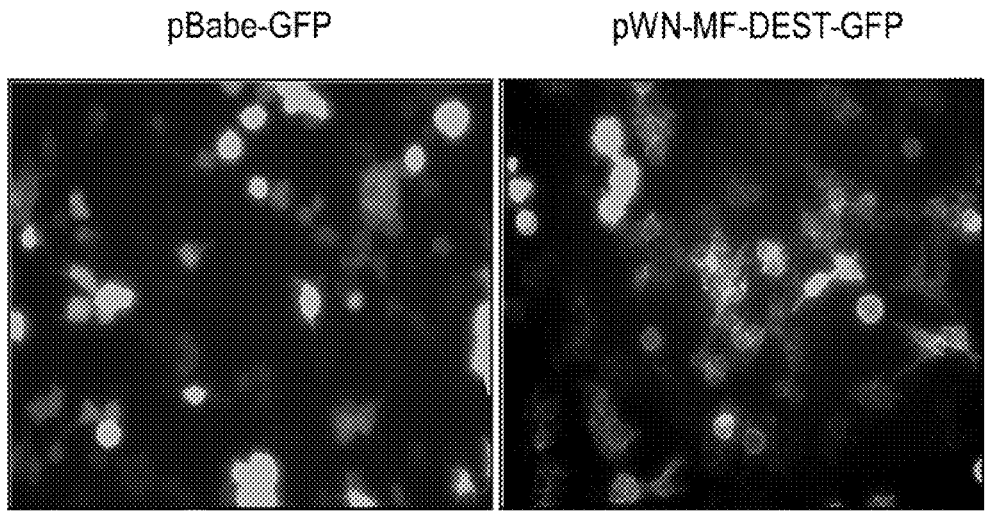

To identify such kinases, a library of 354 human kinases and kinase-related open reading frames (ORFs), including 256 kinases, was cloned into Gateway®-compatible entry vectors (Rual et al., (2004) *Genome Res.* 14, 2128-2135). Because membrane recruitment via the addition of a myr sequence activates both the PI3K p110α subunit and AKT (Klippel et al. (1996) *Mol. Cell. Biol.* 16, 4117-4127; Kohn et al. (1996) *J. Biol. Chem.* 271, 21920-21926), a Gateway®-compatible retroviral destination vector, pWN-MF-DEST, was created which adds a myr sequence and a FLAG-epitope tag (MF) to each introduced ORF. It was confirmed that this destination vector and myr tag were functional (FIG. 7). Each ORF was subsequently transferred individually into pWN-MF-DEST (FIG. 2A).

Using the library of 354 myristoylated ORFs, a screen for genes that could replace myr-AKT and induce cell transformation was performed. Pools consisting of 10-12 unique ORFs were introduced into immortal but non-tumorigenic HEK cells expressing MEKDD (HA1E-M). Several pools reproducibly induced colony formation more than two standard deviations greater than the median number of colonies observed in the controls (FIG. 2B). To determine the identity of the specific kinases in these pools responsible for AI growth, cell lines were created that express individual kinases from each of such pools (FIG. 2C). Of the four pools analyzed in this manner, three contained one transforming kinase gene, and one pool, contained two transforming kinase genes. Each of these kinase genes (AKT1, IKBKE, DAK, TSSK6 and CSNK1E) also induced tumor formation (FIG. 2D). Since it was previously shown that myr-AKT cooperates with MEKDD to transform these immortalized cells, the identification of AKT1 in this screen validated this screening approach. Thus, using a library of myristoylated kinases in retroviral vectors, four novel kinases were identified that cooperate with activated MEK1 to replace H-RAS$^{V12}$ in human cell transformation.

Example 3

Figure 3:
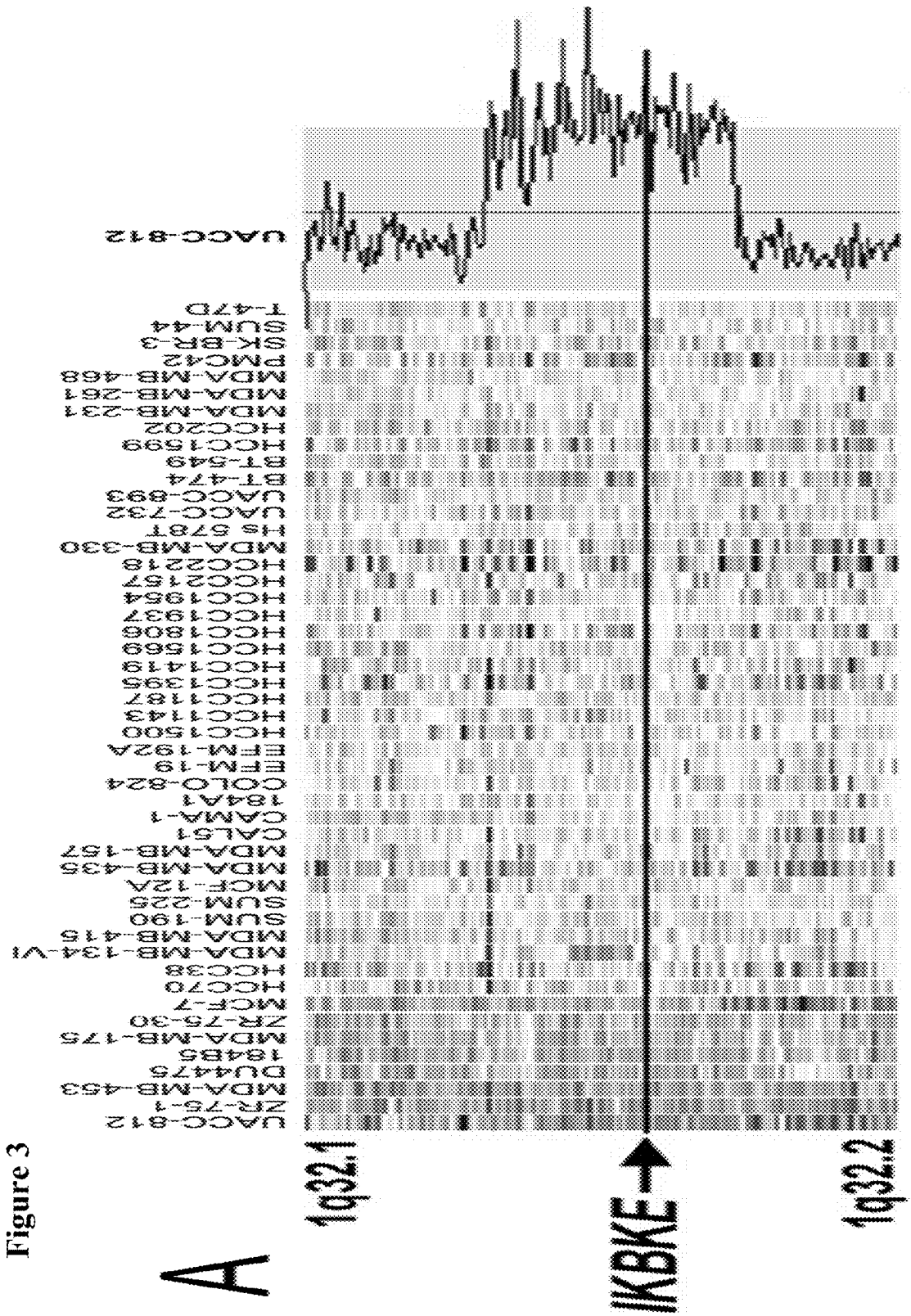
FIGS. 3A-F show that IKBKE is amplified in breast cancer cell lines and patient-derived tumor samples.
FIG. 3G shows immunoblotting for IKKε in the indicated breast cancer cell lines or HMEC-M cells expressing myr- or wild-type IKBKE.
Figure 3:
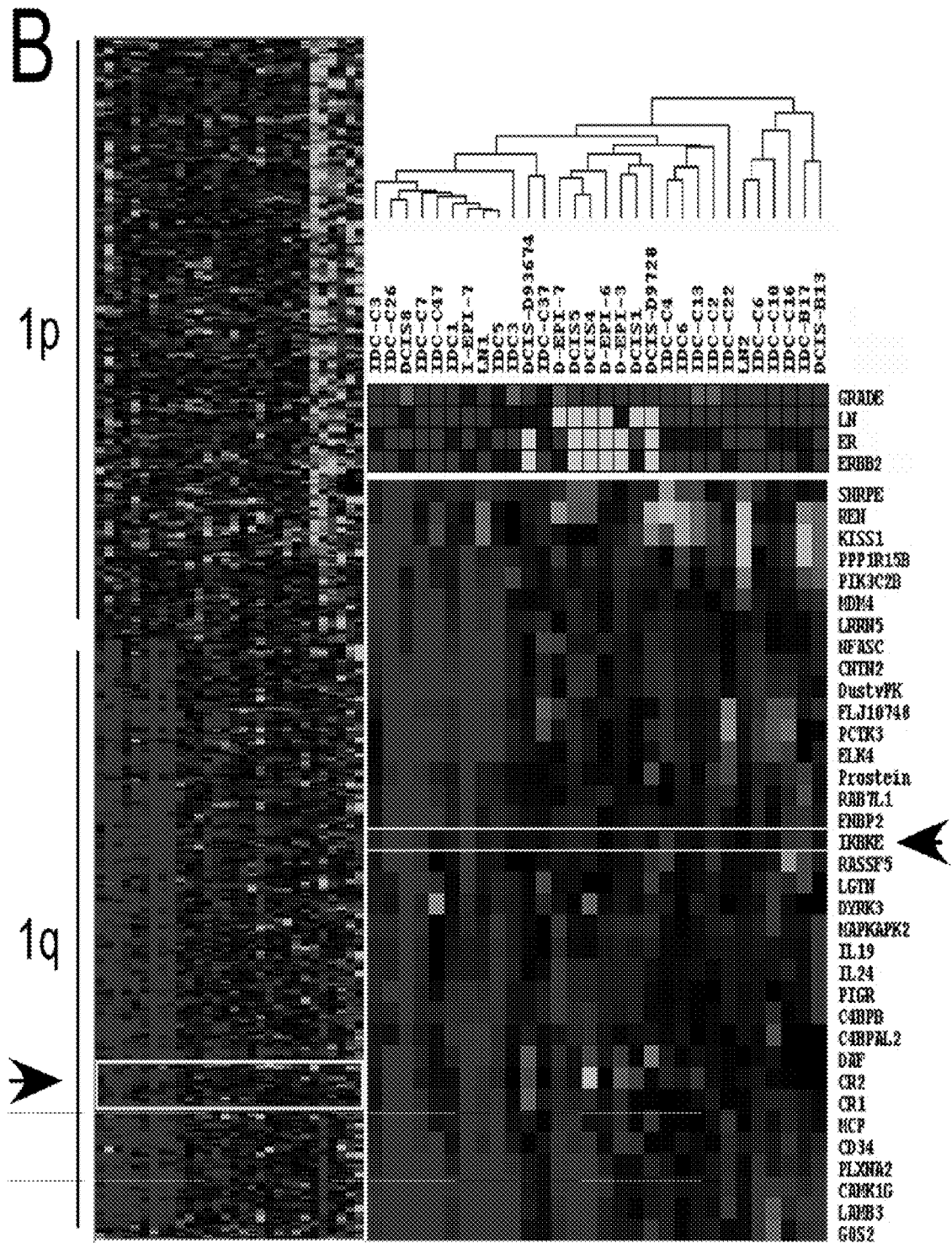
Figure 3:
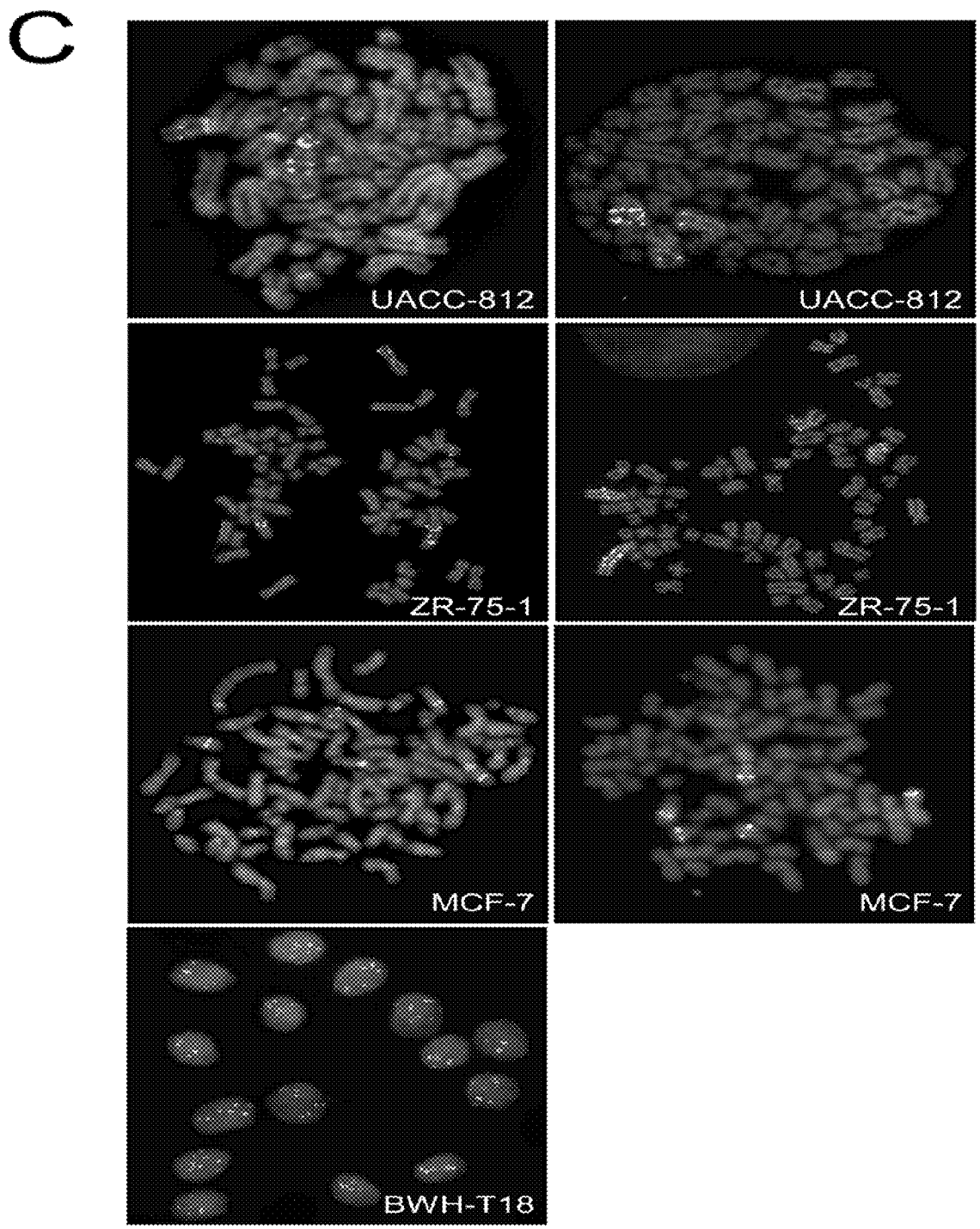
Figure 3:
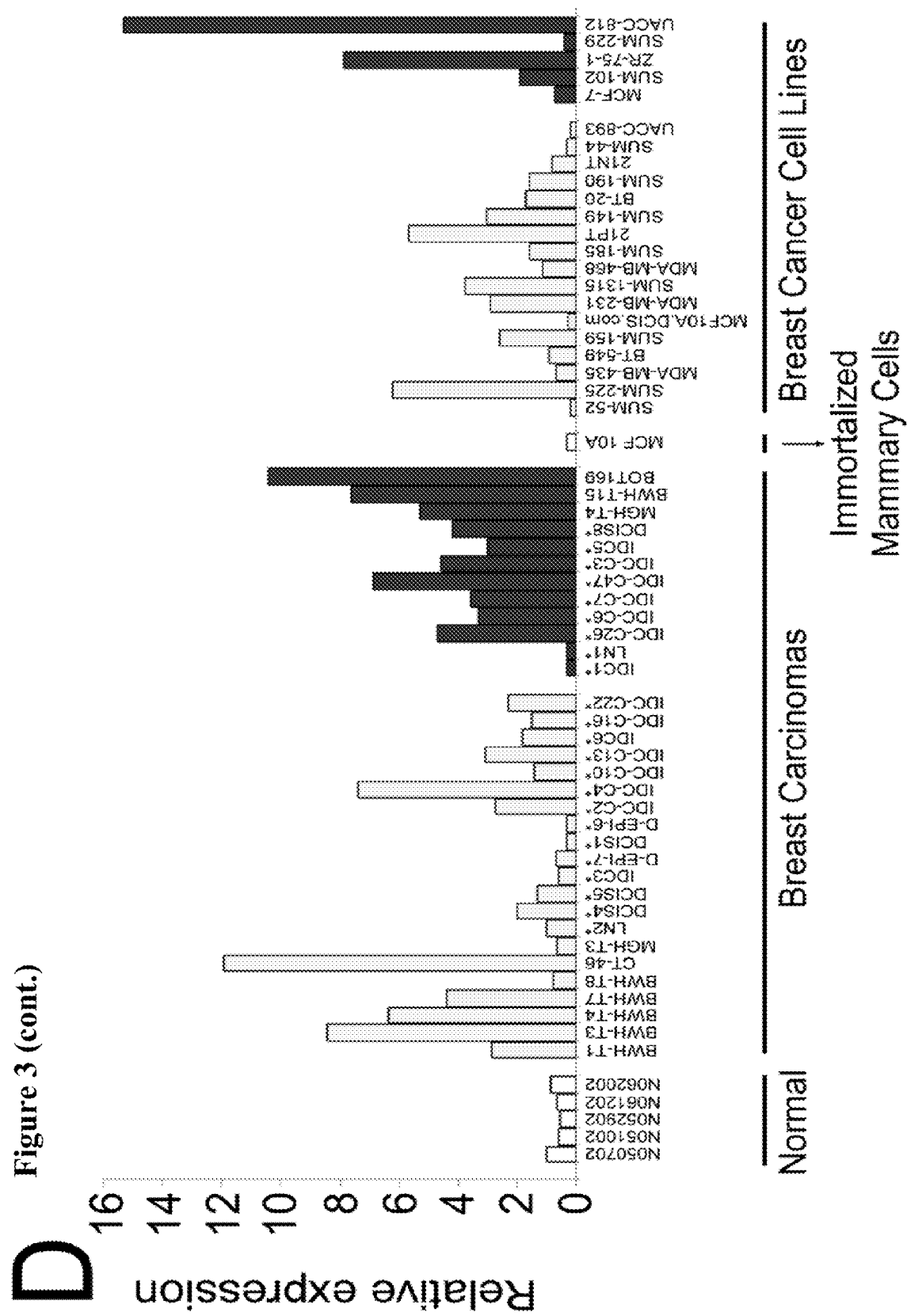
Figure 3:
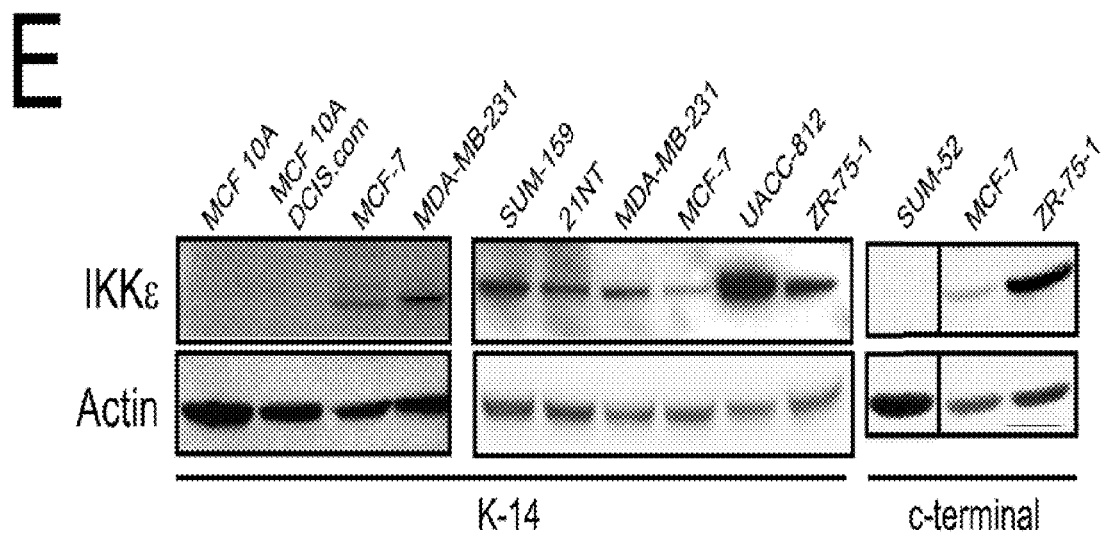
Figure 3:
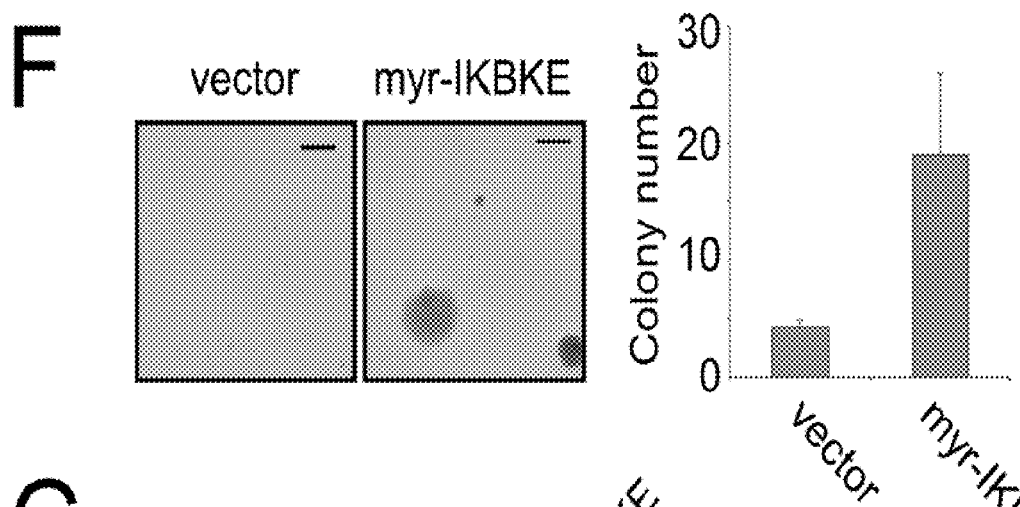
Figure 3:
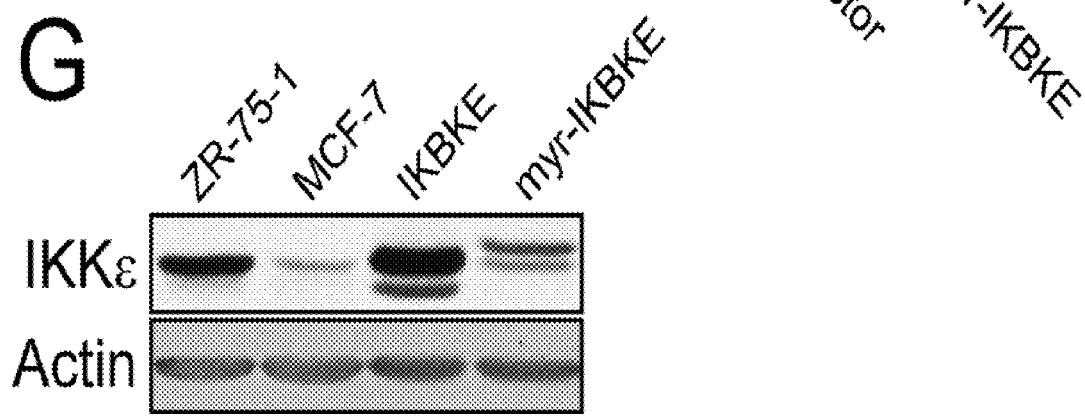

Amplification of IKBKE in Breast Cancer Cell Lines and Patient-Derived Tumor Samples It was next explored whether any of these kinases are altered in human cancers. First, high density SNP arrays were used to identify areas of copy number gain or loss in 179 cell lines representing a wide spectrum of cancer types (Garraway et al. (2005) *Nature* 436, 117-122). Clear evidence of amplifications of the loci encoding DAK, TSSK6 or CSNK1E in any of the cell lines was not found. In contrast, copy number gain or amplification of 1q32 involving the IKBKE locus was found in 8 of 49 (16.3%) breast cancer cell lines (FIG. 3A). Indeed, copy number gain of 1q is the most common and earliest genetic alteration in breast cancers (Rennstam et al. (2003) *Cancer Res.* 63, 8861-8868).

It was next investigated whether IKBKE was similarly amplified in primary human breast cancer specimens by performing array comparative genome hybridization (aCGH) analyses on 30 breast tumors representing different clinicopathological stages (Yao et al., (2006) *Cancer Res.* 66, 4065-4078). These studies also revealed a region of recurrent copy number gain involving the IKBKE locus on chromosome 1q in 10 of 30 breast tumors (FIG. 3B). Four of the 10 ductal carcinoma in situ (DCIS) cases analyzed showed copy number gain of IKBKE, suggesting that amplification of this locus is an early event in the development of some breast cancers. An association of IKBKE copy number gain with estrogen receptor or Her2/neu status, or with the presence of lymph node involvement at diagnosis was not found. In addition, the IKBKE gene in 28 breast tumors and 19 breast cancer cell lines was sequenced and no evidence of somatic mutations was found, corroborating recent sequence efforts from other groups (Bamford et al. (2004) *Br. J. Cancer* 91, 355-358).

To confirm that the region of copy number gain at 1q32 involves IKBKE, fluorescence in situ hybridization (FISH) was performed on several breast cancer cell lines and a primary breast tumor containing an amplification of 1q32 (FIG. 3C). Up to 10 copies of IKBKE in the UACC-812 and ZR-75-1 breast cancer cell lines and 5 copies of IKBKE in MCF-7 cells were found. One of the DCIS breast tumors, BWH-T18, harbored 5 copies of the IKBKE locus in the majority of nuclei (FIG. 3C).

It was also investigated whether these DNA copy number changes corresponded to increases in IKBKE transcript and protein levels. Indeed, Serial Analysis of Gene Expression (SAGE), quantitative RT-PCR, and immunoblotting analyses confirmed that IKBKE (IKKε) is overexpressed in cell lines and breast tumors that exhibited 1q32 gain, suggesting that IKBKE is one target of this amplicon (FIG. 3D and FIG. 3E). In addition, it was found that an additional 13/17 cell lines (76.5%) and 10/21 breast cancers (47.6%) showed increased expression (>2 fold) of IKBKE transcripts in the absence of 1q32 copy number changes. Utilizing two different IKKε antibodies, the observed protein levels correlated with the transcript levels (FIG. 3D and FIG. 3E), and UACC-812 and ZR-75-1 cells, which harbor 1q32 amplifications (FIG. 3A and FIG. 3C), showed the highest levels of IKKε of any cell line analyzed (FIG. 3E).

Although initial experiments were performed in immortalized HEK cells, it was also found that the introduction of IKBKE transforms human mammary epithelial cells (HMEC) expressing hTERT, the SV40ER and MEKK (HMEC-M) (FIG. 3F). In addition, since 1q32 amplifications result in increased levels of wild-type (WT) IKBKE, it was examined whether forced expression of the WT, non-myr IKBKE allele also rendered cells tumorigenic. It was found that cells expressing WT IKBKE at levels found in human cancer cells exhibited a similar capacity for tumorigenicity (FIG. 2D and FIG. 3G), confirming that the allele amplified in breast cancer specimens is transforming. Together, these observations identified IKBKE as a transforming kinase that is amplified and overexpressed in a substantial fraction of breast cancer cell lines and primary breast tumors.

Example 4

Consequences of Suppressing IKBKE in Breast Cancer Cells

Because the findings described above implicate IKBKE as a breast cancer oncogene, the question of whether breast cancer cells are functionally dependent on IKKε expression was asked. The upregulated expression of many oncogenes renders cancer cells unusually dependent upon the continued function of the oncogene for cell proliferation or viability. This property of oncogenes, termed oncogene addiction, provides a rationale for targeting oncogenes therapeutically. To determine whether the presence of IKBKE amplifications and overexpression induces oncogene addiction, the effects of RNA interference (RNAi) targeting IKBKE and other genes were examined.

As part of a separate project to systematically discover genes essential for cancer cell viability, the shRNA library developed by The RNAi Consortium (TRC) (Moffat et al. (2006) *Cell* 124, 1283-1298) was used to screen a large collection of genes required for the proliferation and/or viability of cancer cell lines. As part of this effort, the MCF-7 breast cancer cell line was screened, as well as several additional human cancer cell lines, with 6,144 shRNAs targeting 1200 genes, including 93% of known human kinase genes. The results from the screening of MCF-7 cells were of particular relevance to the present study, because this breast cancer cell line harbors a 1q32 copy number gain (FIG. 3A and FIG. 3C) that results in a modest 2.5 fold increase in IKBKE transcript levels compared to immortalized MCF10A cells (FIG. 3D). Examining the data from this screen, it was found that three of five shRNA targeting IKBKE compromised cell proliferation and viability (FIG. 4A, FIG. 4C, and FIG. 4D). It was found that the level of IKKε suppression by these 5 shRNA correlated with the observed decrease in cell proliferation and viability in MCF-7 cells (FIG. 4A, FIG. 4C, and FIG. 4D). These observations indicate that IKBKE is required for cell proliferation and survival of MCF-7 breast cancer cells.

This RNAi screen also included constructs targeting three of the other four genes that emerged from the gain-of-function screen (AKT1, CSNK1E and TSSK6). Similar to the results from shRNA targeting IKBKE, shRNA targeting AKT1 or CSNK1E also resulted in inhibition of MCF-7 cell proliferation.

The data generated in the high throughput RNAi was next examined in order screen was examined in order to determine whether any other kinase encoded within the 1q32 amplicon was similarly required for MCF-7 viability. A minimally amplified region (5.6 Mb) containing IKBKE in the UACC-812 breast cancer cell line (FIG. 3A). This minimally amplified region contains 9 additional kinase genes. However, RNAi-mediated suppression of these other kinase genes failed to induce a statistically significant decrease in viability of MCF-7 cells (FIG. 4B). Three of four shRNA targeting NUAK2 partially inhibited the proliferation of MCF-7 cells but failed to satisfy the criteria employed in the high throughput RNAi screen. Although these observations do not eliminate the possibility that other genes within this 1q32 amplicon may cooperate with IKBKE to induce transformation, these findings suggest that IKBKE is a key target of the 1q32 amplification in breast cancer cell lines and tumors.

To confirm that these observations in MCF-7 cells applied to other breast cancer cell lines that show IKBKE amplifications, the ZR-75-1 breast cancer cell line, which exhibits high-level amplification of IKBKE (FIG. 3A and FIG. 3C), was examined. It was found that inhibition of IKBKE expression in this cell line also compromised viability (FIG. 4C). In contrast, shRNA-mediated suppression of IKBKE failed to affect viability in PC3 prostate cancer cells, hTERT-expressing HMECs or the MCF10A.DCIS.com breast cancer cell line, all of which do not harbor amplifications of IKBKE (FIG. 4C). Corroborating these qualitative observations, it was found that suppression of IKBKE in MCF10A.DCIS.com or PC3 cancer cells inducted only a small increase in doubling time (9.1%-28.0%) over 11 days (FIG. 4D) while suppression of IKBKE in MCF-7 and ZR-75-1 cells increased doubling time by 80.6%-114.5% (FIG. 4D). These observations suggested that IKBKE is essential for proliferation in breast cancer cell lines that show increased IKBKE copy number.

Figure 8:
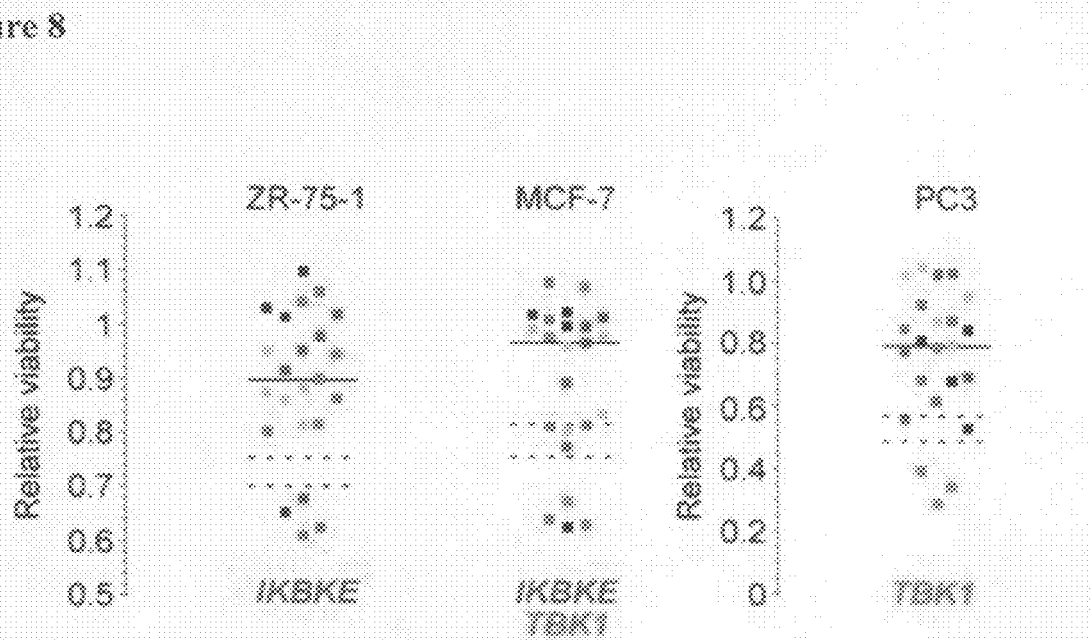
FIG. 8 shows the effects of suppressing the expression of IKK family members. ZR-75-1, MCF-7 or PC3 cells were infected with shRNA constructs targeting IKBKA (IKKα), IKBKB (IKKβ), IKBKG (IKKγ, NEMO), IKBKE, and TBK1 and viability was determined. Analysis and dotted lines as in FIG. 4B. shRNAs are color coded according to their target (IKBKE-red, TBK1-teal, IKBKA-black, IKBKB-gold, IKBKG-green). Relative viability was calculated by normalizing to luminescence scores obtained from the mean of 7 parallel cultures infected with control shRNA constructs (targeting GFP). To determine if a given gene was essential it was required that more than one shRNA construct targeting the gene decreased viability. Essential genes are indicated below each cell line.

IKKε is a member of a family of five distinct but closely related proteins, the IκB kinase (IKK) family, consisting of IKKα, IKKβ, IKKγ, IKKε, and TBK1. Since IKKε function partly overlaps with other IKKs (Fitzgerald et al. (2003) *Nat. Immunol.* 4, 491-496; Peters et al. (2000) *Mol. Cell.* 5, 513-522; Sharma et al. (2003) *Science* 300, 1148-1151), it was next determined whether the proliferation of ZR-75-1, MCF-7, or PC3 cells depended upon expression of any of the other IKK family members. Specifically, five distinct shRNA targeting each of these IKK family members were introduced into MCF-7, ZR-75 and PC3 cells. It was required that more than one shRNA construct targeting the gene to decrease viability and it was found that IKKε was the only IKK family member required for proliferation of ZR-75-1 cells, while both IKKε and TBK1 were required for the proliferation of MCF-7 cells (FIG. 8). Suppression of TBK1, but not IKKε, inhibited the proliferation of PC3 cells. Taken together, these observations implicate IKBKE as an essential oncogene in breast cancer cell lines harboring amplifications of 1q32 and are reminiscent of similar findings made in cell lines harboring other oncogenes such as BCR-ABL and EGFR, which also appear to render oncogene-expressing cells particularly dependent upon their expression (Weinstein and Joe (2006) *Nat. Clin. Pract. Oncol.* 3, 448-457).

Example 5

Consequences of IKBKE Amplification and Overexpression

Recent work implicates IKKε in the innate immune response to viral infections, as it activates the interferon pathway in part by stimulating the activity of the transcription factor IRF3 (Fitzgerald et al. (2003) *Nat. Immunol.* 4, 491-496; Sharma et al. (2003) *Science* 300, 1148-1151). It was tested whether cells expressing IKBKE displayed evidence of increased IRF3 transcriptional activity and a 3-5-fold activation of the IRF3-responsible interferon-regulated promoter element (ISRE) of the IFIT2 gene in HA1E-M cells expressing either the myr or WT allele of IKBKE (FIG. 9A) was found. HA1E-M and HMEC-M cells expressing these IKBKE alleles also showed increased transcription of two known interferon responsive genes, IFNB1 and CCL5 (encoding RANTES) (FIG. 9B and FIG. 9C).

Figure 9:
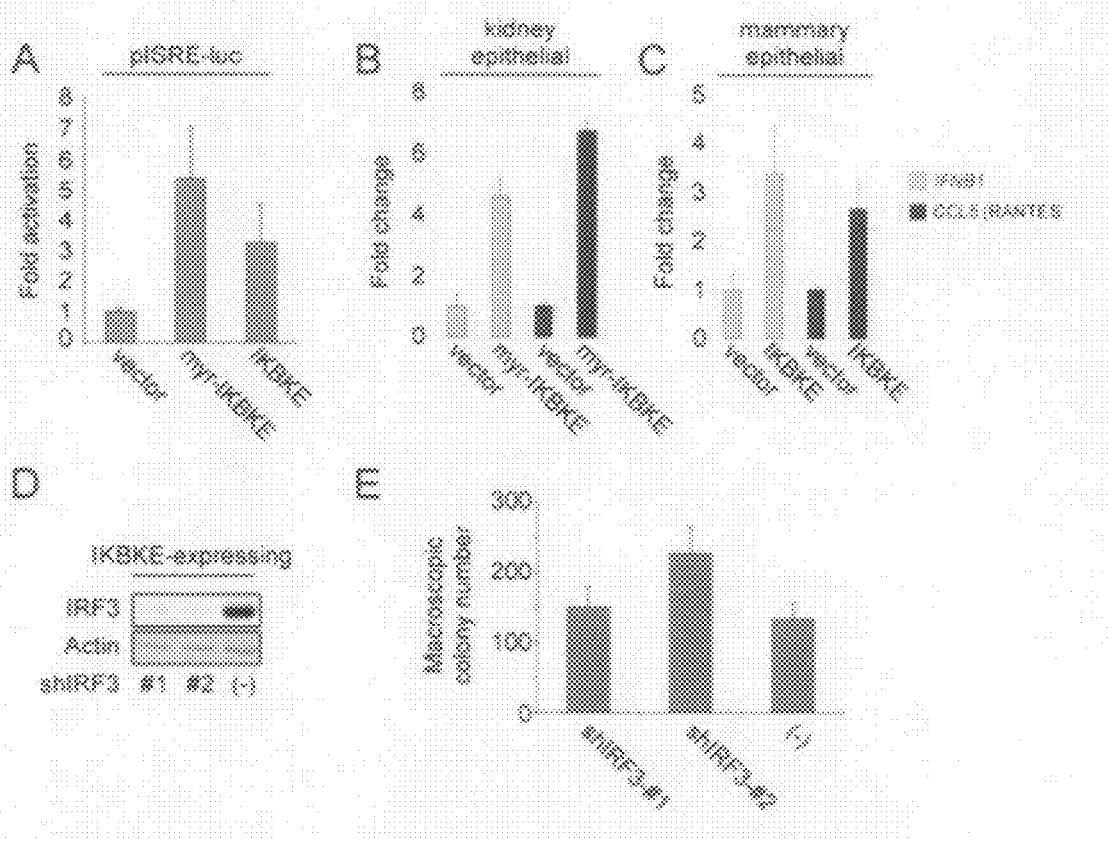
FIGS. 9A-9E show that IKBKE activates the interferon pathway.

To determine whether this activation of interferon-responsive promoters was required for transformation induced by IKBKE, IRF3-specific shRNA constructs were introduced into transformed HA1E-M cells expressing myr-IKBKE (FIG. 9D). Suppression of IRF3 failed to suppress AI growth (FIG. 9E). These observation suggested that, although the physiologic function of IKBKE involves activation of interferon responses, this activity of IKBKE may not be essential for transformation.

IKBKE has also been reported to activate the NF-κB pathway (Peters et al. (2000) *Mol. Cell* 5, 513-522). It was therefore next determined whether the transforming activity of IKBKE is mediated by NF-κB. It was determined whether the expression of IKBKE destabilized the cytoplasmic pool of IκBα. HA1E-M cells expressing myr-IKBKE displayed a 43% reduction in cytoplasmic IκBα compared to levels observed in cells expressing a control vector (FIG. 5A and FIG. 5B). Moreover, even when IκBα was overexpressed in these IKBKE-expressing cells, increased IκBα protein expressed was not observed (FIG. 5C), indicating that IKKε effectively drives IκBα degradation. One consequence of IκBα degradation is the translocation of NF-κB transcription factors from the cytoplasm to the nucleus. Consistent with this expectation, it was found that HA1E-M cells expressing myr-IKBKE displayed a 32% reduction in cytoplasmic NF-κB p50 (FIG. 5A and FIG. 5B), and 71% of these cells displayed nuclear NF-κB p50 compared to 8% in cells harboring a control vector (FIG. 5D and FIG. 5E).

It was also tested whether overexpression of IKBKE induced NF-κB transcriptional activity. HA1E-M cells expressing myr-IKBKE exhibited a 5-fold higher level of NF-κB transcriptional activity compared to cells expressing a control vector, as assessed by measuring the activity of a synthetic NF-κB reporter gene (FIG. 5F). To confirm that IKBKE activated the expression of endogenous NF-κB target genes, the expression levels of 9 NF-κB target genes was measured in HA1E-M or HMEC-M cells expressing myr- or WT IKBKE, respectively. IKBKE induced increased expression of all of these transcripts compared to cells expressing a control vector (FIG. 6G and FIG. 6H). Since cyclin D1 is overexpressed in over 50% of breast cancers (Bartkova et al. (1994) *Int. J. Cancer* 57, 353-361), it was examined whether the observed increases in CCND1 mRNA levels corresponded to increased cyclin D1 protein levels. Indeed, both HA1E-M or HMEC-M cells expressing myr-IKBKE showed substantially elevated levels of cyclin D1 (FIG. 5I). These data demonstrated that IKBKE activates the NF-κB pathway in two epithelial cell types.

To determine whether activation of the NF-κB pathway is necessary for transformation induced by IKBKE, NF-κB activity was inhibited in IKBKE-transformed HEK cells by expressing a mutant (MUT) "super-repressor" allele of IκBα harboring two amino acid substitutions (S32A/S36A), which renders this MUT. IκBα resistant to phosphorylation and degradation (Brown et al. (1995) *Science* 267, 1485-1488). Expression of MUT IκBα in IKBKE-transformed HEK cells increased doubling times (FIG. 5J) and suppressed AI colony formation by 90.7% compared to cells infected with a control vector (FIG. 5K). In summary, these results implicate the activation of the NF-κB pathway in IKBKE-mediated cell transformation.

IKBKE was initially identified as a kinase that replaced AKT1 in cellular transformation (FIG. 2A). Since AKT has also been reported to activate the NF-κB pathway (Ozes et al. (1999) *Nature* 401, 82-85; Romashkova and Makarov (1999) *Nature* 401, 86-90), it was next determined if the NF-κB pathway is similarly required for AKT-dependent transformation. Introduction of the MUT IκBα allele increased the doubling time of HEK cells transformed by AKT (FIG. 5J) and suppressed AI growth by 73.9% (FIG. 5K). It was next examined whether IKBKE contributed to cell transformation induced by AKT. Indeed, it was found that suppression of IKBKE by two different shRNA constructs increased doubling times by 20.0-59.0% and inhibited the capacity of AKT-transformed HEK to proliferate and grow in an AI manner (FIG. 5L). In aggregate, these observations implicate aberrant activation of the NF-κB pathway by IKBKE as a critical step in cell transformation induced by AKT. Finally, it was determined whether IKBKE regulates the NF-κB pathway in breast cancer cell lines and patient-derived breast cancer tissue samples. Changes in NF-κB gene expression after IKBKE suppression in ZR-75-1 and MCF-7 breast cancer cells were examined and it was found that the expression of two IKBKE-induced NF-κB regulated genes, MMP9 and BCL2 (FIG. 5G and FIG. 5H), decreased upon suppression of IKBKE (FIG. 6A). Breast cancer cell lines harboring the 1q32 amplification showed increased expression of these genes compared to a breast cancer cell line that lacks IKKε expression (SUM52, FIG. 3E, right panel) (FIG. 6B and FIG. 6C). It was confirmed that these observations in cell lines also extended to primary breast cancer specimens. Since IKKε has recently been shown to induce nuclear accumulation of the NF-κB family member c-REL (Harris et al. (2006) *J. Immunol.*, 177, 2527-2535), immunohistochemistry (IHC) was performed to detect IKKε and c-REL in an independent set of 20 breast cancer tissue samples. It was found that 7/20 (35%) of these breast cancer specimens showed increased expression of IKKε (FIG. 6D and FIG. 6E), confirming observations in the initial breast cancer specimens (FIG. 3B and FIG. 3D). In addition, it was found that 7 of 7 (100%) breast tumors that exhibited increased IKKε expression also displayed nuclear c-REL. In contrast, c-REL was expressed at very low levels or was predominantly located in the cytoplasm in 12 of 13 (92%) of breast tumors that do not exhibit increased IKKε expression (FIG. 6D and FIG. 6E). This correlation between IKKε expression and nuclear localization of c-REL was statistically significant (p<0.0084). Taken together, these observations demonstrated that IKKε activates the NF-κB pathway in breast cancer. Moreover, while the clinical evidence for IKBKE gain-of-function in cancer comes from the amplification or overexpression of this gene, IKBKE and other candidates were only scored in the oncogenic transformation assay using the myr-kinase library. Overexpression of the cDNA for IKBKE failed in the primary screen. No candidate gene was scored when either a cDNA or ORF library was tested in the primary screen, suggesting that activated kinase library provides more robust signals.

Example 6

Materials and Methods for Examples 1-5

A. Cells Culture and Retroviral Infection

HEK cells (Hahn et al. (1999) *Nature* 436, 117-122) and HMECs expressing hTERT (Elenbaas and Weinberg (2001) *Exp. Cell Res.* 264, 169-184) have been described. To introduce or suppress specific genes, retroviral (pBabe, pWzl, pMKO) (Boehm et al., (2005) Mol. Cell. Biol. 25, 6464-6474; Morgenstern and Land (1990) *Nucleic Acids Res.* 18, 3587-3596) or lentiviral (pLKO) (Moffat et al., (2006) Cell 124, 1283-1298) vectors were used. Retroviruses and lentiviruses were generated as described (Boehm et al., (2005) Mol. Cell. Biol. 25, 6464-6474; Moffat et al., (2006) Cell 124, 1283-1298). Growth conditions for HEK cells have been described (Hahn et al., (2002) *Mol. Cell. Biol.*, 22, 2111-2123). HMEC cells were maintained in 1:1 DMEM:F12 (Invitrogen Corp., Carlsbad, Calif.) supplemented with 10 ng/mL epidermal growth factor (Sigma-Aldrich, St. Louis, Mo.), 0.5 μg/mL hydrocortisone (Sigma-Aldrich, St. Louis, Mo.), and 10 μg/mL insulin (Sigma-Aldrich, St. Louis, Mo.). Tumor specimens and breast cancer cell lines were obtained as described (Yao et al., (2006) *Cancer Res.* 66, 4065-4078)

B. Myristoylated Kinase Library

ORFs were cloned into Gateway® compatible pEntry vectors by performing site-specific BP recombination reactions as described (Rual et al., (2004) *Genome Res.* 14, 2128-2135). pWzl-Neo-Myr-Flag DEST (pWN-MF-DEST) was created by inserting an N-terminal myristoylation-FLAG tag and the Gateway® selectable cassette into the pWzl-Neo retroviral vector (Morgenstern and Land (1990) *Nucleic*

Acids Res. 18, 3587-3596). To create specific pWN-MF-ORF vectors, site-specific LR recombination reactions were performed individually, as described (Rual et al., (2004) Genome Res. 14, 2128-2135).

C. Other Vectors Used in this Study pBabe-Puro-cRAFw22, pBabe-Puro-BRAF$^{E600}$, pBabe-Puro-MEKDD, and pBabe-HcRed-MEKDD were created by introducing the cRAFw22 allele (Stanton et al. (1989) Mol. Cell. Biol. 9, 639-647), the BRAF$^{E600}$ allele (Davies et al. (2002) Nature 417, 949-954) and the MEK1$^{D218,D222}$ allele (MEKDD) (Brunet et al. (1994) Oncogene 9, 3379-3387) (gifts from H. Widlund, Dana-Farber Cancer Insitute) into pBabe-Puro or pBabe-HcRed (Boehm et al. (2005) Mol. Cell. Biol. 25, 6464-6474). pMKO-GFP-PTEN has been described (Boehm et al. (2005) Mol. Cell. Biol. 25, 6464-6474). pBabe-GFP-Myr-Flag-PI3K 110α allele and pBabe-GFP-Myr-Flag-AKT1 were created by introducing the Myr-Flag-PI3K 110α (Zhao et al., (2003) Cancer Cell 3, 483-495) or the Myr-Flag-AKT1 allele (Ramaswamy et al. (1999) Proc. Natl. Acad. Sci. USA 96, 2110-2115) into pBabe-GFP. pBabe-Puro-RAS$^{V12}$ has been described (Serrano et al. (1997) Cell 88, 593-602). pBabe-Puro-Myr-FLAG-IKBKE, pBabe-Puro-Flag-IKBKE, pBabe-Neo-Myr-Flag-IKBKE and pBabe-Neo-Flag-IKBKE were generated by PCR cloning Myr-Flag-IKBKE or Flag-IKBKE from pWN-DEST-MF-IKBKE into pBabe-Puro or pBabe-Neo, and were fully sequenced. For experiments subsequent to the primary screen, MEKDD, Myr-Flag-IKBKE, Flag-IKBKE, and Myr-Flag-AKT were introduced into HA1E cells using pBabe-HcRed-MEKDD (FIG. 5) or pBabe-Puro-MEKDD (FIG. 2D), pBabe-Puro-Myr-Flag-IKBKE, pBabe-Puro-Flag-IKBKE and pBabe-GFP-Myr-Flag-AKT1 and HMECs using pBabe-Puro-MEKDD, pBabe-Neo-Myr-Flag-IKBKE and pBabe-Neo-Flag-IKBKE. To introduce MUT IκBα or wt IκBα, pBabe-GFP-MUT IκBα (FIG. 5C), pBabe-Puro-MUT IκBα (FIG. 5J and FIG. 5K), or pBabe-GFP-wt IκBα (FIG. 5C) was used, which were created by cloning MUT IκBα or wt IκBα (gift from K. Steigmeier, Dana-Farber Cancer Institute) into pBabe-GFP or pBabe-Puro.

D. Retroviral Infection

Infections were performed serially by using drug selection or fluorescence-activated cell sorting to purify cell populations 48 hours after injection. For puromycin selection, 2 μg/mL (HEK cells) or 0.5 μg/mL (HMEL cells) was used. For neomycin selection, 150 ng/mL (HMEL cells) was used.

E. Anchorage-Independent Growth and Tumorigenicity Assays

Growth of cells in soft agar was determined by plating 5×10$^4$ cells in triplicate in 0.4% (HEK) or 0.3% (HMEC) Noble agar. Colonies greater than 100 μm in diameter were counted microscopically 8 weeks after plating. Colonies greater than 200 nm in diameter were counted macroscopically 8 weeks after plating. Tumor xenograft experiments were performed as described (Boehm et al., (2005) Mol. Cell. Biol. 25, 6464-6474). Tumor injection sites were monitored for 80 days for tumor formation.

F. Immunoblotting

Immunoblotting was performed as described (Boehm et al., (2005) Mol. Cell. Biol. 25, 6464-6474). The following antibodies were used: anti-IKKϵ C-14 (Santa Cruz Biotech, Inc., Santa Cruz, Calif.) or anti-IKKϵ c-terminal (Sigma-Aldrich, St. Louis, Mo.), anti-IκBα C-15 (Santa Cruz Biotech, Inc., Santa Cruz, Calif.), anti-NKκB H-119 (Santa Cruz Biotech, Inc., Santa Cruz, Calif.), anti-MEK1/2 (Cell Signaling Technology, Inc., Danvers, Mass.), anti-Cyclin D1 (Neomarkers, Lab Vision Corp., Fremont, Calif.), or anti-IRF3 (Santa Cruz Biotech, Inc., Santa Cruz, Calif.).

G. Immunofluorescence

For immunofluorescence, cells were seeded on Teflon-coated slides and incubated for 24 hours. Cells were washed with PBS, fixed in 4% paraformaldehyde, and permeabilized with 0.5% Triton. After washing, slides were blocked with Dakocytomation Protein Block (Dakocytomation), incubated for 2 hours with anti-NKκB H-119, and then incubated with a FITC-conjugated anti-Rabbit IgG (Molecular Probes, Invitrogen Corp., Carlsbad, Calif.). After washing, slides were counterstained with Hoechst 33342 (10 uM) (Invitrogen Corp., Carlsbad, Calif.).

H. PCR

A list of gene-specific primers used is as follows:

FIG. 3D:

```
IKBKE
                                           (SEQ ID NO: 4)
(forward;       5'-TGCGTGCAGAAGTATCAAGC-3', (SEQ ID NO: 5)
reverse;        5'-TACAGGCAGCCACAGAACAG-3')
```

FIG. 5C:

```
NFKBIA
                                           (SEQ ID NO: 6)
(forward;       5'-GCCTGGACTCCATGAAAGAC-3', (SEQ ID NO: 7)
reverse;        5'-GACACGTGTGGCCATTGTAG-3')
```

FIGS. 5G,H, FIGS. 6A,B,C:

```
CCND1
                                           (SEQ ID NO: 8)
(forward;       5'-AACTACCTGGACCGCTTCCT-3', (SEQ ID NO: 9)
reverse;        5'-CCACTTGAGCTTGTTCACCA-3')

MYC
                                           (SEQ ID NO: 10)
(forward;       5'-TTCGGGTAGTGGAAAACCAG-3', (SEQ ID NO: 11)
reverse;        5'-CAGCAGCTCGAATTTCTTCC-3')

PTGS2
                                           (SEQ ID NO: 12)
(forward;       5'-TGAGCATCTACGGTTTGCTG-3', (SEQ ID NO: 13)
reverse;        5'-TGCTTGTCTGGAACAACTGC-3')

IL1A
                                           (SEQ ID NO: 14)
(forward;       5'-AATGACGCCCTCAATCAAAG-3', (SEQ ID NO: 15)
reverse;        5'-TGGGTATCTCAGGCATCTCC-3')

MMP9
                                           (SEQ ID NO: 16)
(forward;       5'-TTGACAGCGACAAGAAGTGG-3', (SEQ ID NO: 17)
reverse;        5'-GCCATTCACGTCGTCCTTAT-3')

VEGF
                                           (SEQ ID NO: 18)
(forward;       5'-CCCACTGAGGAGTCCAACAT-3', (SEQ ID NO: 19)
reverse;        5'-TTTCTTGCGCTTTCGTTTTT-3')
```

```
BIRC2
                                                (SEQ ID NO: 20)
(forward;       5'-CCAGGTCCCTCGTATCAAAA-3', (SEQ ID NO: 21)
reverse;        5'-AAACCAGCACGAGCAAGACT-3')

BIRC3
                                                (SEQ ID NO: 22)
(forward;       5'-CTTTGCCTGTGGTGGAAAAT-3', (SEQ ID NO: 23)
reverse;        5'-ACTTGCAAGCTGCTCAGGAT-3')

BCL2
                                                (SEQ ID NO: 24)
(forward;       5'-GAGGATTGTGGCCTTCTTTG-3', (SEQ ID NO: 25)
reverse;        5'-ACAGTTCCACAAAGGCATCC-3')
```

FIGS. 9B,C:

```
IFNB1
                                                (SEQ ID NO: 26)
(forward;       5'-ACTGCCTCAAGGACAGGATG-3', (SEQ ID NO: 27)
reverse;        5'-AGCCAGGAGGTTCTCAACAA-3')

CCL5
                                                (SEQ ID NO: 28)
(forward;       5'-CCATATTCCTCGGACACCAC-3', (SEQ ID NO: 29)
reverse;        5'-TGTACTCCCGAACCCATTTC-3')
```

For quantitative RT-PCR, SYBR-Green (Applied Biosystems) was used. For RT-PCR, total RNA was isolated using TRIzol (Invitrogen Corp., Carlsbad, Calif.). For quantitative RT-PCR, we used SYBR-Green (Applied Biosystems, Foster City, Calif.).

I. Immunohistochemistry

Breast cancer Tissue Microarray slides (Biomax BR803) were immunostained with anti-IKKε-c-terminal (1:250; Sigma) and anti-c-Rel c-terminus (1:200; Chemicon) antibodies using microwave-citrate antigen retrieval followed by standard IHC staining procedures. Arrays were scored in a blinded manner by a pathologist on a scale of 0-3.

J. Genome Structure Analyses

SNP array, aCGH and SAGE data was collected and analyzed as described (Garraway et al. (2005) *Nature* 436, 117-122).

K. Fluorescence In Situ Hybridization (Fish)

Bacterial artificial chromosome (BAC) clone CTD 2229G19 containing IKBKE (Invitrogen Corp., Carlsbad, Calif.) was labeled with digoxigenin (Roche Diagnostics Corp., Indianapolis, Ind.) using the enzyme mix from the BioNick labeling kit (Invitrogen Corp., Carlsbad, Calif.) as described (Zhao et al. (1995) *Mol. Cell. Biol.* 15, 4353-4363). The probe was detected according to the manufacturer's recommendations (Cytocell Technologies Ltd., Cambridge, United Kingdom). The Spectrum Orange labeled chromosome 1 specific centromeric probe (D1Z5) and whole chromosome paint probe (WCP1) were obtained from Vysis, Inc. (Downers Grove, Ill.). Tissue and cell line preparations were performed as described (Yao et al., (2006) *Cancer Res.* 66, 4065-4078) and hybridization of metaphase chromosomes was performed as described (Ney et al. (1993) *Mol; Cell. Biol.* 13, 5604-5612).

L. RNA Interference

To stably suppress IKBKE and other members of the IKK family, pLKO. 1 lentiviral shRNA constructs generated by TRC (Moffat et al. (2006) *Cell* 124, 1283-1298) were used. Lentiviral infections were performed as described (Moffat et al. (2006) *Cell* 124, 1283-1298). Cell Titer Glo (Promega Corp., Madison, Wis.) was used to measure viability 5 days after lentiviral infection. Z-scores were calculated by normalizing the viability score of each well to the plate mean viability score and standard deviation (SD) of plate viability scores: $Z=(X-\mu)/\sigma$, where X=assay value (relative luminescence); $\mu$=mean plate viability score; and $\sigma$=SD of plate viability scores. Suppression of viability was defined as the capacity for at least one shRNA to decrease viability more than 1.5 SD below the mean Z-score and at least one additional shRNA targeting the same kinase to decrease viability more than 1 SD below the mean Z-score.

M. shRNA Experiments

To suppress IRF3 in FIG. 9D, shRNA specific for the following IRF3 sequences using pLKO.1 lentiviral vectors (Moffat et al. (2006) *Cell* 124, 1283-1298) were introduced:

```
                                                (SEQ ID NO: 30)
shIRF3 #1:      CCCTTCATTGTAGATCTGATT (SEQ ID NO: 31)
shIRF3 #2:      GCCAACCTGGAAGAGGAATTT
```

Figure 4:
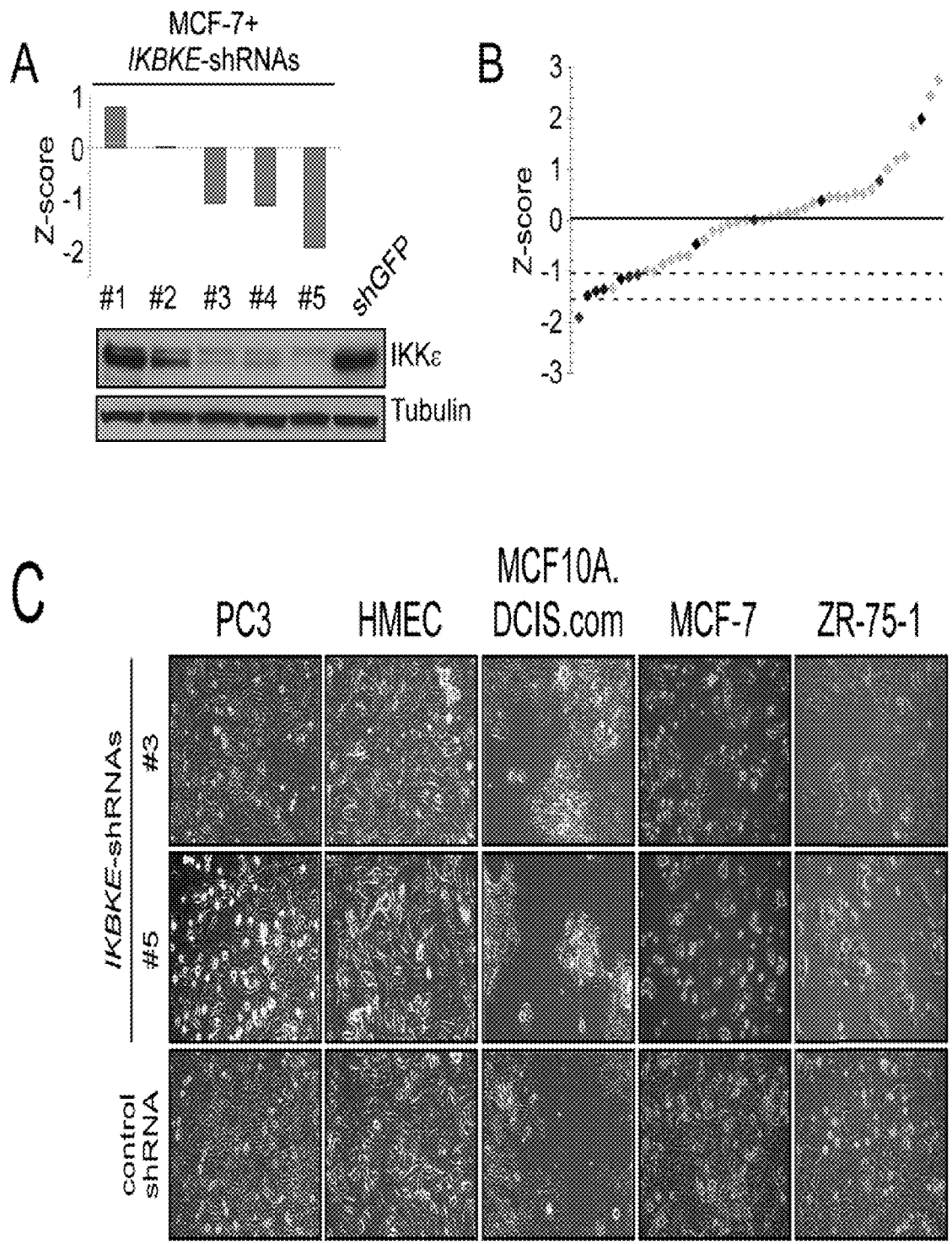
FIGS. 4A-D show that IKBKE is an essential kinase in breast cancer cells.
Figure 4:
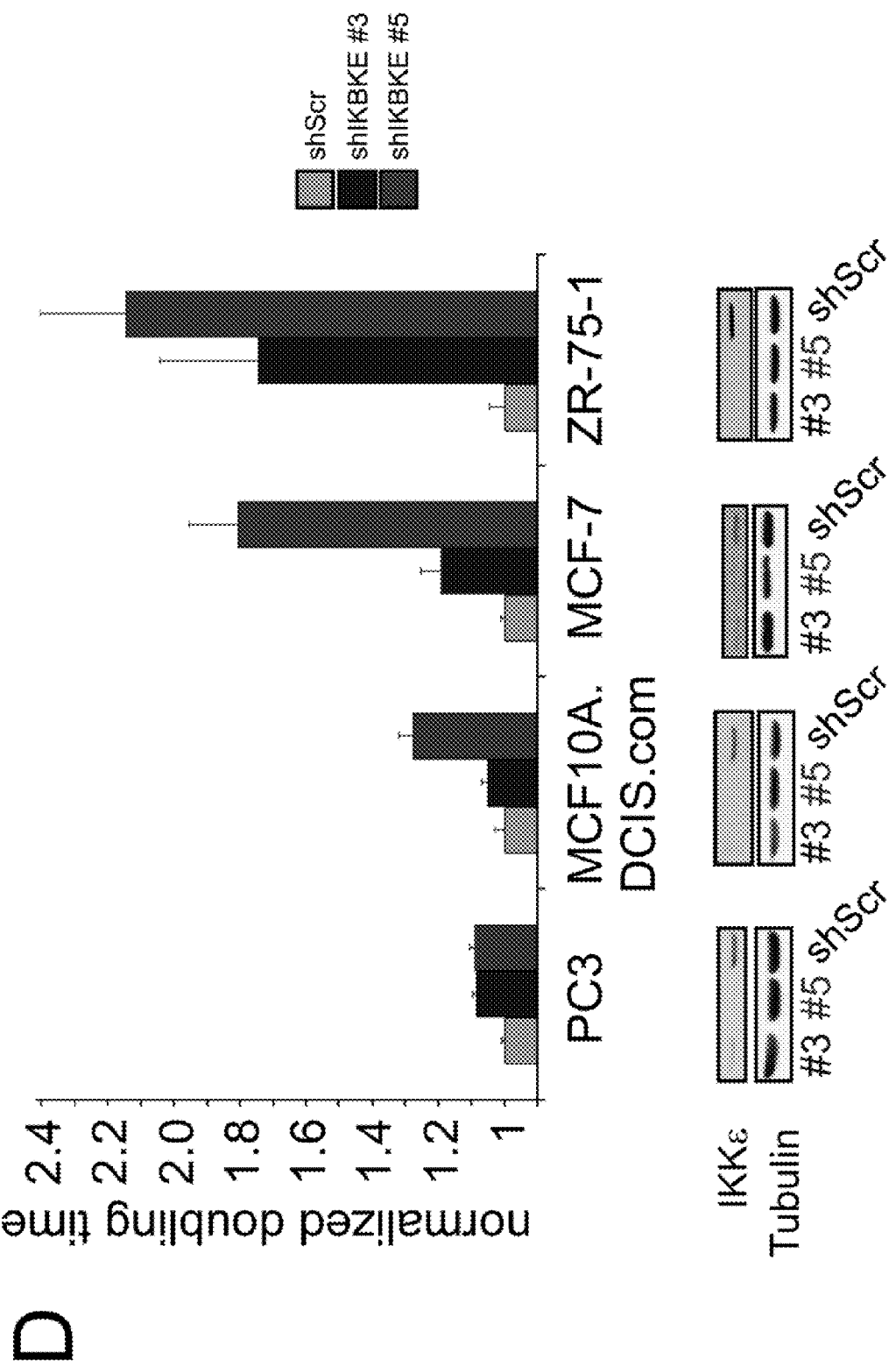
Figure 5:
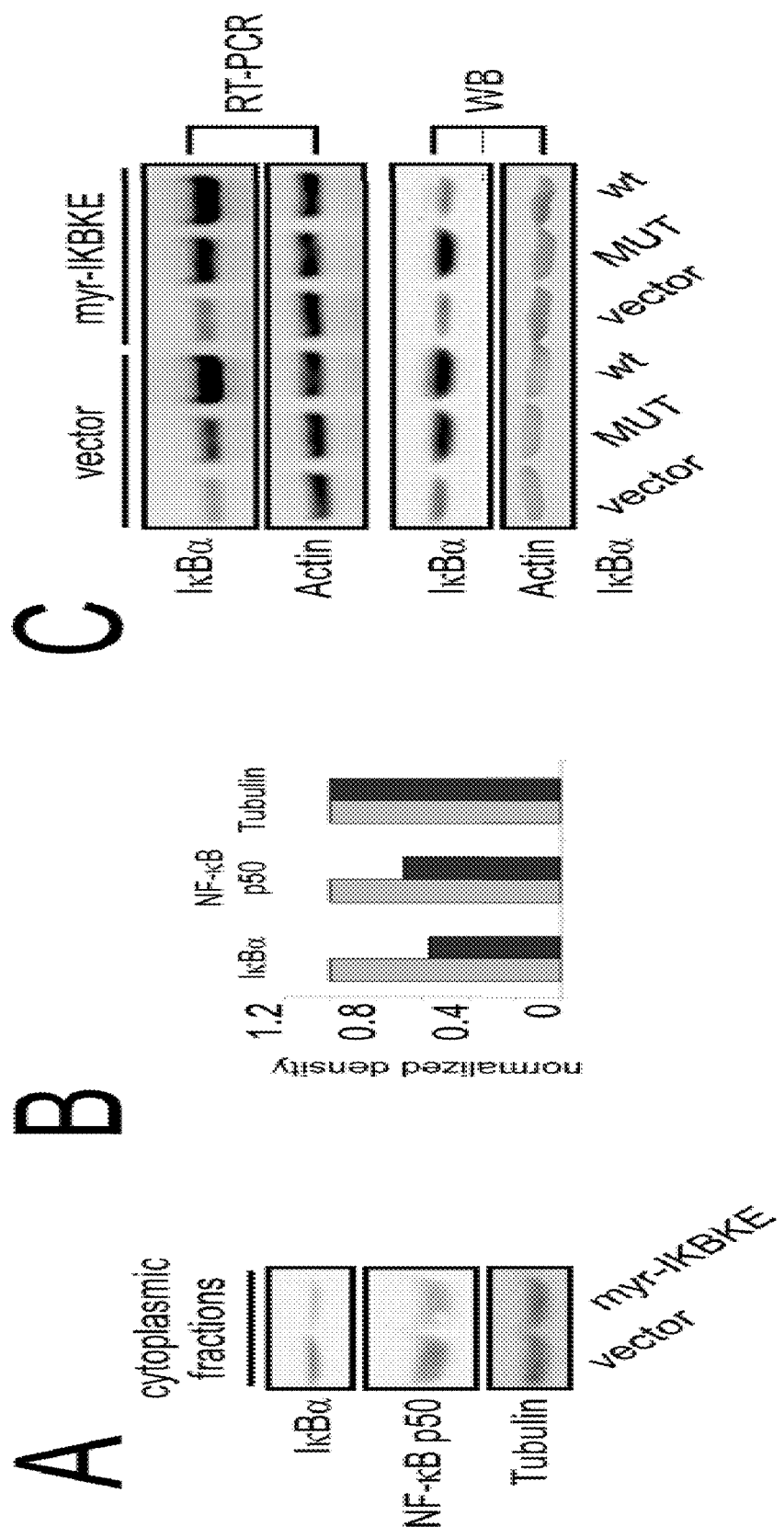
Figure 5:
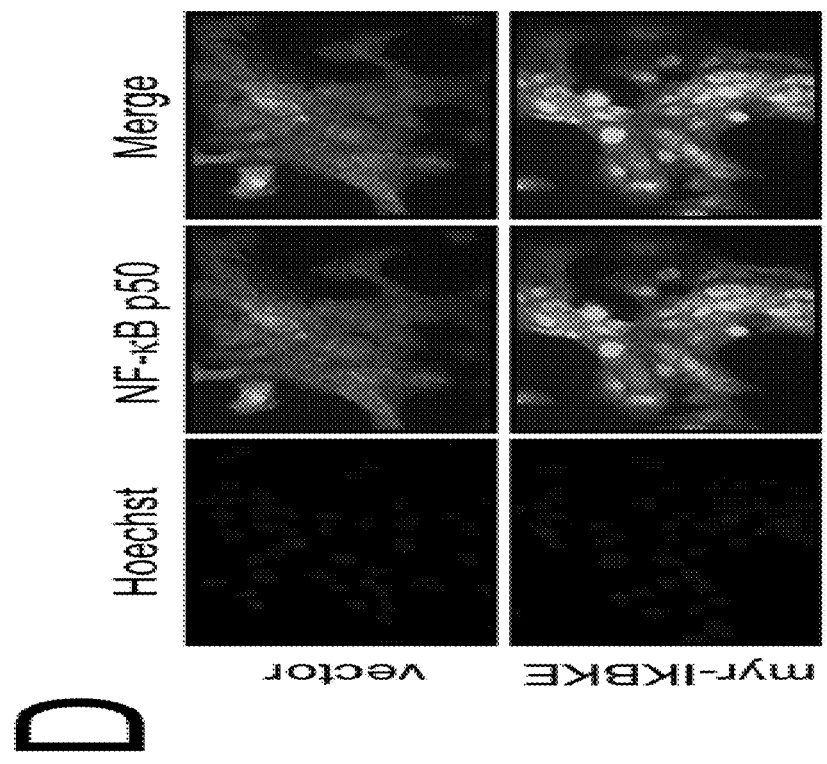
Figure 5:
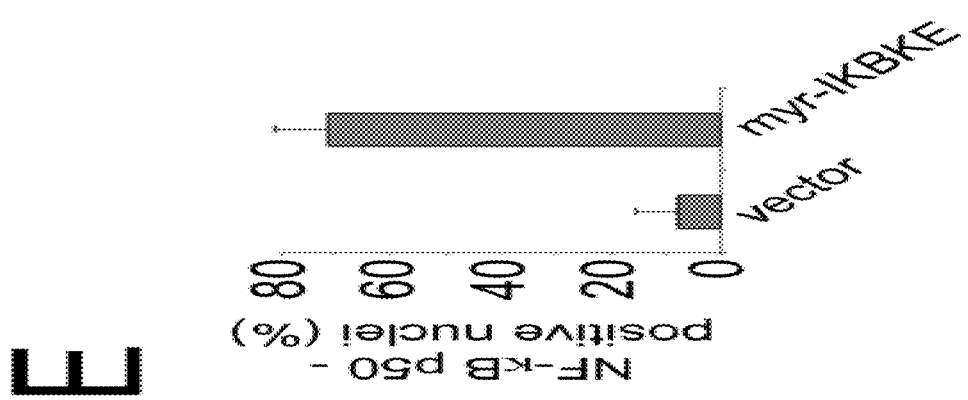
Figure 5:
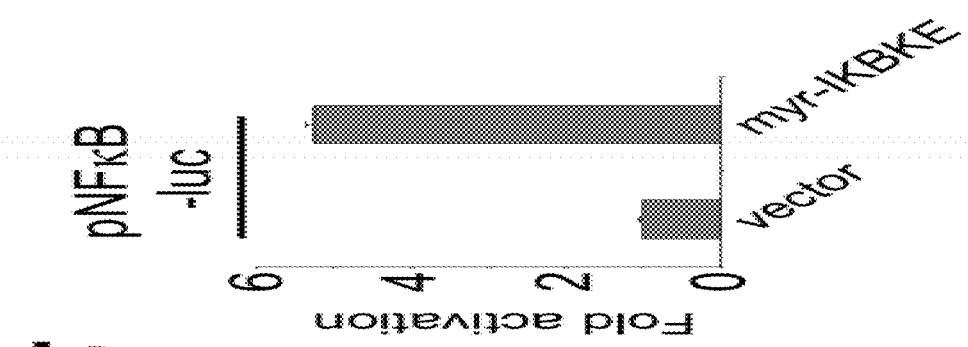
Figure 5:
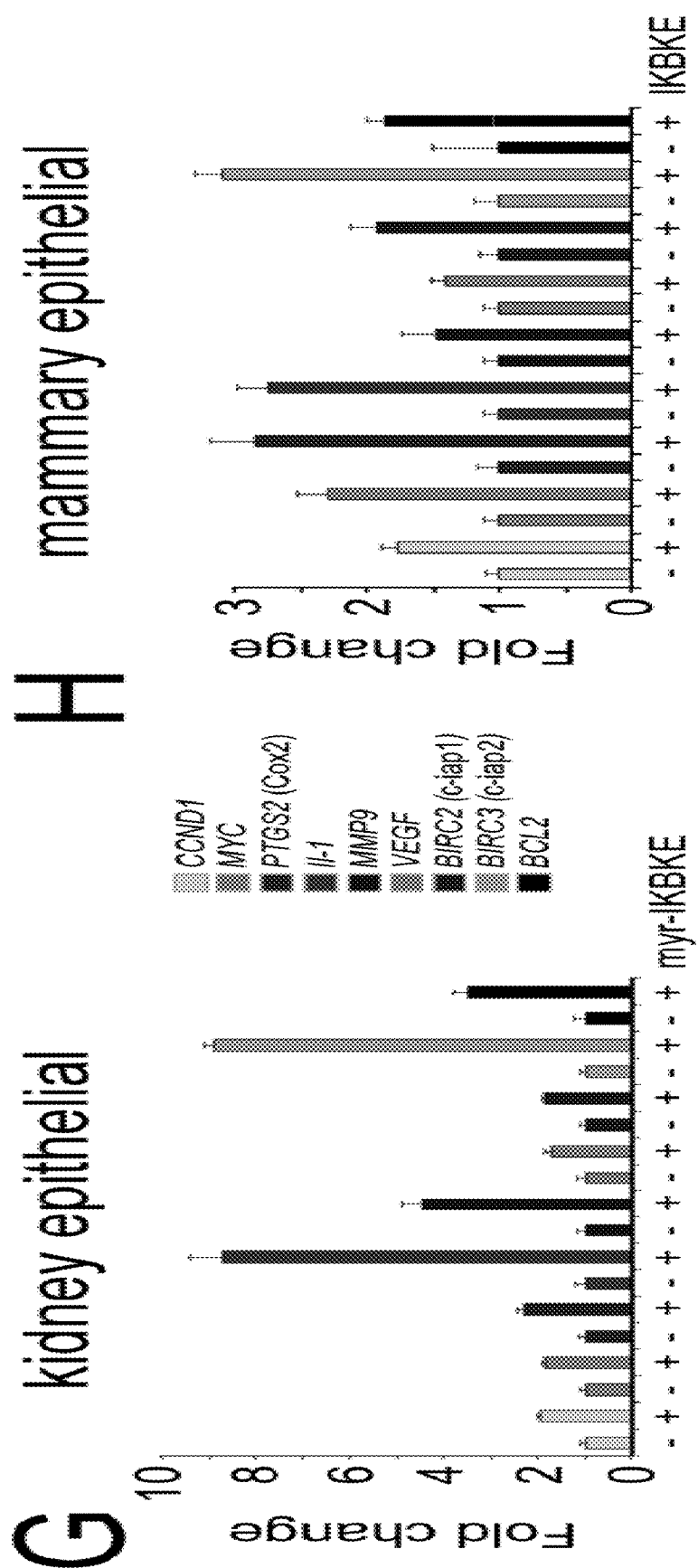
Figure 5:
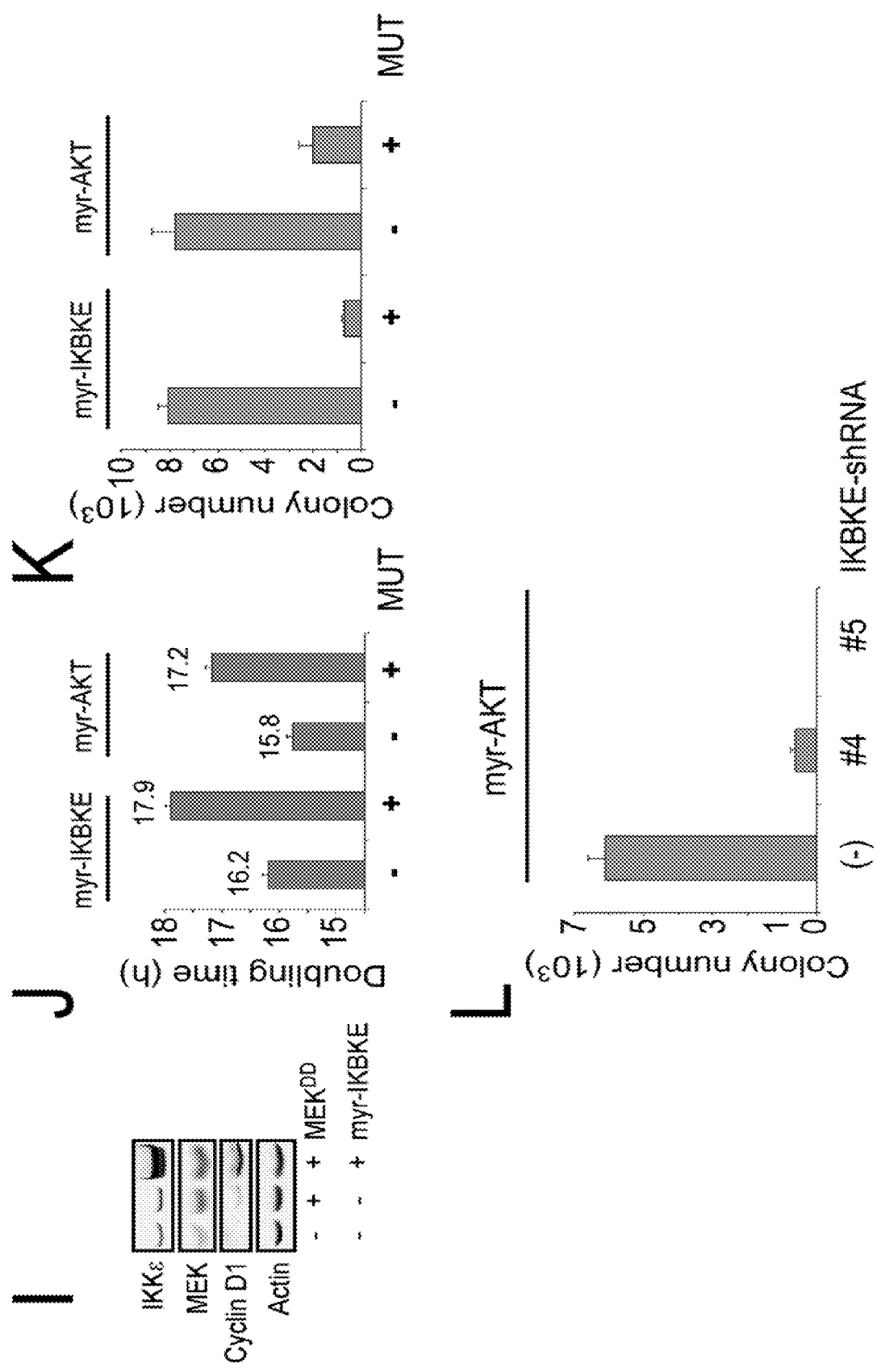
Figure 6:
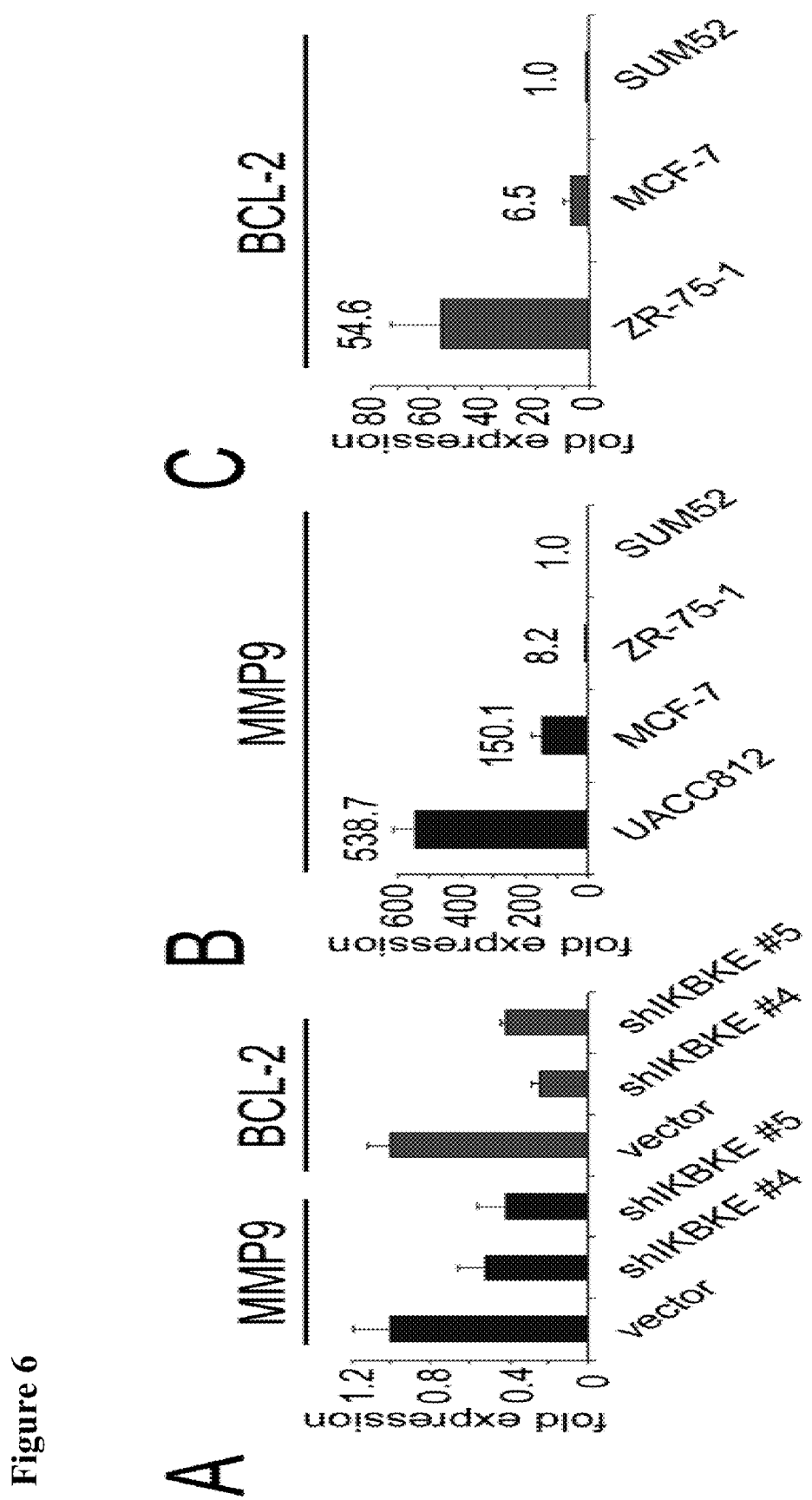
FIGS. 6A-E show that IKBKE activates the NF-κB pathway in breast cancer.
Figure 6:
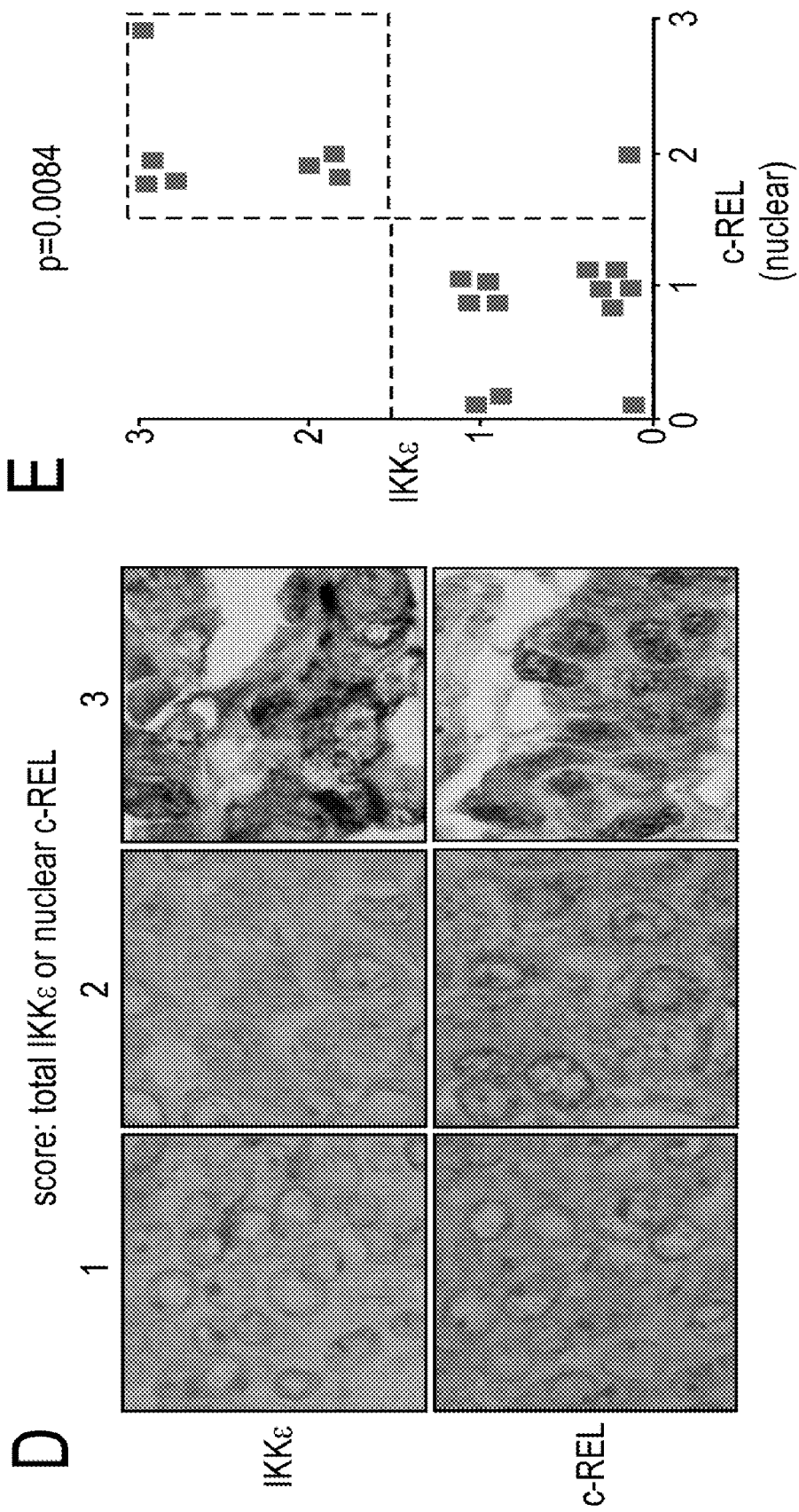

To suppress IKBKE in FIGS. 4-6, shRNA specific for the following IKBKE sequences using pLKO.1 lentiviral vectors were introduced (Moffat et al. (2006) *Cell* 124, 1283-1298):

```
                                                (SEQ ID NO: 32)
shIKBKE #3:     TGGGCAGGAGCTAATGTTTCG (SEQ ID NO: 33)
shIKBKE #4:     GTCCTTAGTCACACACGGCAA (SEQ ID NO: 34)
shIKBKE #5:     GAGCATTGGAGTGACCTTGTA
```

N. Reporter Assays

For NF-κB or interferon reporter assays, $3 \times 10^4$ cells were seeded in triplicate in 24-well plates. 12 hours after seeding, 100 ng of pNF-κB-luciferase (BD Biosciences) or pISRE-luciferase (Stratagene) plus 500 ng *renilla*-encoding plasmid (pRL-TK, gift from L. Poling, Dana-Farber Cancer Institute) was transfected in triplicate using Fugene (Roche), Media was replaced after 6 hours, and luciferase and *renilla* signals were measured 24 hours after transfection using the Dual Luciferase Reporter Assay Kit (Promega).

Example 7

Identification of Kinases and Signaling Pathways Involved in Resistance to PI3K Inactivation Another contemplated embodiment of the invention involves the use of kinase libraries described herein to identify kinases and signaling pathways that establish resistance to PI3K inactivation. In one example, the screens using the kinase libraries employ cells that harbor a specific knockout of PIK3CA, which is the PB Kinase catalytic subunit which uses ATP to phosphorylate phosphatydinositol molecules. As PI3K inhibitors are entering clinical trials, drug resistance is likely to be the next frontier. Information arising from screens as described herein will provide a better understanding of the mechanisms by which tumor cells might survive and even grow in the presence of a PI3K inhibitor and for identifying kinases or pathways, which might optimally be targeted in concert with PI3K inhibition. Preliminary screening using the myr-kinase library described in Example 6 have resulted in the identification of a number of kinases, e.g. Akt, Raf, MATK and MAP3K8, that could drive oncogenic transformation of these cells even when PIK3CA is inactivated, providing a potential resistance mechanism for PI3K inhibitors in cancer treatment. For example, PIK3CA is frequently mutated in many types of human cancer and these mutations are oncogenic. PI3K inhibitors are being developed to target cancers carrying PIK3CA mutations. However, if these cancer cells also harbor activated Akt, Raf, MATK or MAP3K8, they may not respond to PI3K inhibitors and combination therapy may be proposed.

Example 8

Figure 10:
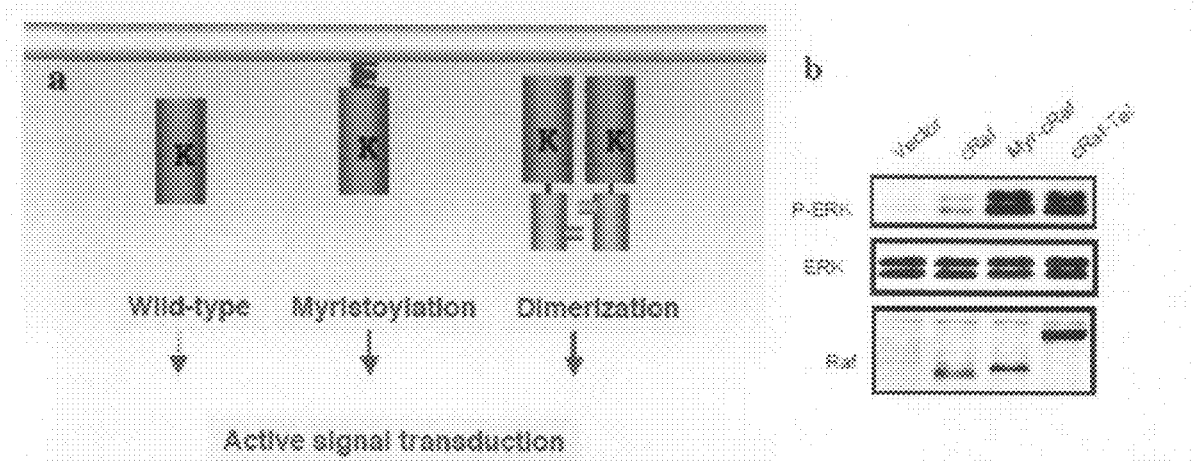
FIGS. 10A-10B show a depiction of kinase activation by either myristoylation or dimerization.
Figure 11:
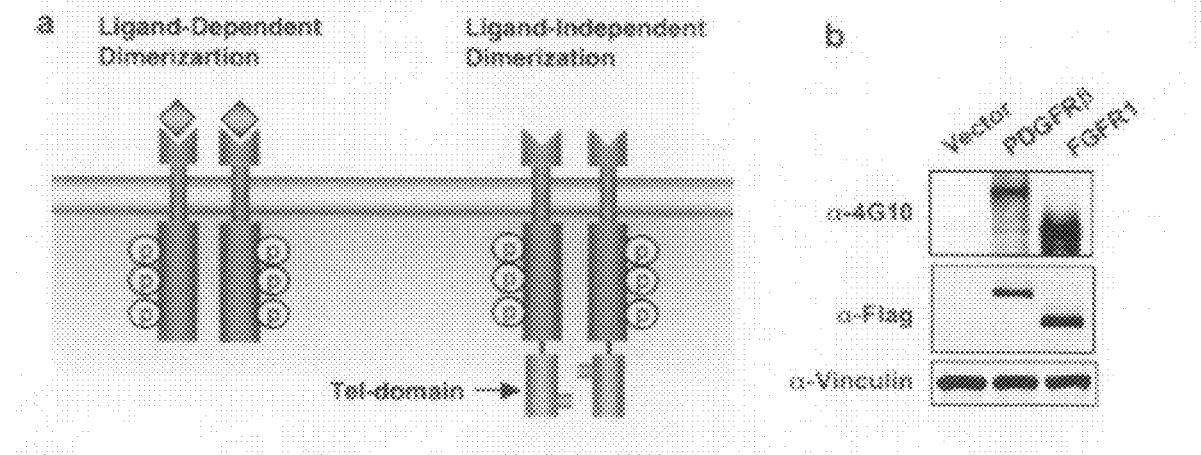
FIGS. 11A-11B show a depiction of kinase activation mediated by fusions with TEL-domains.

Identification of Kinases and Signaling Pathways Involved in Resistance to PI3K Inactivation To complement the library of kinases activated by myristoylation, the helix-loop-helix domain (HL) of the Tel transcription factor (Tel-HLH) was used to activate tyrosine kinases (TKs). The human genome contains roughly 90 tyrosine kinases (TKs). Since most TKs are not efficiently activated by myristoylation, but can usually be activated by dimerization, a ligand-independent dimerization system was employed to make chimeric proteins that contain TKs fused at their C-termini to the Tel-HLH domain (FIG. 10). Tel-HLH was isolated as an element fused to PDGR in patients with chronic myelomonocytic leukemia. The HLH domain of the transcription factor Tel mediates the dimerization of the Tel/PDGFR fusion protein and leads to the constitutive activation of PDGFR, resulting in cellular transformation (Carroll et al, (1996) Proc. Natl. Acad. Sci. U.S.A. 93:14845-14850). Similar to the construction of myristoylated kinase library as described in Example 6, a retroviral-based, Gateway-compatible DEST-vector containing elements encoding HLH domain of Tel fused in frame with a Flag-epitope, pWN-TelF-DEST was constructed. Full-length ORFs of TKs lacking stop codons were moved into the Gateway entry vector and subsequently into pWN-TelF-DEST. TKs expressed from pWN-TelF-DEST vector feature a full-length protein kinase fused in frame with the Tel-HLH domain and a Flag epitope. To test for expression and activation of the resulting fusion proteins, these Tel-TK clones were introduced into 293T cells, which were then starved for growth factors and lysed. The resulting lysates were then analyzed by western blotting. The blots were developed with Flag antibodies to check for protein expression and with the 4G10 antibody to assess for tyrosine phosphorylation of these Tel-TKs (FIG. 11).

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

TABLE 1

| NCBI Gene ID | Official Symbol | Description |
| --- | --- | --- |
| 25 | ABL1 | v-abl Abelson murine leukemia viral oncogene homolog 1 |
| 27 | ABL2 | v-abl Abelson murine leukemia viral oncogene homolog 2 (arg, Abelson-related gene) |
| 90 | ACVR1 | activin A receptor, type I |
| 91 | ACVR1B | activin A receptor, type IB |
| 92 | ACVR2 | activin A receptor, type II |
| 93 | ACVR2B | activin A receptor, type IIB |
| 94 | ACVRL1 | activin A receptor typeII-like 1 |
| 132 | ADK | adenosine kinase |
| 156 | ADRBK1 | adrenergic, beta, receptor kinase 1 |
| 157 | ADRBK2 | adrenergic, beta, receptor kinase 2 |
| 203 | AK1 | adenylate kinase 1 |
| 204 | AK2 | adenylate kinase 2 |
| 205 | AK3 | adenylate kinase 3 |
| 207 | AKT1 | v-akt murine thymoma viral oncogene homolog 1 |
| 208 | AKT2 | v-akt murine thymoma viral oncogene homolog 2 |
| 238 | ALK | anaplastic lymphoma kinase (Ki-1) |
| 269 | AMHR2 | anti-Mullerian hormone receptor, type II |
| 369 | ARAF1 | v-raf murine sarcoma 3611 viral oncogene homolog 1 |
| 472 | ATM | ataxia telangiectasia mutated (includes complementation groups A, C and D) |
| 545 | ATR | ataxia telangiectasia and Rad3 related |
| 558 | AXL | AXL receptor tyrosine kinase |
| 613 | BCR | breakpoint cluster region |
| 640 | BLK | B lymphoid tyrosine kinase |
| 657 | BMPR1A | bone morphogenetic protein receptor, type IA |
| 658 | BMPR1B | bone morphogenetic protein receptor, type IB |
| 659 | BMPR2 | bone morphogenetic protein receptor, type II (serine/threonine kinase) |
| 660 | BMX | BMX non-receptor tyrosine kinase |
| 673 | BRAF | v-raf murine sarcoma viral oncogene homolog B1 |
| 676 | BRDT | bromodomain, testis-specific |
| 695 | BTK | Bruton agammaglobulinemia tyrosine kinase |
| 699 | BUB1 | BUB1 budding uninhibited by benzimidazoles 1 homolog (yeast) |
| 701 | BUB1B | BUB1 budding uninhibited by benzimidazoles 1 homolog beta (yeast) |
| 780 | DDR1 | discoidin domain receptor family, member 1 |
| 801 | CALM1 | calmodulin 1 (phosphorylase kinase, delta) |
| 805 | CALM2 | calmodulin 2 (phosphorylase kinase, delta) |
| 808 | CALM3 | calmodulin 3 (phosphorylase kinase, delta) |
| 814 | CAMK4 | calcium/calmodulin-dependent protein kinase IV |

TABLE 1-continued

| NCBI Gene ID | Official Symbol | Description |
|---|---|---|
| 815 | CAMK2A | calcium/calmodulin-dependent protein kinase (CaM kinase) II alpha |
| 816 | CAMK2B | calcium/calmodulin-dependent protein kinase (CaM kinase) II beta |
| 817 | CAMK2D | calcium/calmodulin-dependent protein kinase (CaM kinase) II delta |
| 818 | CAMK2G | calcium/calmodulin-dependent protein kinase (CaM kinase) II gamma |
| 914 | CD2 | CD2 antigen (p50), sheep red blood cell receptor; CD2 |
| 983 | CDC2 | cell division cycle 2, G1 to S and G2 to M |
| 984 | CDC2L1 | cell division cycle 2-like 1 (PITSLRE proteins) |
| 985 | CDC2L2 | cell division cycle 2-like 2 (PITSLRE proteins) |
| 1017 | CDK2 | cyclin-dependent kinase 2 |
| 1018 | CDK3 | cyclin-dependent kinase 3 |
| 1019 | CDK4 | cyclin-dependent kinase 4 |
| 1020 | CDK5 | cyclin-dependent kinase 5 |
| 1021 | CDK6 | cyclin-dependent kinase 6 |
| 1022 | CDK7 | cyclin-dependent kinase 7 (MO15 homolog, *Xenopus laevis*, cdk-activating kinase) |
| 1024 | CDK8 | cyclin-dependent kinase 8 |
| 1025 | CDK9 | cyclin-dependent kinase 9 (CDC2-related kinase) |
| 1111 | CHEK1 | CHK1 checkpoint homolog (*S. pombe*) |
| 1119 | CHKA | choline kinase alpha |
| 1120 | CHKB | choline kinase beta |
| 1147 | CHUK | conserved helix-loop-helix ubiquitous kinase |
| 1152 | CKB | creatine kinase, brain |
| 1158 | CKM | creatine kinase, muscle |
| 1159 | CKMT1 | creatine kinase, mitochondrial 1 (ubiquitous) |
| 1160 | CKMT2 | creatine kinase, mitochondrial 2 (sarcomeric) |
| 1163 | CKS1B | CDC28 protein kinase regulatory subunit 1B |
| 1164 | CKS2 | CDC28 protein kinase regulatory subunit 2 |
| 1195 | CLK1 | CDC-like kinase 1 |
| 1196 | CLK2 | CDC-like kinase 2 |
| 1198 | CLK3 | CDC-like kinase 3 |
| 1263 | PLK3 | polo-like kinase 3 (*Drosophila*) |
| 1326 | MAP3K8 | mitogen-activated protein kinase kinase kinase 8 |
| 1399 | CRKL | v-crk sarcoma virus CT10 oncogene homolog (avian)-like; CRKL |
| 1432 | MAPK14 | mitogen-activated protein kinase 14 |
| 1436 | CSF1R | colony stimulating factor 1 receptor, formerly McDonough feline sarcoma viral (v-fms) oncogene homolog |
| 1445 | CSK | c-src tyrosine kinase |
| 1452 | CSNK1A1 | casein kinase 1, alpha 1 |
| 1453 | CSNK1D | casein kinase 1, delta |
| 1454 | CSNK1E | casein kinase 1, epsilon |
| 1455 | CSNK1G2 | casein kinase 1, gamma 2 |
| 1456 | CSNK1G3 | casein kinase 1, gamma 3 |
| 1457 | CSNK2A1 | casein kinase 2, alpha 1 polypeptide |
| 1459 | CSNK2A2 | casein kinase 2, alpha prime polypeptide |
| 1460 | CSNK2B | casein kinase 2, beta polypeptide |
| 1606 | DGKA | diacylglycerol kinase, alpha 80 kDa |
| 1607 | DGKB | diacylglycerol kinase, beta 90 kDa |
| 1608 | DGKG | diacylglycerol kinase, gamma 90 kDa |
| 1609 | DGKQ | diacylglycerol kinase, theta 110 kDa |
| 1612 | DAPK1 | death-associated protein kinase 1 |
| 1613 | DAPK3 | death-associated protein kinase 3 |
| 1633 | DCK | deoxycytidine kinase |
| 1716 | DGUOK | deoxyguanosine kinase |
| 1739 | DLG1 | discs, large homolog 1 (*Drosophila*); DLG1 |
| 1740 | DLG2 | discs, large homolog 2, chapsyn-110 (*Drosophila*); DLG2 |
| 1741 | DLG3 | discs, large homolog 3 (neuroendocrine-dlg, *Drosophila*); DLG3 |
| 1760 | DMPK | dystrophia myotonica-protein kinase |
| 1841 | DTYMK | deoxythymidylate kinase (thymidylate kinase) |
| 1859 | DYRK1A | dual-specificity tyrosine-(Y)-phosphorylation regulated kinase 1A |
| 1956 | EGFR | epidermal growth factor receptor (erythroblastic leukemia viral (v-erb-b) oncogene homolog, avian) |
| 1969 | EPHA2 | EPH receptor A2 |
| 2011 | MARK2 | MAP/microtubule affinity-regulating kinase 2 |
| 2041 | EPHA1 | EPH receptor A1 |
| 2042 | EPHA3 | EPH receptor A3 |
| 2043 | EPHA4 | EPH receptor A4 |
| 2044 | EPHA5 | EPH receptor A5 |
| 2045 | EPHA7 | EPH receptor A7 |
| 2046 | EPHA8 | EPH receptor A8 |
| 2047 | EPHB1 | EPH receptor B1 |
| 2048 | EPHB2 | EPH receptor B2 |
| 2049 | EPHB3 | EPH receptor B3 |
| 2050 | EPHB4 | EPH receptor B4 |
| 2051 | EPHB6 | EPH receptor B6 |
| 2064 | ERBB2 | v-erb-b2 erythroblastic leukemia viral oncogene homolog 2, neuro/glioblastoma derived oncogene homolog (avian) |
| 2065 | ERBB3 | v-erb-b2 erythroblastic leukemia viral oncogene homolog 3 (avian) |
| 2066 | ERBB4 | v-erb-a erythroblastic leukemia viral oncogene homolog 4 (avian) |

TABLE 1-continued

| NCBI Gene ID | Official Symbol | Description |
|---|---|---|
| 2081 | ERN1 | endoplasmic reticulum to nucleus signalling 1 |
| 2185 | PTK2B | PTK2B protein tyrosine kinase 2 beta |
| 2241 | FER | fer (fps/fes related) tyrosine kinase (phosphoprotein NCP94) |
| 2242 | FES | feline sarcoma oncogene |
| 2260 | FGFR1 | fibroblast growth factor receptor 1 (fms-related tyrosine kinase 2, Pfeiffer syndrome) |
| 2261 | FGFR3 | fibroblast growth factor receptor 3 (achondroplasia, thanatophoric dwarfism) |
| 2263 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 2264 | FGFR4 | fibroblast growth factor receptor 4 |
| 2268 | FGR | Gardner-Rasheed feline sarcoma viral (v-fgr) oncogene homolog |
| 2321 | FLT1 | fms-related tyrosine kinase 1 (vascular endothelial growth factor/vascular permeability factor receptor) |
| 2322 | FLT3 | fms-related tyrosine kinase 3 |
| 2324 | FLT4 | fms-related tyrosine kinase 4 |
| 2395 | FXN | frataxin; FXN |
| 2444 | FRK | fyn-related kinase |
| 2475 | FRAP1 | FK506 binding protein 12-rapamycin associated protein 1 |
| 2534 | FYN | FYN oncogene related to SRC, FGR, YES |
| 2580 | GAK | cyclin G associated kinase |
| 2584 | GALK1 | galactokinase 1 |
| 2585 | GALK2 | galactokinase 2 |
| 2645 | GCK | glucokinase (hexokinase 4, maturity onset diabetes of the young 2) |
| 2710 | GK | glycerol kinase |
| 2712 | GK2 | glycerol kinase 2 |
| 2868 | GRK4 | G protein-coupled receptor kinase 4 |
| 2869 | GRK5 | G protein-coupled receptor kinase 5 |
| 2870 | GRK6 | G protein-coupled receptor kinase 6 |
| 2872 | MKNK2 | MAP kinase interacting serine/threonine kinase 2 |
| 2931 | GSK3A | glycogen synthase kinase 3 alpha |
| 2932 | GSK3B | glycogen synthase kinase 3 beta |
| 2965 | GTF2H1 | general transcription factor IIH, polypeptide 1, 62 kDa; GTF2H1 |
| 2984 | GUCY2C | guanylate cyclase 2C (heat stable enterotoxin receptor) |
| 2986 | GUCY2F | guanylate cyclase 2F, retinal |
| 2987 | GUK1 | guanylate kinase 1 |
| 3000 | GUCY2D | guanylate cyclase 2D, membrane (retina-specific) |
| 3055 | HCK | hemopoietic cell kinase |
| 3098 | HK1 | hexokinase 1 |
| 3099 | HK2 | hexokinase 2 |
| 3101 | HK3 | hexokinase 3 (white cell) |
| 3480 | IGF1R | insulin-like growth factor 1 receptor |
| 3551 | IKBKB | inhibitor of kappa light polypeptide gene enhancer in B-cells, kinase beta |
| 3611 | ILK | integrin-linked kinase |
| 3643 | INSR | insulin receptor |
| 3645 | INSRR | insulin receptor-related receptor |
| 3654 | IRAK1 | interleukin-1 receptor-associated kinase 1 |
| 3656 | IRAK2 | interleukin-1 receptor-associated kinase 2 |
| 3702 | ITK | IL2-inducible T-cell kinase |
| 3705 | ITPK1 | inositol 1,3,4-triphosphate 5/6 kinase |
| 3706 | ITPKA | inositol 1,4,5-trisphosphate 3-kinase A |
| 3707 | ITPKB | inositol 1,4,5-trisphosphate 3-kinase B |
| 3716 | JAK1 | Janus kinase 1 (a protein tyrosine kinase) |
| 3717 | JAK2 | Janus kinase 2 (a protein tyrosine kinase) |
| 3718 | JAK3 | Janus kinase 3 (a protein tyrosine kinase, leukocyte) |
| 3791 | KDR | kinase insert domain receptor (a type III receptor tyrosine kinase) |
| 3795 | KHK | ketohexokinase (fructokinase) |
| 3815 | KIT | v-kit Hardy-Zuckerman 4 feline sarcoma viral oncogene homolog |
| 3932 | LCK | lymphocyte-specific protein tyrosine kinase |
| 3984 | LIMK1 | LIM domain kinase 1 |
| 3985 | LIMK2 | LIM domain kinase 2 |
| 4058 | LTK | leukocyte tyrosine kinase |
| 4067 | LYN | v-yes-1 Yamaguchi sarcoma viral related oncogene homolog |
| 4117 | MAK | male germ cell-associated kinase |
| 4139 | MARK1 | MAP/microtubule affinity-regulating kinase 1 |
| 4140 | MARK3 | MAP/microtubule affinity-regulating kinase 3 |
| 4145 | MATK | megakaryocyte-associated tyrosine kinase |
| 4214 | MAP3K1 | mitogen-activated protein kinase kinase kinase 1 |
| 4215 | MAP3K3 | mitogen-activated protein kinase kinase kinase 3 |
| 4216 | MAP3K4 | mitogen-activated protein kinase kinase kinase 4 |
| 4217 | MAP3K5 | mitogen-activated protein kinase kinase kinase 5 |
| 4233 | MET | met proto-oncogene (hepatocyte growth factor receptor) |
| 4293 | MAP3K9 | mitogen-activated protein kinase kinase kinase 9 |
| 4294 | MAP3K10 | mitogen-activated protein kinase kinase kinase 10 |
| 4296 | MAP3K11 | mitogen-activated protein kinase kinase kinase 11 |
| 4342 | MOS | v-mos Moloney murine sarcoma viral oncogene homolog |
| 4354 | MPP1 | membrane protein, palmitoylated 1, 55 kDa; MPP1 |
| 4355 | MPP2 | membrane protein, palmitoylated 2 (MAGUK p55 subfamily member 2); MPP2 |

TABLE 1-continued

| NCBI Gene ID | Official Symbol | Description |
|---|---|---|
| 4356 | MPP3 | membrane protein, palmitoylated 3 (MAGUK p55 subfamily member 3); MPP3 |
| 4486 | MST1R | macrophage stimulating 1 receptor (c-met-related tyrosine kinase) |
| 4593 | MUSK | muscle, skeletal, receptor tyrosine kinase |
| 4598 | MVK | mevalonate kinase (mevalonic aciduria) |
| 4638 | MYLK | myosin, light polypeptide kinase |
| 4750 | NEK1 | NIMA (never in mitosis gene a)-related kinase 1 |
| 4751 | NEK2 | NIMA (never in mitosis gene a)-related kinase 2 |
| 4752 | NEK3 | NIMA (never in mitosis gene a)-related kinase 3 |
| 4830 | NME1 | nucleoside-diphosphate kinase 1 |
| 4831 | NME2 | nucleoside-diphosphate kinase 2 |
| 4832 | NME3 | nucleoside-diphosphate kinase 3 |
| 4833 | NME4 | nucleoside-diphosphate kinase 4 |
| 4881 | NPR1 | natriuretic peptide receptor A/guanylate cyclase A (atrionatriuretic peptide receptor A) |
| 4882 | NPR2 | natriuretic peptide receptor B/guanylate cyclase B (atrionatriuretic peptide receptor B) |
| 4914 | NTRK1 | neurotrophic tyrosine kinase, receptor, type 1 |
| 4915 | NTRK2 | neurotrophic tyrosine kinase, receptor, type 2 |
| 4916 | NTRK3 | neurotrophic tyrosine kinase, receptor, type 3 |
| 4919 | ROR1 | receptor tyrosine kinase-like orphan receptor 1 |
| 4920 | ROR2 | receptor tyrosine kinase-like orphan receptor 2 |
| 4921 | DDR2 | discoidin domain receptor family, member 2 |
| 5058 | PAK1 | p21/Cdc42/Rac1-activated kinase 1 (STE20 homolog, yeast) |
| 5062 | PAK2 | p21 (CDKN1A)-activated kinase 2 |
| 5063 | PAK3 | p21 (CDKN1A)-activated kinase 3 |
| 5105 | PCK1 | phosphoenolpyruvate carboxykinase 1 (soluble) |
| 5106 | PCK2 | phosphoenolpyruvate carboxykinase 2 (mitochondrial) |
| 5127 | PCTK1 | PCTAIRE protein kinase 1 |
| 5128 | PCTK2 | PCTAIRE protein kinase 2 |
| 5129 | PCTK3 | PCTAIRE protein kinase 3 |
| 5156 | PDGFRA | platelet-derived growth factor receptor, alpha polypeptide |
| 5157 | PDGFRL | platelet-derived growth factor receptor-like; PDGFRL |
| 5159 | PDGFRB | platelet-derived growth factor receptor, beta polypeptide |
| 5163 | PDK1 | pyruvate dehydrogenase kinase, isoenzyme 1 |
| 5164 | PDK2 | pyruvate dehydrogenase kinase, isoenzyme 2 |
| 5165 | PDK3 | pyruvate dehydrogenase kinase, isoenzyme 3 |
| 5166 | PDK4 | pyruvate dehydrogenase kinase, isoenzyme 4 |
| 5170 | PDPK1 | 3-phosphoinositide dependent protein kinase-1 |
| 5207 | PFKFB1 | 6-phosphofructo-2-kinase/fructose-2,6-biphosphatase 1 |
| 5208 | PFKFB2 | 6-phosphofructo-2-kinase/fructose-2,6-biphosphatase 2 |
| 5209 | PFKFB3 | 6-phosphofructo-2-kinase/fructose-2,6-biphosphatase 3 |
| 5210 | PFKFB4 | 6-phosphofructo-2-kinase/fructose-2,6-biphosphatase 4 |
| 5211 | PFKL | phosphofructokinase, liver |
| 5213 | PFKM | phosphofructokinase, muscle |
| 5214 | PFKP | phosphofructokinase, platelet |
| 5218 | PFTK1 | PFTAIRE protein kinase 1 |
| 5230 | PGK1 | phosphoglycerate kinase 1 |
| 5232 | PGK2 | phosphoglycerate kinase 2 |
| 5255 | PHKA1 | phosphorylase kinase, alpha 1 (muscle) |
| 5256 | PHKA2 | phosphorylase kinase, alpha 2 (liver) |
| 5257 | PHKB | phosphorylase kinase, beta |
| 5260 | PHKG1 | phosphorylase kinase, gamma 1 (muscle) |
| 5261 | PHKG2 | phosphorylase kinase, gamma 2 (testis) |
| 5286 | PIK3C2A | phosphoinositide-3-kinase, class 2, alpha polypeptide |
| 5287 | PIK3C2B | phosphoinositide-3-kinase, class 2, beta polypeptide |
| 5288 | PIK3C2G | phosphoinositide-3-kinase, class 2, gamma polypeptide |
| 5289 | PIK3C3 | phosphoinositide-3-kinase, class 3 |
| 5290 | PIK3CA | phosphoinositide-3-kinase, catalytic, alpha polypeptide |
| 5291 | PIK3CB | phosphoinositide-3-kinase, catalytic, beta polypeptide |
| 5292 | PIM1 | pim-1 oncogene |
| 5293 | PIK3CD | phosphoinositide-3-kinase, catalytic, delta polypeptide |
| 5294 | PIK3CG | phosphoinositide-3-kinase, catalytic, gamma polypeptide |
| 5295 | PIK3R1 | phosphoinositide-3-kinase, regulatory subunit 1 (p85 alpha) |
| 5296 | PIK3R2 | phosphoinositide-3-kinase, regulatory subunit 2 (p85 beta) |
| 5297 | PIK4CA | phosphatidylinositol 4-kinase, catalytic, alpha polypeptide |
| 5298 | PIK4CB | phosphatidylinositol 4-kinase, catalytic, beta polypeptide |
| 5305 | PIP5K2A | phosphatidylinositol-4-phosphate 5-kinase, type II, alpha |
| 5313 | PKLR | pyruvate kinase, liver and RBC |
| 5315 | PKM2 | pyruvate kinase, muscle |
| 5328 | PLAU | plasminogen activator, urokinase |
| 5347 | PLK1 | polo-like kinase 1 (*Drosophila*) |
| 5361 | PLXNA1 | plexin A1; PLXNA1 |
| 5362 | PLXNA2 | plexin A2; PLXNA2 |
| 5364 | PLXNB1 | plexin B1; PLXNB1 |
| 5365 | PLXNB3 | plexin B3; PLXNB3 |
| 5394 | EXOSC10 | exosome component 10; EXOSC10 |
| 5562 | PRKAA1 | protein kinase, AMP-activated, alpha 1 catalytic subunit |
| 5563 | PRKAA2 | protein kinase, AMP-activated, alpha 2 catalytic subunit |
| 5564 | PRKAB1 | protein kinase, AMP-activated, beta 1 non-catalytic subunit |

TABLE 1-continued

| NCBI Gene ID | Official Symbol | Description |
|---|---|---|
| 5565 | PRKAB2 | protein kinase, AMP-activated, beta 2 non-catalytic subunit |
| 5566 | PRKACA | protein kinase, cAMP-dependent, catalytic, alpha |
| 5567 | PRKACB | protein kinase, cAMP-dependent, catalytic, beta |
| 5568 | PRKACG | protein kinase, cAMP-dependent, catalytic, gamma |
| 5571 | PRKAG1 | protein kinase, AMP-activated, gamma 1 non-catalytic subunit |
| 5573 | PRKAR1A | protein kinase, cAMP-dependent, regulatory, type I, alpha (tissue specific extinguisher 1) |
| 5575 | PRKAR1B | protein kinase, cAMP-dependent, regulatory, type I, beta |
| 5576 | PRKAR2A | protein kinase, cAMP-dependent, regulatory, type II, alpha |
| 5577 | PRKAR2B | protein kinase, cAMP-dependent, regulatory, type II, beta |
| 5578 | PRKCA | protein kinase C, alpha |
| 5579 | PRKCB1 | protein kinase C, beta 1 |
| 5580 | PRKCD | protein kinase C, delta |
| 5581 | PRKCE | protein kinase C, epsilon |
| 5582 | PRKCG | protein kinase C, gamma |
| 5583 | PRKCH | protein kinase C, eta |
| 5584 | PRKCI | protein kinase C, iota |
| 5585 | PKN1 | protein kinase N1 |
| 5586 | PKN2 | protein kinase N2 |
| 5587 | PRKD1 | protein kinase D1 |
| 5588 | PRKCQ | protein kinase C, theta |
| 5590 | PRKCZ | protein kinase C, zeta |
| 5591 | PRKDC | protein kinase, DNA-activated, catalytic polypeptide |
| 5592 | PRKG1 | protein kinase, cGMP-dependent, type I |
| 5593 | PRKG2 | protein kinase, cGMP-dependent, type II |
| 5594 | MAPK1 | mitogen-activated protein kinase 1 |
| 5595 | MAPK3 | mitogen-activated protein kinase 3 |
| 5596 | MAPK4 | mitogen-activated protein kinase 4 |
| 5597 | MAPK6 | mitogen-activated protein kinase 6 |
| 5598 | MAPK7 | mitogen-activated protein kinase 7 |
| 5599 | MAPK8 | mitogen-activated protein kinase 8 |
| 5600 | MAPK11 | mitogen-activated protein kinase 11 |
| 5601 | MAPK9 | mitogen-activated protein kinase 9 |
| 5602 | MAPK10 | mitogen-activated protein kinase 10 |
| 5603 | MAPK13 | mitogen-activated protein kinase 13 |
| 5604 | MAP2K1 | mitogen-activated protein kinase kinase 1 |
| 5605 | MAP2K2 | mitogen-activated protein kinase kinase 2 |
| 5606 | MAP2K3 | mitogen-activated protein kinase kinase 3 |
| 5607 | MAP2K5 | mitogen-activated protein kinase kinase 5 |
| 5608 | MAP2K6 | mitogen-activated protein kinase kinase 6 |
| 5609 | MAP2K7 | mitogen-activated protein kinase kinase 7 |
| 5610 | PRKR | protein kinase, interferon-inducible double stranded RNA dependent |
| 5613 | PRKX | protein kinase, X-linked |
| 5616 | PRKY | protein kinase, Y-linked |
| 5631 | PRPS1 | phosphoribosyl pyrophosphate synthetase 1; PRPS1 |
| 5634 | PRPS2 | phosphoribosyl pyrophosphate synthetase 2; PRPS2 |
| 5681 | PSKH1 | protein serine kinase H1 |
| 5747 | PTK2 | PTK2 protein tyrosine kinase 2 |
| 5753 | PTK6 | PTK6 protein tyrosine kinase 6 |
| 5754 | PTK7 | PTK7 protein tyrosine kinase 7 |
| 5756 | PTK9 | PTK9 protein tyrosine kinase 9 |
| 5832 | ALDH18A1 | aldehyde dehydrogenase 18 family, member A1; ALDH18A1 |
| 5871 | MAP4K2 | mitogen-activated protein kinase kinase kinase kinase 2 |
| 5891 | RAGE | renal tumor antigen |
| 5894 | RAF1 | v-raf-1 murine leukemia viral oncogene homolog 1 |
| 5979 | RET | ret proto-oncogene (multiple endocrine neoplasia and medullary thyroid carcinoma 1, Hirschsprung disease) |
| 5987 | TRIM27 | tripartite motif-containing 27; TRIM27 |
| 6011 | GRK1 | G protein-coupled receptor kinase 1 |
| 6041 | RNASEL | ribonuclease L (2',5'-oligoisoadenylate synthetase-dependent) |
| 6046 | BRD2 | bromodomain containing 2 |
| 6093 | ROCK1 | Rho-associated, coiled-coil containing protein kinase 1 |
| 6098 | ROS1 | v-ros UR2 sarcoma virus oncogene homolog 1 (avian) |
| 6102 | RP2 | retinitis pigmentosa 2 (X-linked recessive); RP2 |
| 6195 | RPS6KA1 | ribosomal protein S6 kinase, 90 kDa, polypeptide 1 |
| 6196 | RPS6KA2 | ribosomal protein S6 kinase, 90 kDa, polypeptide 2 |
| 6197 | RPS6KA3 | ribosomal protein S6 kinase, 90 kDa, polypeptide 3 |
| 6198 | RPS6KB1 | ribosomal protein S6 kinase, 70 kDa, polypeptide 1 |
| 6199 | RPS6KB2 | ribosomal protein S6 kinase, 70 kDa, polypeptide 2 |
| 6259 | RYK | RYK receptor-like tyrosine kinase |
| 6300 | MAPK12 | mitogen-activated protein kinase 12 |
| 6347 | CCL2 | chemokine (C-C motif) ligand 2; CCL2 |
| 6351 | CCL4 | chemokine (C-C motif) ligand 4; CCL4 |
| 6416 | MAP2K4 | mitogen-activated protein kinase kinase 4 |
| 6446 | SGK | serum/glucocorticoid regulated kinase |
| 6714 | SRC | v-src sarcoma (Schmidt-Ruppin A-2) viral oncogene homolog (avian) |
| 6725 | SRMS | src-related kinase lacking C-terminal regulatory tyrosine and N-terminal myristylation sites |

TABLE 1-continued

| NCBI Gene ID | Official Symbol | Description |
| --- | --- | --- |
| 6732 | SRPK1 | SFRS protein kinase 1 |
| 6733 | SRPK2 | SFRS protein kinase 2 |
| 6787 | NEK4 | NIMA (never in mitosis gene a)-related kinase 4 |
| 6788 | STK3 | serine/threonine kinase 3 (STE20 homolog, yeast) |
| 6789 | STK4 | serine/threonine kinase 4 |
| 6790 | STK6 | serine/threonine kinase 6 |
| 6792 | CDKL5 | cyclin-dependent kinase-like 5 |
| 6793 | STK10 | serine/threonine kinase 10 |
| 6794 | STK11 | serine/threonine kinase 11 (Peutz-Jeghers syndrome) |
| 6795 | AURKC | aurora kinase C |
| 6850 | SYK | spleen tyrosine kinase |
| 6872 | TAF1 | TAF1 RNA polymerase II, TATA box binding protein (TBP)-associated factor, 250 kDa |
| 6885 | MAP3K7 | mitogen-activated protein kinase kinase kinase 7 |
| 7006 | TEC | tec protein tyrosine kinase |
| 7010 | TEK | TEK tyrosine kinase, endothelial (venous malformations, multiple cutaneous and mucosal) |
| 7016 | TESK1 | testis-specific kinase 1 |
| 7046 | TGFBR1 | transforming growth factor, beta receptor I (activin A receptor type II-like kinase, 53 kDa) |
| 7048 | TGFBR2 | transforming growth factor, beta receptor II (70/80 kDa) |
| 7049 | TGFBR3 | transforming growth factor, beta receptor III (betaglycan, 300 kDa); TGFBR3 |
| 7075 | TIE1 | tyrosine kinase with immunoglobulin-like and EGF-like domains 1 |
| 7083 | TK1 | thymidine kinase 1, soluble |
| 7084 | TK2 | thymidine kinase 2, mitochondrial |
| 7175 | TPR | translocated promoter region (to activated MET oncogene); TPR |
| 7204 | TRIO | triple functional domain (PTPRF interacting) |
| 7272 | TTK | TTK protein kinase |
| 7273 | TTN | titin |
| 7294 | TXK | TXK tyrosine kinase |
| 7297 | TYK2 | tyrosine kinase 2 |
| 7301 | TYRO3 | TYRO3 protein tyrosine kinase |
| 7371 | UCK2 | uridine-cytidine kinase 2 |
| 7443 | VRK1 | *vaccinia* related kinase 1 |
| 7444 | VRK2 | *vaccinia* related kinase 2 |
| 7465 | WEE1 | WEE1 homolog (*S. pombe*) |
| 7525 | YES1 | v-yes-1 Yamaguchi sarcoma viral oncogene homolog 1 |
| 7535 | ZAP70 | zeta-chain (TCR) associated protein kinase 70 kDa |
| 7786 | MAP3K12 | mitogen-activated protein kinase kinase kinase 12 |
| 7867 | MAPKAPK3 | mitogen-activated protein kinase-activated protein kinase 3 |
| 8019 | BRD3 | bromodomain containing 3 |
| 8295 | TRRAP | transformation/transcription domain-associated protein |
| 8317 | CDC7 | CDC7 cell division cycle 7 (*S. cerevisiae*) |
| 8382 | NME5 | non-metastatic cells 5, protein expressed in (nucleoside-diphosphate kinase) |
| 8394 | PIP5K1A | phosphatidylinositol-4-phosphate 5-kinase, type I, alpha |
| 8395 | PIP5K1B | phosphatidylinositol-4-phosphate 5-kinase, type I, beta |
| 8396 | PIP5K2B | phosphatidylinositol-4-phosphate 5-kinase, type II, beta |
| 8408 | ULK1 | unc-51-like kinase 1 (*C. elegans*) |
| 8428 | STK24 | serine/threonine kinase 24 (STE20 homolog, yeast) |
| 8444 | DYRK3 | dual-specificity tyrosine-(Y)-phosphorylation regulated kinase 3 |
| 8445 | DYRK2 | dual-specificity tyrosine-(Y)-phosphorylation regulated kinase 2 |
| 8476 | CDC42BPA | CDC42 binding protein kinase alpha (DMPK-like) |
| 8491 | MAP4K3 | mitogen-activated protein kinase kinase kinase kinase 3 |
| 8503 | PIK3R3 | phosphoinositide-3-kinase, regulatory subunit 3 (p55, gamma) |
| 8525 | DGKZ | diacylglycerol kinase, zeta 104 kDa |
| 8526 | DGKE | diacylglycerol kinase, epsilon 64 kDa |
| 8527 | DGKD | diacylglycerol kinase, delta 130 kDa |
| 8536 | CAMK1 | calcium/calmodulin-dependent protein kinase I |
| 8550 | MAPKAPK5 | mitogen-activated protein kinase-activated protein kinase 5 |
| 8558 | CDK10 | cyclin-dependent kinase (CDC2-like) 10 |
| 8566 | PDXK | pyridoxal (pyridoxine, vitamin B6) kinase |
| 8569 | MKNK1 | MAP kinase interacting serine/threonine kinase 1 |
| 8573 | CASK | calcium/calmodulin-dependent serine protein kinase (MAGUK family) |
| 8576 | STK16 | serine/threonine kinase 16 |
| 8621 | CDC2L5 | cell division cycle 2-like 5 (cholinesterase-related cell division controller) |
| 8649 | MAP2K1IP1 | mitogen-activated protein kinase kinase 1 interacting protein 1 |
| 8711 | TNK1 | tyrosine kinase, non-receptor, 1 |
| 8737 | RIPK1 | receptor (TNFRSF)-interacting serine-threonine kinase 1 |
| 8767 | RIPK2 | receptor-interacting serine-threonine kinase 2 |
| 8780 | RIOK3 | RIO kinase 3 (yeast) |
| 8798 | DYRK4 | dual-specificity tyrosine-(Y)-phosphorylation regulated kinase 4 |
| 8814 | CDKL1 | cyclin-dependent kinase-like 1 (CDC2-related kinase) |
| 8844 | KSR | kinase suppressor of ras |
| 8851 | CDK5R1 | cyclin-dependent kinase 5, regulatory subunit 1 (p35) |
| 8859 | STK19 | serine/threonine kinase 19 |
| 8877 | SPHK1 | sphingosine kinase 1 |
| 8895 | CPNE3 | copine III; CPNE3 |
| 8899 | PRPF4B | PRP4 pre-mRNA processing factor 4 homolog B (yeast) |
| 8941 | CDK5R2 | cyclin-dependent kinase 5, regulatory subunit 2 (p39) |

TABLE 1-continued

| NCBI Gene ID | Official Symbol | Description |
|---|---|---|
| 8986 | RPS6KA4 | ribosomal protein S6 kinase, 90 kDa, polypeptide 4 |
| 8997 | KALRN | kalirin, RhoGEF kinase isoform 1 |
| 8999 | CDKL2 | cyclin-dependent kinase-like 2 (CDC2-related kinase) |
| 9020 | MAP3K14 | mitogen-activated protein kinase kinase kinase 14 |
| 9024 | STK29 | serine/threonine kinase 29 |
| 9060 | PAPSS2 | 3'-phosphoadenosine 5'-phosphosulfate synthase 2; PAPSS2 |
| 9061 | PAPSS1 | 3'-phosphoadenosine 5'-phosphosulfate synthase 1; PAPSS1 |
| 9064 | MAP3K6 | mitogen-activated protein kinase kinase kinase 6 |
| 9088 | PKMYT1 | membrane-associated tyrosine- and threonine-specific cdc2-inhibitory kinase |
| 9113 | LATS1 | LATS, large tumor suppressor, homolog 1 (*Drosophila*) |
| 9149 | DYRK1B | dual-specificity tyrosine-(Y)-phosphorylation regulated kinase 1B |
| 9162 | DGKI | diacylglycerol kinase, iota |
| 9175 | MAP3K13 | mitogen-activated protein kinase kinase kinase 13 |
| 9201 | DCAMKL1 | doublecortin and CaM kinase-like 1 |
| 9212 | AURKB | aurora kinase B |
| 9223 | MAGI1 | membrane associated guanylate kinase, WW and PDZ domain containing 1; MAGI1 |
| 9252 | RPS6KA5 | ribosomal protein S6 kinase, 90 kDa, polypeptide 5 |
| 9261 | MAPKAPK2 | mitogen-activated protein kinase-activated protein kinase 2 |
| 9262 | STK17B | serine/threonine kinase 17b (apoptosis-inducing) |
| 9263 | STK17A | serine/threonine kinase 17a (apoptosis-inducing) |
| 9344 | TAOK2 | TAO kinase 2 |
| 9414 | ZO2 | tight junction protein 2 (zona occludens 2); TJP2 |
| 9448 | MAP4K4 | mitogen-activated protein kinase kinase kinase kinase 4 |
| 9451 | EIF2AK3 | eukaryotic translation initiation factor 2-alpha kinase 3 |
| 9467 | SH3BP5 | SH3-domain binding protein 5 (BTK-associated); SH3BP5 |
| 9475 | ROCK2 | Rho-associated, coiled-coil containing protein kinase 2 |
| 9578 | CDC42BPB | CDC42 binding protein kinase beta (DMPK-like) |
| 9625 | AATK | apoptosis-associated tyrosine kinase |
| 9641 | IKBKE | inhibitor of kappa light polypeptide gene enhancer in B-cells, kinase epsilon |
| 9706 | ULK2 | unc-51-like kinase 2 (*C. elegans*) |
| 9748 | SLK | STE20-like kinase (yeast) |
| 9807 | IHPK1 | inositol hexaphosphate kinase 1 |
| 9829 | DNAJC6 | DnaJ (Hsp40) homolog, subfamily C, member 6; DNAJC6 |
| 9833 | MELK | maternal embryonic leucine zipper kinase |
| 9863 | MAGI2 | membrane associated guanylate kinase, WW and PDZ domain containing 2; MAGI2 |
| 9874 | TLK1 | tousled-like kinase 1 |
| 9891 | ARK5 | AMP-activated protein kinase family member 5 |
| 9942 | XYLB | xylulokinase homolog (*H. influenzae*) |
| 9943 | OXSR1 | oxidative-stress responsive 1 |
| 9950 | GOLGA5 | golgi autoantigen, golgin subfamily a, 5; GOLGA5 |
| 10000 | AKT3 | v-akt murine thymoma viral oncogene homolog 3 (protein kinase B, gamma) |
| 10020 | GNE | glucosamine (UDP-N-acetyl)-2-epimerase/N-acetylmannosamine kinase |
| 10087 | COL4A3BP | collagen, type IV, alpha 3 (Goodpasture antigen) binding protein; COL4A3BP |
| 10110 | SGK2 | serum/glucocorticoid regulated kinase 2 |
| 10114 | HIPK3 | homeodomain interacting protein kinase 3 |
| 10128 | LRPPRC | leucine-rich PPR-motif containing; LRPPRC |
| 10154 | PLXNC1 | plexin C1; PLXNC1 |
| 10188 | ACK1 | activated Cdc42-associated kinase 1 |
| 10201 | NME6 | non-metastatic cells 6, protein expressed in (nucleoside-diphosphate kinase) |
| 10221 | TRIB1 | tribbles homolog 1 (*Drosophila*) |
| 10290 | APEG1 | aortic preferentially expressed protein 1 |
| 10295 | BCKDK | branched chain alpha-ketoacid dehydrogenase kinase |
| 10298 | PAK4 | p21(CDKN1A)-activated kinase 4 |
| 10420 | TESK2 | testis-specific kinase 2 |
| 10461 | MERTK | c-mer proto-oncogene tyrosine kinase |
| 10494 | STK25 | serine/threonine kinase 25 (STE20 homolog, yeast) |
| 10519 | CIB1 | calcium and integrin binding 1 (calmyrin); CIB1 |
| 10595 | ERN2 | endoplasmic reticulum to nucleus signalling 2 |
| 10645 | CAMKK2 | calcium/calmodulin-dependent protein kinase kinase 2, beta |
| 10654 | PMVK | phosphomevalonate kinase |
| 10733 | PLK4 | polo-like kinase 4 (*Drosophila*) |
| 10746 | MAP3K2 | mitogen-activated protein kinase kinase kinase 2 |
| 10769 | PLK2 | polo-like kinase 2 (*Drosophila*) |
| 10783 | NEK6 | NIMA (never in mitosis gene a)-related kinase 6 |
| 10922 | FASTK | FAST kinase |
| 11011 | TLK2 | tousled-like kinase 2 |
| 11035 | RIPK3 | receptor-interacting serine-threonine kinase 3 |
| 11040 | PIM2 | pim-2 oncogene |
| 11113 | CIT | citron (rho-interacting, serine/threonine kinase 21) |
| 11183 | MAP4K5 | mitogen-activated protein kinase kinase kinase kinase 5 |
| 11184 | MAP4K1 | mitogen-activated protein kinase kinase kinase kinase 1 |
| 11200 | CHEK2 | CHK2 checkpoint homolog (*S. pombe*) |
| 11213 | IRAK3 | interleukin-1 receptor-associated kinase 3 |
| 11284 | PNKP | polynucleotide kinase 3'-phosphatase |
| 11329 | STK38 | serine/threonine kinase 38 |
| 11344 | PTK9L | PTK9L protein tyrosine kinase 9-like (A6-related protein) |
| 22848 | AAK1 | AP2 associated kinase 1 |

TABLE 1-continued

| NCBI Gene ID | Official Symbol | Description |
|---|---|---|
| 22853 | LMTK2 | lemur tyrosine kinase 2 |
| 22858 | ICK | intestinal cell (MAK-like) kinase |
| 22868 | FASTKD2 | FAST kinase domains 2; FASTKD2 |
| 22901 | ARSG | arylsulfatase G; ARSG |
| 22928 | SPS2 | selenophosphate synthetase 2; SEPHS2 |
| 22983 | MAST1 | microtubule associated serine/threonine kinase 1 |
| 23012 | STK38L | serine/threonine kinase 38 like |
| 23031 | MAST3 | microtubule associated serine/threonine kinase 3 |
| 23043 | TNIK | TRAF2 and NCK interacting kinase |
| 23049 | SMG1 | PI-3-kinase-related kinase SMG-1 |
| 23097 | CDC2L6 | cell division cycle 2-like 6 (CDK8-like) |
| 23129 | PLXND1 | plexin D1; PLXND1 |
| 23139 | MAST2 | microtubule associated serine/threonine kinase 2 |
| 23178 | PASK | PAS domain containing serine/threonine kinase |
| 23227 | MAST4 | microtubule associated serine/threonine kinase family member 4 |
| 23235 | SIK2 | salt-inducible serine/threonine kinase 2 |
| 23300 | ASCIZ | ATM/ATR-Substrate Chk2-Interacting Zn2+-finger protein; ASCIZ |
| 23387 | KIAA0999 | KIAA0999 protein |
| 23396 | PIP5K1C | phosphatidylinositol-4-phosphate 5-kinase, type I, gamma |
| 23476 | BRD4 | bromodomain containing 4 |
| 23533 | PIK3R5 | phosphoinositide-3-kinase, regulatory subunit 5, p101 |
| 23552 | CCRK | cell cycle related kinase |
| 23604 | DAPK2 | death-associated protein kinase 2 |
| 23617 | STK22B | serine/threonine kinase 22B (spermiogenesis associated) |
| 23636 | NUP62 | nucleoporin 62 kDa; NUP62 |
| 23654 | PLXNB2 | plexin B2; PLXNB2 |
| 23677 | SH3BP4 | SH3-domain binding protein 4; SH3BP4 |
| 23678 | SGKL | serum/glucocorticoid regulated kinase-like |
| 23683 | PRKD3 | protein kinase D3 |
| 23729 | CARKL | carbohydrate kinase-like |
| 25778 | RIPK5 | receptor interacting protein kinase 5 |
| 25865 | PRKD2 | protein kinase D2 |
| 25989 | DKFZP434C131 | DKFZP434C131 protein |
| 26007 | DAK | dihydroxyacetone kinase 2 homolog (*S. cerevisiae*); DAK |
| 26289 | AK5 | adenylate kinase 5 |
| 26353 | HSPB8 | heat shock 22 kDa protein 8 |
| 26524 | LATS2 | LATS, large tumor suppressor, homolog 2 (*Drosophila*) |
| 26576 | STK23 | serine/threonine kinase 23 |
| 26750 | RPS6KC1 | ribosomal protein S6 kinase, 52 kDa, polypeptide 1 |
| 27010 | TPK1 | thiamin pyrophosphokinase 1 |
| 27102 | HRI | heme-regulated initiation factor 2-alpha kinase |
| 27148 | STK36 | serine/threonine kinase 36 (fused homolog, *Drosophila*) |
| 27231 | ITGB1BP3 | integrin beta 1 binding protein 3; ITGB1BP3 |
| 27330 | RPS6KA6 | ribosomal protein S6 kinase, 90 kDa, polypeptide 6 |
| 27347 | STK39 | serine threonine kinase 39 (STE20/SPS1 homolog, yeast) |
| 28951 | TRIB2 | tribbles homolog 2 (*Drosophila*) |
| 28996 | HIPK2 | homeodomain interacting protein kinase 2 |
| 29110 | TBK1 | TANK-binding kinase 1 |
| 29904 | EEF2K | eukaryotic elongation factor-2 kinase |
| 29922 | NME7 | non-metastatic cells 7, protein expressed in (nucleoside-diphosphate kinase) |
| 29941 | PKN3 | protein kinase N3 |
| 29959 | NRBP | nuclear receptor binding protein |
| 30811 | HUNK | hormonally upregulated Neu-associated kinase |
| 30849 | PIK3R4 | phosphoinositide-3-kinase, regulatory subunit 4, p150 |
| 50488 | MINK | misshapen/NIK-related kinase |
| 50808 | AK3L1 | adenylate kinase 3 like 1 |
| 51086 | TNNI3K | TNNI3 interacting kinase |
| 51135 | IRAK4 | interleukin-1 receptor-associated kinase 4 |
| 51231 | VRK3 | *vaccinia*related kinase 3 |
| 51265 | CDKL3 | cyclin-dependent kinase-like 3 |
| 51314 | TXNDC3 | thioredoxin domain containing 3 (spermatozoa); TXNDC3 |
| 51347 | TAOK3 | TAO kinase 3 |
| 51422 | PRKAG2 | protein kinase, AMP-activated, gamma 2 non-catalytic subunit |
| 51447 | IHPK2 | inositol hexaphosphate kinase 2 |
| 51678 | MPP6 | membrane protein, palmitoylated 6 (MAGUK p55 subfamily member 6); MPP6 |
| 51701 | NLK | nemo like kinase |
| 51727 | UMP-CMPK | UMP-CMP kinase |
| 51755 | CRK7 | CDC2-related protein kinase 7 |
| 51765 | MST4 | Mst3 and SOK1-related kinase |
| 51776 | ZAK | sterile alpha motif and leucine zipper containing kinase AZK |
| 53354 | PANK1 | pantothenate kinase 1 |
| 53632 | PRKAG3 | protein kinase, AMP-activated, gamma 3 non-catalytic subunit |
| 53834 | FGFRL1 | fibroblast growth factor receptor-like 1; FGFRL1 |
| 53904 | MYO3A | myosin IIIA |
| 53944 | CSNK1G1 | casein kinase 1, gamma 1 |
| 54101 | RIPK4 | receptor-interacting serine-threonine kinase 4 |
| 54103 | LOC54103 | hypothetical protein LOC54103; LOC54103 |

TABLE 1-continued

| NCBI Gene ID | Official Symbol | Description |
|---|---|---|
| 54822 | TRPM7 | transient receptor potential cation channel, subfamily M, member 7 |
| 54861 | SNRK | SNF-1 related kinase |
| 54899 | PXK | PX domain containing serine/threonine kinase |
| 54963 | UCKL1 | uridine-cytidine kinase 1-like 1 |
| 54981 | C9orf95 | chromosome 9 open reading frame 95; C9orf95 |
| 54986 | FLJ20574 | hypothetical protein FLJ20574 |
| 55224 | ETNK2 | ethanolamine kinase 2 |
| 55229 | PANK4 | pantothenate kinase 4 |
| 55277 | FLJ10986 | hypothetical protein FLJ10986; FLJ10986 |
| 55300 | PI4K2B | phosphatidylinositol 4-kinase type-II beta |
| 55312 | RFK | riboflavin kinase |
| 55351 | STK32B | serine/threonine kinase 32B |
| 55359 | STYK1 | protein kinase STYK1 |
| 55361 | PI4KII | phosphatidylinositol 4-kinase type II |
| 55437 | ALS2CR2 | amyotrophic lateral sclerosis 2 (juvenile) chromosome region, candidate 2 |
| 55500 | ETNK1 | ethanolamine kinase 1 |
| 55558 | PLXNA3 | plexin A3; PLXNA3 |
| 55561 | CDC42BPG | CDC42 binding protein kinase gamma (DMPK-like) |
| 55577 | NAGK | N-acetylglucosamine kinase |
| 55589 | BMP2K | BMP2 inducible kinase |
| 55681 | FLJ10074 | hypothetical protein FLJ10074 |
| 55728 | N4BP2 | Nedd4 binding protein 2 |
| 55750 | MULK | multiple substrate lipid kinase; MULK |
| 55781 | RIOK2 | RIO kinase 2 (yeast) |
| 55872 | TOPK | T-LAK cell-originated protein kinase |
| 56155 | TEX14 | testis expressed sequence 14 |
| 56164 | STK31 | serine/threonine kinase 31 |
| 56848 | SPHK2 | sphingosine kinase 2 |
| 56911 | C21orf7 | chromosome 21 open reading frame 7; C21orf7 |
| 56924 | PAK6 | p21(CDKN1A)-activated kinase 6 |
| 56997 | CABC1 | chaperone, ABC1 activity of bc1 complex like (*S. pombe*) |
| 57118 | CAMK1D | calcium/calmodulin-dependent protein kinase ID |
| 57143 | ADCK1 | aarF domain containing kinase 1 |
| 57144 | PAK7 | p21(CDKN1A)-activated kinase 7 |
| 57147 | PACE-1 | ezrin-binding partner PACE-1 |
| 57172 | CAMK1G | calcium/calmodulin-dependent protein kinase IG |
| 57396 | CLK4 | CDC-like kinase 4 |
| 57410 | SCYL1 | SCY1-like 1 (*S. cerevisiae*) |
| 57538 | ALPK3 | alpha-kinase 3 |
| 57551 | TAOK1 | TAO kinase 1 |
| 57729 | KIAA1639 | KIAA1639 protein |
| 57761 | TRIB3 | tribbles homolog 3 (*Drosophila*) |
| 57787 | MARK4 | MAP/microtubule affinity-regulating kinase 4 |
| 58538 | MPP4 | membrane protein, palmitoylated 4 (MAGUK p55 subfamily member 4); MPP4 |
| 60493 | FASTKD5 | FAST kinase domains 5; FASTKD5 |
| 64080 | RBKS | ribokinase |
| 64089 | SNX16 | sorting nexin 16; SNX16 |
| 64122 | FN3K | fructosamine 3 kinase |
| 64149 | NJMU-R1 | protein kinase Njmu-R1 |
| 64398 | MPP5 | membrane protein, palmitoylated 5 (MAGUK p55 subfamily member 5); MPP5 |
| 64768 | IPPK | inositol 1,3,4,5,6-pentakisphosphate 2-kinase; IPPK |
| 64781 | CERK | ceramide kinase |
| 65018 | PINK1 | PTEN induced putative kinase 1 |
| 65061 | ALS2CR7 | amyotrophic lateral sclerosis 2 (juvenile) chromosome region, candidate 7 |
| 65125 | PRKWNK1 | protein kinase, lysine deficient 1 |
| 65220 | FLJ13052 | NAD kinase |
| 65266 | PRKWNK4 | protein kinase, lysine deficient 4 |
| 65267 | PRKWNK3 | protein kinase, lysine deficient 3 |
| 65268 | PRKWNK2 | protein kinase, lysine deficient 2 |
| 65975 | STK33 | serine/threonine kinase 33 |
| 79012 | MGC8407 | hypothetical protein MGC8407 |
| 79072 | FASTKD3 | FAST kinase domains 3; FASTKD3 |
| 79646 | PANK3 | pantothenate kinase 3 |
| 79672 | FN3KRP | fructosamine-3-kinase-related protein |
| 79675 | FASTKD1 | FAST kinase domains 1; FASTKD1 |
| 79705 | LRRK1 | leucine-rich repeat kinase 1 |
| 79834 | KIAA2002 | KIAA2002 protein |
| 79837 | PIP5K2C | phosphatidylinositol-4-phosphate 5-kinase, type II, gamma |
| 79858 | NEK11 | NIMA (never in mitosis gene a)- related kinase 11 |
| 79877 | DCAKD | dephospho-CoA kinase domain containing; DCAKD |
| 79906 | MORN1 | MORN repeat containing 1; MORN1 |
| 79934 | ADCK4 | aarF domain containing kinase 4 |
| 80025 | PANK2 | pantothenate kinase 2 (Hallervorden-Spatz syndrome) |
| 80122 | FLJ23074 | hypothetical protein FLJ23074 |
| 80201 | HKDC1 | hexokinase domain containing 1; HKDC1 |
| 80216 | ALPK1 | alpha-kinase 1 |
| 80271 | ITPKC | inositol 1,4,5-trisphosphate 3-kinase C |

TABLE 1-continued

| NCBI Gene ID | Official Symbol | Description |
|---|---|---|
| 80347 | COASY | Coenzyme A synthase; COASY |
| 80851 | SH3BP5L | SH3-binding domain protein 5-like; SH3BP5L |
| 80852 | GRIP2 | glutamate receptor interacting protein 2; GRIP2 |
| 81629 | STK22C | serine/threonine kinase 22C (spermiogenesis associated) |
| 81788 | SNARK | likely ortholog of rat SNF1/AMP-activated protein kinase |
| 83440 | ADPGK | ADP-dependent glucokinase |
| 83549 | UCK1 | uridine-cytidine kinase 1 |
| 83694 | RPS6KL1 | ribosomal protein S6 kinase-like 1 |
| 83732 | RIOK1 | RIO kinase 1 (yeast) |
| 83903 | GSG2 | haspin |
| 83931 | MGC4796 | Ser/Thr-like kinase |
| 83942 | STK22D | serine/threonine kinase 22D (spermiogenesis associated) |
| 83983 | SSTK | serine/threonine protein kinase SSTK |
| 84033 | OBSCN | obscurin, cytoskeletal calmodulin and titin-interacting RhoGEF |
| 84197 | FLJ23356 | hypothetical protein FLJ23356 |
| 84206 | RKHD3 | ring finger and KH domain containing 3; RKHD3 |
| 84254 | CAMKK1 | calcium/calmodulin-dependent protein kinase kinase 1, alpha |
| 84284 | C1orf57 | chromosome 1 open reading frame 57; C1orf57 |
| 84433 | CARD11 | caspase recruitment domain family, member 11; CARD11 |
| 84446 | KIAA1811 | KIAA1811 protein |
| 84451 | KIAA1804 | mixed lineage kinase 4 |
| 84630 | TTBK1 | tau tubulin kinase 1 |
| 84930 | MASTL | microtubule associated serine/threonine kinase-like |
| 85366 | MYLK2 | myosin light chain kinase 2, skeletal muscle |
| 85443 | KIAA1765 | KIAA1765 protein |
| 85481 | PSKH2 | protein serine kinase H2 |
| 89882 | NYD-SP25 | protein kinase NYD-SP25 |
| 90381 | MGC45866 | leucine-rich repeat kinase 1 |
| 90956 | ADCK2 | aarF domain containing kinase 2 |
| 91156 | DKFZp434B1231 | eEF1A2 binding protein; DKFZp434B1231 |
| 91419 | XRCC6BP1 | XRCC6 binding protein 1; XRCC6BP1 |
| 91461 | LOC91461 | hypothetical protein BC007901 |
| 91584 | PLXNA4B | plexin A4, B; PLXNA4B |
| 91754 | NEK9 | NIMA (never in mitosis gene a)- related kinase 9 |
| 91807 | LOC91807 | myosin light chain kinase (MLCK) |
| 92335 | LYK5 | protein kinase LYK5 |
| 93627 | MGC16169 | hypothetical protein MGC16169 |
| 112858 | TP53RK | TP53 regulating kinase |
| 114783 | LMTK3 | lemur tyrosine kinase 3 |
| 114836 | SLAMF6 | SLAM family member 6; SLAMF6 |
| 115701 | ALPK2 | alpha-kinase 2 |
| 117283 | IHPK3 | inositol hexaphosphate kinase 3 |
| 120892 | LRRK2 | leucine-rich repeat kinase 2 |
| 122011 | CSNK1A1L | casein kinase 1, alpha 1-like |
| 122481 | AK7 | adenylate kinase 7 |
| 124923 | FLJ25006 | hypothetical protein FLJ25006 |
| 127933 | UHMK1 | U2AF homology motif (UHM) kinase 1 |
| 130106 | CIB4 | calcium and integrin binding family member 4; CIB4 |
| 130399 | ACVR1C | activin A receptor, type IC |
| 131890 | GRK7 | G protein-coupled receptor kinase 7 |
| 132158 | GLYCTK | glycerate kinase |
| 136332 | LRGUK | leucine-rich repeats and guanylate kinase domain containing; LRGUK |
| 138429 | PIP5KL1 | phosphatidylinositol-4-phosphate 5-kinase-like 1 |
| 138474 | TAF1L | TAF1-like RNA polymerase II, TATA box binding protein (TBP)-associated factor, 210 kDa |
| 139189 | DGKK | diacylglycerol kinase, kappa; DGKK |
| 139728 | PNCK | pregnancy upregulated non-ubiquitously expressed CaM kinase |
| 140469 | MYO3B | myosin IIIB |
| 140609 | NEK7 | NIMA (never in mitosis gene a)-related kinase 7 |
| 140803 | TRPM6 | transient receptor potential cation channel, subfamily M, member 6 |
| 140901 | STK35 | serine/threonine kinase 35 |
| 143098 | MPP7 | membrane protein, palmitoylated 7 (MAGUK p55 subfamily member 7); MPP7 |
| 146057 | TTBK2 | tau tubulin kinase 2 |
| 147746 | HIPK4 | homeodomain interacting protein kinase 4 |
| 149420 | PDIK1L | PDLIM1 interacting kinase 1 like |
| 150094 | SNF1LK | SNF1-like kinase |
| 152110 | NEK10 | NIMA (never in mitosis gene a)- related kinase 10 |
| 157285 | DKFZp761P0423 | hypothetical protein DKFZp761P0423 |
| 158067 | C9orf98 | chromosome 9 open reading frame 98; C9orf98 |
| 160851 | DGKH | diacylglycerol kinase, eta |
| 166614 | MGC45428 | hypothetical protein MGC45428 |
| 167359 | MGC42105 | hypothetical protein MGC42105 |
| 169436 | C9orf96 | chromosome 9 open reading frame 96 |
| 197258 | FUK | fucokinase |
| 197259 | FLJ34389 | hypothetical protein FLJ34389 |
| 200576 | PIP5K3 | phosphatidylinositol-3-phosphate/phosphatidylinositol 5-kinase, type III |
| 202374 | STK32A | serine/threonine kinase 32A |

TABLE 1-continued

| NCBI Gene ID | Official Symbol | Description |
|---|---|---|
| 203054 | ADCK5 | aarF domain containing kinase 5 |
| 203447 | NRK | Nik related kinase |
| 204851 | HIPK1 | homeodomain interacting protein kinase 1 |
| 220686 | LOC220686 | hypothetical protein LOC220686; LOC220686 |
| 221823 | PRPS1L1 | phosphoribosyl pyrophosphate synthetase 1-like 1; PRPS1L1 |
| 225689 | ERK8 | extracellular signal-regulated kinase 8 |
| 253430 | IPMK | inositol polyphosphate multikinase |
| 255239 | ANKK1 | ankyrin repeat and kinase domain containing 1 |
| 256356 | MGC40579 | hypothetical protein MGC40579; MGC40579 |
| 260425 | MAGI-3 | membrane-associated guanylate kinase-related (MAGI-3) |
| 282974 | STK32C | serine/threonine kinase 32C |
| 283284 | IGSF22 | immunoglobulin superfamily, member 22; IGSF22 |
| 283455 | KSR2 | kinase suppressor of Ras-2 |
| 283629 | C14orf20 | chromosome 14 open reading frame 20 |
| 284086 | NEK8 | NIMA (never in mitosis gene a)- related kinase 8 |
| 284656 | EPHA10 | EphA10s protein |
| 285220 | EPHA6 | EPH receptor A6 |
| 285962 | FLJ40852 | hypothetical protein FLJ40852 |
| 340156 | LOC340156 | hypothetical protein LOC340156 |
| 340371 | LOC340371 | hypothetical protein LOC340371 |
| 341676 | NEK5 | NIMA (never in mitosis gene a)-related kinase 5 |
| 344387 | CDKL4 | cyclin-dependent kinase-like 4 |
| 347359 | BMP2KL | BMP2 inducible kinase-like |
| 347736 | TXNDC6 | thioredoxin domain containing 6; TXNDC6 |
| 374872 | C19orf35 | chromosome 19 open reading frame 35; C19orf35 |
| 375133 | LOC375133 | similar to phosphatidylinositol 4-kinase alpha |
| 375298 | CERKL | ceramide kinase-like |
| 375449 | LOC375449 | similar to microtubule associated testis specific serine/threonine protein kinase |
| 378464 | MORN2 | MORN repeat containing 2; MORN2 |
| 387851 | AK3L2 | adenylate kinase 3-like 2 |
| 388228 | LOC388228 | similar to SH3-binding kinase |
| 388259 | LOC388259 | similar to protein kinase related to Raf protein kinases; Method: conceptual translation supplied by author |
| 388957 | LOC388957 | similar to BMP2 inducible kinase |
| 389599 | LOC389599 | similar to amyotrophic lateral sclerosis 2 (juvenile) chromosome region, candidate 2; ILP-interacting protein ILPIPA |
| 389840 | FLJ16518 | FLJ16518 protein |
| 389906 | LOC389906 | similar to Serine/threonine-protein kinase PRKX (Protein kinase PKX1) |
| 390877 | LOC390877 | similar to adenylate kinase (EC 2.7.4.3), cytosolic - common carp |
| 391295 | LOC391295 | similar to spermiogenesis associated serine/threonine kinase 220; serine/threonine kinase FKSG81; spermiogenesis associated 4 |
| 391533 | LOC391533 | similar to Vascular endothelial growth factor receptor 1 precursor (VEGFR-1) (Vascular permeability factor receptor) (Tyrosine-protein kinase receptor FLT) (Flt-1) (Tyrosine-protein kinase FRT) (Fms-like tyrosine kinase 1) |
| 392226 | LOC392226 | similar to Serine/threonine-protein kinase PLK1 (Polo-like kinase 1) (PLK-1) (Serine-threonine protein kinase 13) (STPK13) |
| 392265 | LOC392265 | similar to Cell division protein kinase 5 (Tau protein kinase II catalytic subunit) (TPKII catalytic subunit) (Serine/threonine-protein kinase PSSALRE) |
| 392347 | LOC392347 | similar to adenylate kinase 3 alpha like; adenylate kinase 6 |
| 400301 | LOC400301 | similar to protein kinase CHK2 isoform b; checkpoint-like protein CHK2; serine/threonine-protein kinase CHK2; CHK2 (checkpoint, S. pombe) homolog |
| 402289 | LOC402289 | similar to Ser/Thr protein kinase PAR-1Balpha |
| 402679 | LOC402679 | similar to Ser/Thr protein kinase PAR-1Balpha |
| 415116 | PIM3 | serine/threonine-protein kinase pim-3 |
| 440275 | LOC440275 | similar to GCN2 eIF2alpha kinase |
| 440345 | LOC440345 | similar to PI-3-kinase-related kinase SMG-1 isoform 1; lambda/iota protein kinase C-interacting protein; phosphatidylinositol 3-kinase-related protein kinase |
| 441047 | LOC441047 | similar to Adenylate kinase isoenzyme 4, mitochondrial (ATP-AMP transphosphorylase) |
| 441655 | LOC441655 | similar to chromosome 9 open reading frame 12; 1,3,4,5,6-pentakisphosphate 2-kinase |
| 441708 | LOC441708 | similar to CDC42-binding protein kinase alpha isoform A; ser-thr protein kinase related to the myotonic dystrophy protein kinase; ser-thr protein kinase PK428; myotonic dystrophy kinase-related CDC42-binding protein kinase alpha; CDC42 binidng prot . . . |
| 441733 | LOC441733 | similar to Serine/threonine-protein kinase PRKX (Protein kinase PKX1) |
| 441777 | LOC441777 | similar to Serine/threonine-protein kinase PLK1 (Polo-like kinase 1) (PLK-1) (Serine-threonine protein kinase 13) (STPK13) |
| 441971 | LOC441971 | similar to phosphoinositide 3-hydroxykinase p110-alpha subunit |
| 442075 | LOC442075 | similar to serine/threonine kinase, establishes embryonic polarity; asymmetrically distributed., abnormal embryonic PARtitioning of cytoplasm PAR-1, ZYGote defective: embryonic lethal ZYG-14 (126.3 kD) (par-1) |
| 442313 | LOC442313 | similar to Phosphorylase B kinase gamma catalytic chain, skeletal muscle isoform (Phosphorylase kinase gamma subunit 1) |
| 442558 | LOC442558 | similar to Phosphorylase B kinase gamma catalytic chain, skeletal muscle isoform (Phosphorylase kinase gamma subunit 1) |
| 548596 | CKMT1A | creatine kinase, mitochondrial 1A; CKMT1A |
| 641857 | LOC641857 | similar to Nucleoside diphosphate kinase, mitochondrial precursor (NDP kinase, mitochondrial) (NDK) (nm23-H4) (Nucleoside diphosphate kinase D) (NDPKD); unassigned |

TABLE 1-continued

| NCBI Gene ID | Official Symbol | Description |
|---|---|---|
| 642355 | LOC642355 | similar to Nucleoside diphosphate kinase, mitochondrial precursor (NDP kinase, mitochondrial) (NDK) (nm23-H4) (Nucleoside diphosphate kinase D) (NDPKD); unassigned |
| 642483 | LOC642483 | similar to fibroblast growth factor receptor 2 isoform IIIb; unassigned |
| 644462 | LOC644462 | similar to amyotrophic lateral sclerosis 2 (juvenile) chromosome region, candidate 2; unassigned |
| 644644 | LOC644644 | similar to Serine/threonine-protein kinase PRKX (Protein kinase PKX1); unassigned |
| 645118 | LOC645118 | similar to microtubule associated serine/threonine kinase 2; unassigned |
| 645146 | LOC645146 | similar to Kinase suppressor of ras-1 (Kinase suppressor of ras); unassigned |
| 645619 | LOC645619 | similar to Adenylate kinase isoenzyme 4, mitochondrial (ATP-AMP transphosphorylase); unassigned |
| 645739 | 408E5.4 | similar to CDC42-binding protein kinase beta; unassigned |
| 646096 | LOC646096 | similar to protein kinase CHK2 isoform b; unassigned |
| 646505 | LOC646505 | similar to Dual specificity protein kinase CLK3 (CDC-like kinase 3); unassigned |
| 646643 | LOC646643 | similar to protein kinase Bsk146; unassigned |
| 646780 | LOC646780 | similar to Phosphorylase b kinase alpha regulatory chain, skeletal muscle isoform (Phosphorylase kinase alpha M subunit); unassigned |
| 646836 | LOC646836 | similar to CDC42-binding protein kinase beta; unassigned |
| 647138 | LOC647138 | similar to Kinase suppressor of ras-1 (Kinase suppressor of ras); unassigned |
| 647176 | LOC647176 | similar to Kinase suppressor of ras-1 (Kinase suppressor of ras); unassigned |
| 647279 | LOC647279 | similar to MAP/microtubule affinity-regulating kinase 3; unassigned |
| 647935 | LOC647935 | similar to fibroblast growth factor receptor 2 isoform IIIb; unassigned |
| 648152 | LOC648152 | similar to ataxia telangiectasia and Rad3 related protein; unassigned |
| 648482 | LOC648482 | similar to MAP/microtubule affinity-regulating kinase 3; unassigned |
| 649288 | LOC649288 | similar to Adenylate kinase isoenzyme 4, mitochondrial (Adenylate kinase 3-like 1) (ATP-AMP transphosphorylase); unassigned |
| 649407 | LOC649407 | similar to Dual specificity protein kinase CLK3 (CDC-like kinase 3); unassigned |
| 649970 | LOC649970 | similar to creatine kinase, mitochondrial 1B precursor; unassigned |
| 650122 | LOC650122 | similar to choline kinase alpha isoform a; unassigned |
| 650168 | BRDG1 | similar to amyotrophic lateral sclerosis 2 (juvenile) chromosome region, candidate 2; unassigned |
| 650459 | LOC650459 | similar to CDC42-binding protein kinase beta; unassigned |
| 650556 | LOC650556 | similar to Phosphorylase b kinase gamma catalytic chain, testis/liver isoform (PHK-gamma-T) (Phosphorylase kinase gamma subunit 2) (PSK-C3); unassigned |
| 650832 | LOC650832 | similar to mitogen-activated protein kinase kinase 3 isoform A; unassigned |
| 651008 | LOC651008 | similar to mitogen-activated protein kinase kinase 3 isoform A; unassigned |
| 651423 | LOC651423 | similar to mitogen-activated protein kinase kinase 3 isoform A; unassigned |
| 651610 | LOC651610 | similar to Serine-protein kinase ATM (Ataxia telangiectasia mutated) (A-T, mutated); unassigned |
| 651771 | LOC651771 | similar to apoptosis-associated tyrosine kinase; unassigned |
| 651921 | LOC651921 | similar to ataxia telangiectasia and Rad3 related protein; unassigned |
| 652041 | LOC652041 | similar to 3-phosphoinositide dependent protein kinase 1 (hPDK1); unassigned |
| 652662 | LOC652662 | similar to Janus kinase 3; unassigned |
| 652722 | LOC652722 | similar to PTK2 protein tyrosine kinase 2 isoform a; unassigned |
| 652799 | LOC652799 | similar to Mast/stem cell growth factor receptor precursor (SCFR) (Proto-oncogene tyrosine-protein kinase Kit) (c-kit) (CD117 antigen); unassigned |
| 653052 | LOC653052 | similar to Homeodomain-interacting protein kinase 2 (hHIPk2); unassigned |
| 653155 | LOC653155 | similar to PRP4 pre-mRNA processing factor 4 homolog B; unassigned |
| 653882 | LOC653882 | similar to Mast/stem cell growth factor receptor precursor (SCFR) (Proto-oncogene tyrosine-protein kinase Kit) (c-kit) (CD117 antigen); unassigned |
| 654364 | NME1-NME2 | NME1-NME2 protein; NME1-NME2 |
| 727758 | LOC727758 | similar to Rho-associated protein kinase 1 (Rho-associated, coiled-coil-containing protein kinase 1) (p160 ROCK-1) (p160ROCK) (NY-REN-35 antigen); unassigned |
| 727761 | LOC727761 | similar to deoxythymidylate kinase (thymidylate kinase); unassigned |
| 728642 | LOC728642 | similar to cell division cycle 2-like 1 (PITSLRE proteins) isoform 1; unassigned |
| 728687 | LOC728687 | similar to Serine/threonine-protein kinase PRKX (Protein kinase PKX1); unassigned |
| 729116 | LOC729116 | similar to protein kinase, X-linked; unassigned |
| 729871 | LOC729871 | similar to aortic preferentially expressed gene 1; unassigned |
| 729937 | LOC729937 | similar to microtubule associated serine/threonine kinase 2; unassigned |
| 729985 | LOC729985 | similar to CDC42-binding protein kinase beta; unassigned |
| 730000 | LOC730000 | similar to testis-specific serine kinase 6; unassigned |
| 730418 | LOC730418 | similar to protein kinase, cAMP-dependent, catalytic, gamma; unassigned |
| 731007 | LOC731007 | similar to Adenylate kinase isoenzyme 4, mitochondrial (Adenylate kinase 3-like 1) (ATP-AMP transphosphorylase); unassigned |
| 731055 | LOC731055 | similar to testis-specific serine kinase 6; unassigned |
| 731082 | LOC731082 | similar to Serine/threonine-protein kinase tousled-like 2 (Tousled-like kinase 2); unassigned |
| 731295 | LOC731295 | similar to microtubule associated serine/threonine kinase 2; unassigned |
| 731320 | LOC731320 | similar to obscurin, cytoskeletal calmodulin and titin-interacting RhoGEF; unassigned |
| 731391 | LOC731391 | similar to creatine kinase, mitochondrial 1B precursor; unassigned |
| 731751 | LOC731751 | similar to protein kinase, DNA-activated, catalytic polypeptide; unassigned |
| 732306 | LOC732306 | similar to *vaccinia* related kinase 2; unassigned |
| 732371 | LOC732371 | similar to mixed lineage kinase domain-like; unassigned |
| 732396 | LOC732396 | similar to serine/threonine kinase 36 (fused homolog, *Drosophila*); unassigned |
| 732432 | LOC732432 | similar to Rho-associated protein kinase 1 (Rho-associated, coiled-coil-containing protein kinase 1) (p160 ROCK-1) (p160ROCK) (NY-REN-35 antigen); unassigned |

TABLE 2

|  | vector | C-Raf 22W | B-Raf$^{E600}$ | MEK$^{DD}$ |
|---|---|---|---|---|
| Anchorage-independent growth | | | | |
| vector | − | − | − | +/− |
| PTEN-shRNA | − | + | − | − |
| myr-110α | − | − | − | + |
| myr-AKT | +/− | + | +++ | +++ |
| H-RAS$^{V12}$ | +++ | | | |
| Tumor formation | | | | |
| vector | − | − | − | − |
| PTEN-shRNA | − | − | − | − |
| myr-110α | − | − | − | ++ |
| myr-AKT | − | − | − | +++ |
| H-RAS$^{V12}$ | +++ | | | |

Transformation of HEK cells expressing hTERT, the SV40ER plus the indicated constructs. Transformation was assessed by both anchorage-independent growth (upper) and the capacity for tumor formation in immunodeficient mice (lower).
Colony formation was scored as follows: (−): no colonies, (+/−): few microscopic (100 μm-200 nm) colonies, (+): many microscopic colonies, (++): microscopic- and small macroscopic (200 nm-1 mm) colonies, (+++): small macroscopic and large macroscopic (>1 mm) colonies.
Tumors (3 injections per cell line) were scored as follows: (−): no tumors, (+): single tumor > 8 week latency, (++): single tumor < 8 week latency or multiple tumors > 8 week latency, (+++): multiple tumors < 8 week latency.

The invention claimed is:

1. A composition comprising one or more nucleic acids, wherein
   (a) each nucleic acid encodes at least one activatable kinase or biologically active fragments thereof;
   (b) the composition encodes at least two activatable kinases or biologically active fragments thereof among the nucleic acids;
   (c) the activatable kinases or biologically active fragments are linked to one or more constitutive oligomerization domain activation signals;
   (d) the at least two activatable kinases or biologically active fragments thereof are selected from the group consisting of B-Raf, ALK, VEGFR, EGFR, Her2, and FGFR2; and
   (e) expression of the activatable kinases or biologically active fragments thereof in a cell results in the activatable kinases or biologically active fragments thereof being activated.

2. The composition of claim 1, wherein the one or more nucleic acids encode at least three activatable kinases or biologically active fragments thereof.

3. The composition of claim 2, wherein the one or more nucleic acids encode at least five activatable kinases or biologically active fragments thereof.

4. The composition of claim 3, wherein the one or more nucleic acids encode at least ten activatable kinases or biologically active fragments thereof.

5. The composition of claim 1, wherein the kinases are selected from the group of kinases set forth in Table 1.

6. The composition of claim 1, wherein the constitutive oligomerization domain activation signal is linked to the N-terminus of the kinases or biologically active portions thereof.

7. The composition of claim 1, wherein the oligomerization domain is a dimerization domain.

8. The composition of claim 1, wherein the oligomerization domain is linked to the C-terminus of the kinases or biologically active portions thereof.

9. The composition of claim 1, wherein one or more of the activatable kinases or biologically active portions thereof is an intracellular kinase domain of a receptor tyrosine kinase.

10. The composition of claim 1, wherein at least one of the activatable kinases or biologically active portions thereof is further linked to a detectable peptide.

11. The composition of claim 10, wherein the detectable peptide is a FLAG tag.

12. The composition of claim 1, wherein at least one of the one or more activatable kinases or biologically active portions thereof is linked directly to the one or more ligand independent oligomerization domain activation signals.

13. The composition of claim 1, wherein at least one of the one or more activatable kinases or biologically active portions thereof is linked to the one or more ligand independent oligomerization domain activation signals through a linker.

14. The composition of claim 1, wherein the one or more nucleic acids comprises one or more strong transcriptional regulatory sequence controlling the expression of the regulatable proteins.

15. The composition of claim 14, wherein the nucleic acids are in an expression vector.

16. The composition of claim 15, wherein the expression vector is a viral expression vector.

17. The composition of claim 1, further comprising a reagent for introducing the composition into a cell.

18. The composition of claim 1, which is in contact with a cell.

19. The composition of claim 18, wherein the cell is an immortalized, non-tumorigenic cell.

20. The composition of claim 19, wherein the cell is a human cell.

21. The composition of claim 19, wherein the cell is a murine cell.

22. The composition of claim 1, comprising at least two nucleic acids, wherein each nucleic acid encodes an activatable kinase or biologically active fragment thereof linked to one or more constitutive oligomerization domain activation signals.

23. The composition of claim 1, comprising at least five nucleic acids, wherein each nucleic acid encodes an activatable kinase or biologically active fragment thereof linked to one or more constitutive oligomerization domain activation signals.

24. The composition of claim 1 or 7, wherein the constitutive oligomerization domain activation signals are selected from the group consisting of the helix-loop-helix domain of TEL, the coiled-coil domain of RGF, the leucine zipper domain of GCN4, the PDZ domain of nNOS, the PDZ domain of syntrophin, and the heterodimerization domain of XLIM1/LDB1.

25. A cell comprising a composition of claim 1.

26. A kit comprising one or more nucleic acids, wherein
   (a) each nucleic acid encodes at least one activatable kinase or biologically active fragments thereof;
   (b) the composition encodes at least two activatable kinases or biologically active fragments thereof among the nucleic acids;

(c) the activatable kinases or biologically active fragments are linked to one or more constitutive oligomerization domain activation signals;

(d) the at least two activatable kinases or biologically active fragments thereof are selected from the group consisting of B-Raf, ALK, VEGFR, EGFR, Her2, and FGFR2; and (e) expression of the activatable kinases or biologically active fragments thereof in a cell results in the activatable kinases or biologically active fragments thereof being activated, and packaging for said kit.

27. The kit of claim 26, wherein the constitutive oligomerization domain activation signals are selected from the group consisting of the helix-loop-helix domain of TEL, the coiled-coil domain of RGF, the leucine zipper domain of GCN4, the PDZ domain of nNOS, the PDZ domain of syntrophin, and the heterodimerization domain of XLIM1/LDB 1.

28. A method comprising contacting one or more cells with a composition of claim 1.

29. The method of claim 28, wherein the cells are contacted with the composition under conditions in which at least some of the nucleic acids of the composition are taken up by the cells.

30. The method of claim 29, wherein the cells constitutively express one or more genes selected from the group consisting of the catalytic subunit of human telomerase (hTERT), the Large T (LT) of the SV40 Early Region and c-myc.

31. The method of claim 30, comprising determining whether the cells contacted with the nucleic acids grow in an anchorage-independent manner and/or promote tumor formation in animal hosts.

32. The method of claim 29, wherein the cells require a growth factor for growth and the method further comprises determining whether the cells contacted with the composition grow independently of the growth factor.

33. The method of claim 32, wherein the growth factor is IL-3.

34. The method of claim 28, wherein the cells are immortal but not tumorigenic cells.

35. The method of claim 34, further comprising determining whether the cells contacted with the composition are tumorigenic.

* * * * *